United States Patent
Smith et al.

(10) Patent No.: US 11,266,741 B2
(45) Date of Patent: Mar. 8, 2022

(54) NON-IONIC BLOCK PVP PLA BLOCK COPOLYMERS AND PHARMACEUTICAL COMPOSITIONS DERIVED THEREFROM

(71) Applicant: Altus Formulation Inc., Mirabel (CA)

(72) Inventors: Damon Smith, Montréal (CA); Wilms Baille, Laval (CA); Piotr Kujawa, Montréal (CA)

(73) Assignee: Altus Formulation Inc., Mirabel (CA)

( * ) Notice: Subject to any disclaimer, the term of this patent is extended or adjusted under 35 U.S.C. 154(b) by 0 days.

(21) Appl. No.: 16/497,925

(22) PCT Filed: Mar. 29, 2018

(86) PCT No.: PCT/CA2018/050399
§ 371 (c)(1),
(2) Date: Sep. 26, 2019

(87) PCT Pub. No.: WO2018/176158
PCT Pub. Date: Oct. 4, 2018

(65) Prior Publication Data
US 2021/0322556 A1      Oct. 21, 2021

Related U.S. Application Data

(60) Provisional application No. 62/479,582, filed on Mar. 31, 2017.

(51) Int. Cl.
*A61K 47/34*        (2017.01)
*A61K 9/107*        (2006.01)
(Continued)

(52) U.S. Cl.
CPC ............ *A61K 47/34* (2013.01); *A61K 9/1075* (2013.01); *A61K 9/5192* (2013.01); *A61K 31/05* (2013.01);
(Continued)

(58) Field of Classification Search
CPC .... A61K 47/34; A61K 31/167; A61K 31/192; A61K 31/415; A61K 31/05; A61K 9/1075; A61K 9/5192
See application file for complete search history.

(56) References Cited

FOREIGN PATENT DOCUMENTS

| CA | 2547938 A1 | 6/2005 |
| WO | 2011/130834 A1 * | 10/2011 |
| WO | 2011130834 A1 | 10/2011 |

OTHER PUBLICATIONS

Ravanelle et al., Aneasthetic Effect of Propofol Polymeric Micelles: A Novel Water Soluble Propofol Formulation, British Journal of Anaesthetics 101 (2): 86-193 (Year: 2008).*

(Continued)

*Primary Examiner* — Carlos A Azpuru
(74) *Attorney, Agent, or Firm* — Borden Ladner Gervais LLP; Graeme Boocock

(57) ABSTRACT

There are provided PVP-PLA block copolymers as defined in Formula (I): I wherein, x is an initiator alcohol having a boiling point greater than 145° C., n is, on average, from 20 and 40, and m is, on average, from 10 and 40, wherein the block copolymers have a number average molecular weight ($M_n$) of at least 3000 Da. Polymers demonstrating flexibility in formulating multiple low-solubility active pharmaceutical ingredients (APIs) are described. Liquid and dry pharmaceutical formulations comprising an API are described, along with delivery methods, uses, and kits. APIs may include, e.g. flurbiprofen, celecoxib, acetaminophen, or propofol. Also provided is a method of synthesizing the PVP-PLA block copolymers by (i) initiating polymerization of D,L-Lactide from the initiator alcohol x to form poly (lactic acid), adding a xanthate to form a PLA macroinitiator, and polymerizing NVP onto the PLA macroinitiator, by controlled polymerization, to form the block copolymer compound of Formula (I).

(Continued)

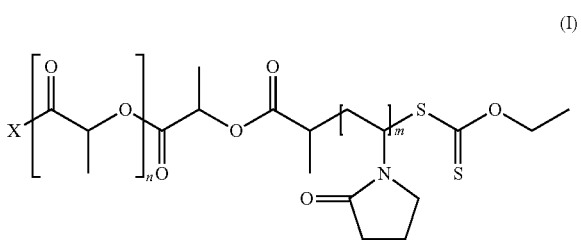

27 Claims, 27 Drawing Sheets

(51) Int. Cl.
 A61K 9/51 (2006.01)
 A61K 31/05 (2006.01)
 A61K 31/167 (2006.01)
 A61K 31/192 (2006.01)
 A61K 31/415 (2006.01)
(52) U.S. Cl.
 CPC .......... *A61K 31/167* (2013.01); *A61K 31/192* (2013.01); *A61K 31/415* (2013.01)

(56) References Cited

OTHER PUBLICATIONS

International Patent Application No. PCT/CA2018/050399, International Search Report and Written Opinion dated Jun. 21, 2018.
Le Garrec et al., "Poly(N-Vinylpyrrolidone)-Block-Poly(D,L-Lactide) as a New Polymeric Solubilizer for Hydrophobic Anticancer Drugs: In Vitro and in Vivo Evaluation," Journal of Controlled Release, 2004, vol. 99 (1), pp. 83-101.
Luo et al., "Novel Amphiphilic Diblock Copolymer of Low Molecular Weight Poly(N-vinylpyrrolidone)-block-poly(d,l-lactide): Synthesis, Characterization, and Micellization," Macromolecules, May 2004, vol. 37 (11), pp. 4008-4013.
Ramesh et al., "Synthesis of Well-Defined Amphiphilic Poly(D,L-lactide)-B-Poly(N-Vinylpyrrolidone) Block Copolymers using ROP and Xanthate-Mediated RAFT Polymerization," Polymers, Nov. 2012, vol. 53 (25), pp. 5743-5753.
Ravenelle et al., "Anaesthetic Effects of Propofol Polymeric Micelle: A Novel Water Soluble Propofol Formulation," British Journal of Anaesthesia, 2008, vol. 101 (2), pp. 186-193.
Ravenelle et al., "Novel Lipid and Preservative-Free Propofol Formulation: Properties and Pharmacodynamics," Pharmaceutical Research, Feb. 2008, vol. 25 (2), pp. 313-319.

United Kingdom Patent Application No. 1705287.9, Search Report dated Oct. 19, 2017.
United Kingdom Patent Application No. GB 1705287.9, Office Action dated Jul. 2, 2019.
Zhu et al.,"The Effect of Hydrophilic Chain Length and iRGD on Drug Delivery from Poly(ε-Caprolactone)-Poly(N-Vinylpyrrolidone) Nanoparticles," Biomaterials, Dec. 2011, vol. 32 (35), pp. 9525-9535.
European Patent Application No. 18777331.2, Extended European Search Report dated Oct. 29, 2020.
Albertsson and Varma, Recent Development in Ring Opening Polymerization of Lactones for Biomedical Applications, Biomacromolecules, 2003, vol. 4(6), pp. 1466-1486.
Bartolozzi et al., "Hydroxyl End-capped Macromers of N-vinyl-2-pyrrolidinone as Precursors of Amphiphilic Block Copolymers," European Polymer Journal, 2007, vol. 43, pp. 4628-4638.
Cefali et al., "Pharmacokinetic Comparison of Flurbiprofen in End-stage Renal Disease Subjects and Subjects With Normal Renal Function," Journal of Clinical Pharmacology, 1991, vol. 31, pp. 808-814.
European Patent Application No. 18777331.2, Communication under Rule 71(3) EPC dated Sep. 29, 2021.
Hans et al., "Microwave-Assisted Synthesis of 1,3-Dimesitylimidazolinium Chloride," Organic Syntheses, 2010, vol. 87, pp. 77-87.
Kaiser et al., "Pharmacokinetics of Flurbiprofen," The American Journal of Medicine, 1986, vol. 80(3A), pp. 10-15.
Knihinicki et l., "Stereoselective Disposition of Ibuprofen and Flurbiprofen in Rats," Chirality, 1990, vol. 2(3), pp. 134-140.
Kumpulainen et al., "Plasma and Cerebrospinal Fluid Pharmacokinetics of Flurbiprofen in Children,"British Journal of Clinical Pharmacology, 2010, vol. 70(4), pp. 557-566.
Masutani and Kimura., "PLA Synthesis. From the Monomer to the Polymer," The Royal Society of Chemistry, 2015, vol. 1, pp. 1-36.
Park and Kim., "Preparation and Evaluation of Flurbiprofen-Loaded Microemulsion for Parenteral Delivery," International Journal of Pharmaceutics, 1999, vol. 181(2), pp. 173-179.
Qayyum et al., "Determination of Pharmacokinetics of Flurbiprofen in Pakistani Population Using Modified HPLC Method," Journal of Chromatographic Science, 2011, vol. 49(2), pp. 108-113.
Szpunar et al., "Pharmacokinetics of Flurbiprofen in Man. I. Area/dose Relationships," Biopharmaceutics & Drug Disposition, 1987, vol. 8: pp. 273-283.
Taburet et al., "Pharmacokinetic Comparison of Oral and Local Action Transcutaneous Flurbiprofen in Healthy Volunteers," Journal of Clinical Pharmacy and Therapeutics, 1995, vol. 20, pp. 101-107.
Wang et al., "Synthesis, Degradability, and Cell Affinity of Poly (DL-lactide-co-RS-hydroxyethyl-beta-malolactonate)," Journal of Biomedical Materials Research. Part A, 2009, vol. 16, pp. 191-197.

\* cited by examiner

NON-IONIC BLOCK PVP PLA BLOCK COPOLYMERS AND PHARMACEUTICAL COMPOSITIONS DERIVED THEREFROM

CROSS REFERENCE TO RELATED APPLICATIONS

This application claims the benefit of priority of U.S. Provisional Patent Application No. 62/479,582 entitled NON-IONIC BLOCK COPOLYMERS AND PHARMACEUTICAL COMPOSITIONS DERIVED THEREFROM filed on Mar. 31, 2017, and from U.K. Application No 1705287.9 entitled NON-IONIC BLOCK COPOLYMERS AND PHARMACEUTICAL COMPOSITIONS DERIVED THEREFROM filed on Mar. 31, 2017, both of which are hereby incorporated by reference.

FIELD

The present disclosure relates generally related to carriers for active pharmaceutical ingredients (APIs). More particularly, the present disclosure relates to block copolymers for micellar delivery of APIs.

BACKGROUND

PVP-PLA is a non-ionic block copolymer of polyvinylpyrrolidone (PVP) and poly(D,L lactide) (PLA). PVP-PLA technology may be used for the formulation of active pharmaceutical ingredients (APIs) for delivery to individuals in need thereof, and is particularly useful for delivery of APIs of low solubility in water, or APIs that are water-insoluble. The technology has the ability to form micelles independently of the pH when the polymer concentration in water is above the critical micellar concentration (CMC) and to entrap APIs within their cores in the process. Such micelles are disrupted when the polymer concentration decreases below the CMC. Following this principle, API-loaded PVP-PLA micelles will begin to release their API content upon dilution, e.g., after injection into blood; however the CMC of the PVP-PLA/API formulation may vary depending on the nature of the drug so entrapped.

Although PVP-PLA is valuable for drug delivery, the technology remains challenging, for example due to one or more of: inefficient non-cost effective methods of synthesis; limitations on the ability to load different APIs; or limitations to the amount of API that may be loaded.

Therefore, there remains a need for PVP-PLA block copolymers that can be manufactured efficiently. There remains a need for flexible PVP-PLA drug delivery technologies with the ability to load respective APIs in sufficiently high concentration and/or to load a range of APIs. There remains a need for PVP-PLA block copolymer species having capacity to load API's in sufficiently high concentration so as make the administration of the PVP-PLA+API formulation as infrequent as possible.

SUMMARY

It is an object of the present disclosure to obviate or mitigate at least one disadvantage of previous approaches.

In a first aspect, the present disclosure provides PVP-PLA block copolymers as defined in Formula I:

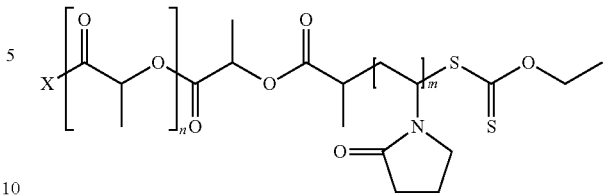

wherein x is an initiator alcohol having a boiling point greater than 145° C., n is, on average, from 20 and 40, and m is, on average, from 10 and 40, wherein the block coplymers have a number average molecular weight ($M_n$) of at least 3000 Da.

In another aspect, there is provided a nanovehicle delivery system comprising micelles formed of the PVP-PLA block copolymers.

In another aspect, there is provided a dry pharmaceutical composition comprising the PVP-PLA block copolymers in molecular association with at least one active pharmaceutical ingredient (API).

In another aspect, there is provided a liquid pharmaceutical composition comprising nanoparticles formed of the PVP-PLA block copolymers and comprising at least one active pharmaceutical ingredient (API).

In another aspect, there is provided a method of delivering at least one active pharmaceutical ingredient (API) to a subject in need thereof, comprising administering the dry pharmaceutical composition to the subject.

In another aspect, there is provided a method of delivering at least one active pharmaceutical ingredient (API) to a subject in need thereof, comprising administering the liquid pharmaceutical composition to the subject.

In another aspect, there is provided the dry pharmaceutical composition or the liquid pharmaceutical composition for use in delivery of at least one active pharmaceutical ingredient (API) to a subject.

In another aspect, there is provided a kit comprising the dry pharmaceutical composition or the liquid pharmaceutical composition, and instructions for use in delivery of at least one active pharmaceutical ingredient (API) to a subject.

In one aspect, the above-described block copolymers may find application in mitigation of haemolytic effects.

In one aspect, the above-described block copolymers may find application in mitigation of haemolytic activity of a cargo molecule.

In another aspect, there is provided a method of preparing PVP-PLA block copolymers as defined in Formula I:

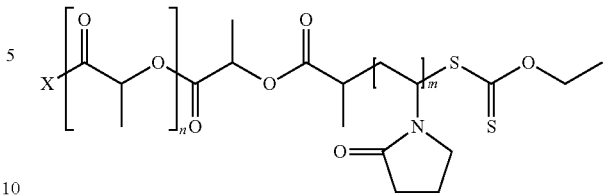

wherein x is an initiator alcohol having a boiling point greater than 145° C., n is, on average, from 20 and 40, m is, on average, from 10 and 40, and the block copolymers have a number average molecular weight (Mn) of at least 3000 Da the method comprising: initiating polymerization of D,L-Lactide from the initiator alcohol x to form poly(lactic acid) (PLA), adding a xanthate to the PLA to form a PLA macroinitiator, and polymerizing NVP, by controlled polymerization, onto the PLA macroinitiator to form the block copolymer compound of Formula I.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

PVP-PLA Block Copolymers

Figure 1:
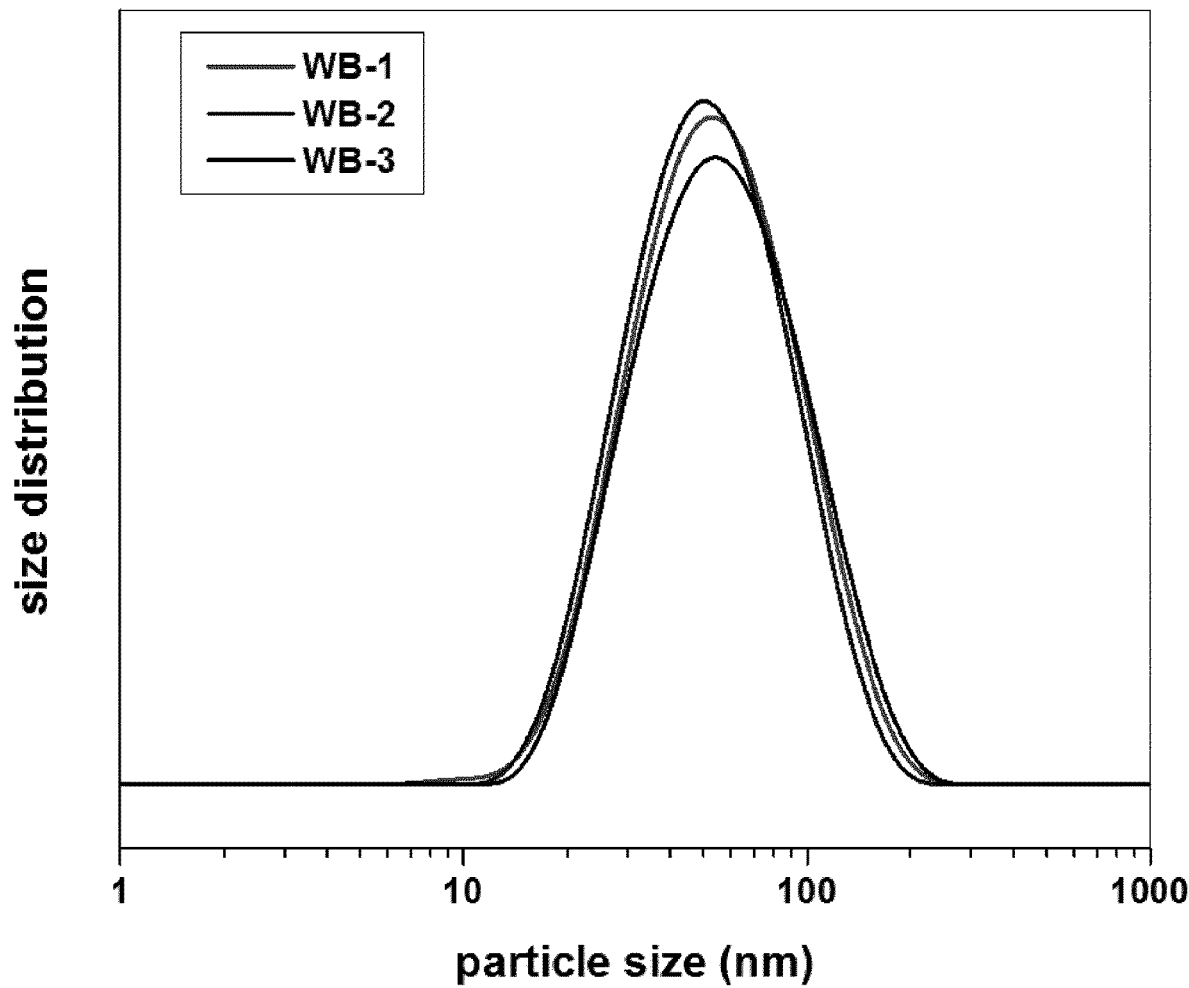
FIG. 1 depicts micelle size distribution obtained from three different batches of PVP-PLA polymer.

In one aspect, there are provided PVP-PLA block copolymers as defined in Formula I:

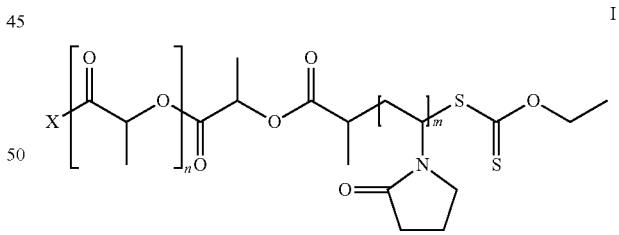

wherein: x is an initiator alcohol having a boiling point greater than 145° C., n is, on average, from 20 and 40, and m is, on average, from 10 and 40, wherein the block copolymers have a number average molecular weight ($M_n$) of at least 3000 Da.

By "initiator alcohol" is meant a species having a hydroxyl group capable of serving a substrate for polymerization, in this case of poly(D,L lactide) (PLA). It will be understood that reference to an "initiator alcohol" in the context of the above structure is intended to mean the reacted form thereof.

All boiling points referred to herein are at standard pressure. The boiling point of the initiator alcohol may be selected achieve desired efficiency of polymerization without problematic evaporation of the initiator alcohol.

In one embodiment, the initiator alcohol has a boiling point of greater than 150° C. In one embodiment, the initiator alcohol has a boiling point of greater than 160° C. In one embodiment, the initiator alcohol has a boiling point of greater than 170° C. In one embodiment, the initiator alcohol has a boiling point of greater than 180° C. In one embodiment, the initiator alcohol has a boiling point of greater than 190° C. In one embodiment, the initiator alcohol has a boiling point of greater than 200° C.

In one embodiment, the initiator alcohol is selected from the group consisting of: 1-hexanol; 1-heptanol; diethylene glycol monoethyl ether; diethylene glycol mono methyl ether; triethylene glycol mono methyl ether; tetraethylene glycol mono methyl ether; oligo-ethylene glycol mono methyl ethers of formula II $$H_3C\text{---}[O\text{---}]_a OH,\quad\text{II}$$

wherein a≥5;
oligo-ethylene glycol mono ethyl ethers of formula III $$CH_3\text{---}CH_2\text{---}[O\text{---}]_b OH,\quad\text{III}$$

wherein b≥1;
and mixtures thereof.

In one embodiment, x is diethylene glycol mono ethyl ether (DEGMEE).

The "number average molecular weight" ($M_n$) will be understood as the ordinary arithmetic mean or average of the molecular masses of the individual macromolecules. It is determined by measuring the molecular mass of n polymer molecules, summing the masses, and dividing by n:

$$\overline{M}_n = \frac{\sum_i N_i M_i}{\sum_i N_i}$$

Number average molecular weight of a polymer can be determined, e.g., by gel permeation chromatography, viscometry e.g. via the Mark-Houwink equation, colligative methods such as vapor pressure osmometry, end-group determination or proton NMR.

In one embodiment, the block copolymers are capable of forming nanoparticles with at least one active pharmaceutical ingredient (API), wherein the nanoparticles are suitable for administration to a subject. Nanoparticle formation may solubilize the API.

By "nanoparticles" are meant particles having a size of less than 200 nm. In some instances, the nanoparticles may be less than 100 nm in size. Nanoparticles may be sized to avoid or reduce renal excretion. For example, nanoparticles may be size greater than 15 nm. The nanoparticles referred to herein may be micelles.

By "micelle" will be understood as a supramolecular self-assembly comprised of molecules that arrange themselves in a generally spherical form in aqueous solutions. The formation of a micelle is a response to the amphipathic nature the PVP-PLA block copolymers, which contain both hydrophilic regions (PLA groups) as well as hydrophobic regions (PVP groups). A typical micelle in aqueous solution forms with the hydrophilic regions of the polymer in contact with surrounding solvent, sequestering the hydrophobic regions in the micelle centre. Herein, the term "micelle" or "micellar" also may be used to refer to the structure of a dried form of a previously liquid colloidal composition of micellar nanoparticles, wherein some elements of a micellar structure are retained in dried form, or wherein the dried form readily reforms micelles upon hydration.

Molecules, including APIs, can be solubilized through formation of a nanoparticles comprising the molecule or API. The nanoparticles may be a nanodispersion.

By "nanodispersion" is meant a dispersion of nanoparticles in a medium.

By "suitable for administration to a subject" is meant that the nanoparticles or a suspension of nanoparticles possesses properties that render them suitable for delivery to a subject, e.g. to meet safety requirements. The suspension of nanoparticles may, for example, meet requirements set out in USP 788, which inter alia sets limitations on the amount of particulate matter permitted in material intended for parenteral administration. These requirements are considered to be met if the number of particulates per (injection) container is less than 6000 for particles of 10 microns or greater, and less than 600 for particles equal of 25 microns or greater.

In some embodiments, the suspension of nanoparticles may be essentially clear. In some embodiments, the suspension may be free of visible particulate. By "essentially clear" is generally meant free of visible particulate matter. In some embodiments, the suspension may be free of sub-visible particulate.

In some embodiments, the suspension of nanoparticles may have an optical transmittance indicative of the general clearness of a solution. The optical transmittance may, for example, be an $OD_{650}$ of greater than 70%, 80%, 90%, 95%, 96%, 97%, or 98%, depending on requirements.

In some embodiment, wherein the block copolymers have a $M_n$ of less than 12,000 Da, 11,000 Da, 10,000 Da, 9,000 Da, 8000 Da, 7000 Da, or 6000 Da. In some embodiment, wherein the block copolymers have a $M_n$ of less than 7000 Da. In some embodiment, wherein the block copolymers have a $M_n$ of greater than 4000 Da, 5000 Da, or 6000 Da.

Group 1

In one embodiment, the block copolymers are capable of forming nanoparticles with at least one active pharmaceutical ingredient.

By "capable of forming nanoparticles" is meant that the block copolymers spontaneously form nanoparticles comprising the block copolymers and the API when mixed under suitable conditions. The nanoparticles may be stable, meaning that they persist as nanoparticles (subject to equilibrium) in an aqueous solution for a particular period of time. For instance, the nanoparticles may be stable for at least one day. The nanoparticles may be stable for at least two days. The nanoparticles may be stable for at least three days. Stability may be indicated by lack of formation of undesirable visible particulate or sediment. Nanoparticles formation may solubilize the API.

In one embodiment, the block copolymers are capable of forming nanoparticles with at least flurbiprofen (FLU). In one embodiment, n is, on average, from 20 to 28. In one embodiment, n is, on average, 21 to 27. In one embodiment, m is, on average, from 11 to 37. In one embodiment, m is, on average, from 12 to 36. In one embodiment, the PVP-PLA block copolymers have a number average molecular weight of 3000 Da to 6600 Da. In one embodiment, the PVP-PLA block copolymers have a number average molecular weight of 3100 Da to 6500 Da. In one embodiment, the PVP-PLA block copolymers have a number average molecular weight for the PLA block of 1400 Da to 2900 Da. In one embodiment, the PVP-PLA block copolymers have a number average molecular weight for the PLA block of 1500 Da to 2800 Da.

When a characteristic of the "PLA block" is referred to herein, it will be understood that this refers to the poly(lactic acid) component of the polymers. This value can be obtained, e.g., by using the values of Mn calculated by proton NMR in Table 20 for PLA-PEOX and subtracting the molecule weight of PEOX (121.2) and that of the initiator alcohol used (134.2).

In one embodiment, the PVP-PLA block copolymers have a number average molecular weight for the PVP block of 1200 Da to 4200 Da. In one embodiment, the PVP-PLA block copolymers have a number average molecular weight for the PVP block of 1300 Da to 4100 Da.

When a characteristic of the "PVP block" is referred to, it will be understood that this refers to the polyvinylpyrrolidone component of the polymers. This value can be obtained, e.g., by using the values of Mn calculated by proton NMR in Table 20 for PVP.

In one embodiment, the PVP-PLA block copolymers have a ratio of the number average molecular weight of the PLA block to the number average molecular weight of the PVP block (PLA:PVP) of about 0.3 to about 1.4. In one embodiment, the PVP-PLA block copolymers have a ratio of the number average molecular weight of the PLA block to the number average molecular weight of the PVP block (PLA:PVP) of about 0.4 to about 1.3.

In some embodiments, the PVP-PLA block copolymers may be defined by some or all of the parameters set forth for Group 1 polymers in Table 20. In some embodiments, the PVP-PLA block copolymers may possess some or all of the characteristics of polymers WB-DMAP, WB-1, WB-2, WB-3, WB-4, WB-5, WB-6, WB-7, or WB-8 from Table 20.

Group 2

In one embodiment, the PVP-PLA block copolymers are capable of forming nanoparticles with at least two different active pharmaceutical ingredients (APIs).

By "capable of forming nanoparticles with at least two different APIs" will be understood that the block copolymer can at least form nanoparticles with the at least two different APIs independently. In some embodiments, the nanoparticles may form nanoparticles with a mixture of the at least two different APIs.

In one embodiment, the at least two different APIs comprise flurbiprofen and celecoxib. In one embodiment, n is, on average, from 21.5 to 28. In one embodiment, n is, on average, from 22 to 27. In some embodiments, n may be, on average, about 24. In one embodiment, m is, on average, from 18 to 37. In one embodiment, m is, on average, from 19 to 36. In some embodiments, m may be, on average, about 29. In one embodiment, the PVP-PLA block copolymers have a number average molecular weight of 4600 Da to 6600 Da. In one embodiment, the PVP-PLA block copolymers have a number average molecular weight of 4700 Da to 6500 Da. In some embodiments, a number average molecular weight may be about 5700 Da. In one embodiment, the PVP-PLA block copolymers have a number average molecular weight for the PLA block of 1600 Da to 2900 Da. In one embodiment, the PVP-PLA block copolymers have a number average molecular weight for the PLA block of 1700 Da to 2800 Da. In one embodiment, the PVP-PLA block copolymers have a number average molecular weight for the PVP block of 1900 Da to 4200 Da. In one embodiment, the PVP-PLA block copolymers have a number average molecular weight for the PVP block of 2000 Da to 4100 Da. In one embodiment, the PVP-PLA block copolymers have a ratio of the number average molecular weight of the PLA block to the number average molecular weight of the PVP block (PLA:PVP) of 0.3 to 1.4. In one embodiment, the PVP-PLA block copolymers have a ratio of the number average molecular weight of the PLA block to the number average molecular weight of the PVP block (PLA:PVP) of 0.4 to 1.3. In one embodiment, the PVP-PLA block copolymers have a weight average molecular weight ($M_w$) of PLA in the block copolymers of 35% to 60%, based on the total weight of the polymer. In one embodiment, the PVP-PLA block copolymers have a weight average molecular weight ($M_w$) of PVP in the block copolymers of 40% to 65%, based on the total weight of the polymer. In some embodiments, the average $M_w$ of PLA is about 45% and the average $M_w$ of PVP is about 55%.

"Weight average molecular weight" ($M_w$) will be understood as another way of describing the molar mass of a polymer, wherein larger molecules have a larger contribution than a smaller molecule. The mass average molar mass is calculated by:

$$\overline{M}_w = \frac{\sum_i N_i M_i}{\sum_i N_i M_i}$$

wherein Ni is the number of molecules of molecular mass Mi. Mass average molecular mass can be determined, e.g., by static light scattering, small angle neutron scattering, X-ray scattering, and sedimentation velocity, relative gel permeation chromatography (GPC), or size exclusion chromatography (SEC).

In some embodiments, the PVP-PLA block copolymers may be defined by some or all of the parameters set forth for Group 2 polymers in Table 20. In some embodiments, the PVP-PLA block copolymers may possess some or all of the characteristics of polymers WB-1, WB-2, WB-3, WB-4, WB-5, WB-6, or WB-8 from Table 20.

Group 3

In one embodiment, the block copolymers are capable of forming nanoparticles with at least three different active pharmaceutical ingredients (APIs).

By "capable of forming nanoparticles with at least three different APIs" will be understood that the block copolymer can at least form nanoparticles with the at least three different APIs independently. In some embodiments, the nanoparticles may form nanoparticles with a mixture of the at least three different APIs.

In one embodiment, the at least three different APIs comprise at least three of flurbiprofen, celecoxib, acetaminophen, and propofol. In one embodiment, the at least three different APIs comprise all four of flurbiprofen, celecoxib, acetaminophen, and propofol. In one embodiment, n is, on average, from 21.5 to 28. In one embodiment, n is, on average, from 22 to 27. In some embodiments, n may be, on average, about 24. In one embodiment, m is, on average, from 25 to 37. In one embodiment, m is, on average, from 26 to 36. In some embodiments, m may be, on average, about 31. In one embodiment, the PVP-PLA block copolymers have a number average molecular weight of 4800 Da to 6600 Da. In one embodiment, the PVP-PLA block copolymers have a number average molecular weight of 4900 Da to 6500 Da. In some embodiments, the number average molecular weight is about 5900 Da. In one embodiment, the PVP-PLA block copolymers have a number average molecular weight for the PLA block of 1600 Da to 2900 Da. In one embodiment, the PVP-PLA block copolymers have a number average molecular weight for the PLA block of 1700 Da to 2800 Da. In one embodiment, the PVP-PLA block copolymers have a number average molecular weight for the PVP block of 2700 Da to 4200 Da. In one embodiment, the PVP-PLA block copolymers have a number average molecular weight for the PVP block of 2800 Da to 4100 Da. In one embodiment, the PVP-PLA block copolymers have a ratio of the number average molecular weight of the PLA block to the number average molecular weight of the PVP block (PLA:PVP) of 0.3 to 1.0. In one embodiment, the PVP-PLA block copolymers have a ratio of the number average molecular weight of the PLA block to the number average molecular weight of the PVP block (PLA:PVP) of 0.4 to 0.9. In one embodiment, the PVP-PLA block copolymers have a weight average molecular weight ($M_w$) of PLA in the block copolymers of 35% to 60%, based on the total weight of the polymer. In one embodiment, the PVP-PLA block copolymers have a weight average molecular weight ($M_w$) of PVP in the block copolymers of 40% to 65%, based on the total weight of the polymer. In some embodiments, the average $M_w$ of PLA is about 45% and the average $M_w$ of PVP is about 55%.

In some embodiments, the PVP-PLA block copolymers may be defined by some or all of the parameters set forth for Group 3 polymers in Table 20. In some embodiments, the PVP-PLA block copolymers may possess some or all of the characteristics of polymers WB-1, WB-2, WB-3, WB-4, WB-5, or WB-6.

Group 4

In one embodiment, the block copolymers may be a subset of those capable of forming nanoparticles with at least three different active pharmaceutical ingredients (APIs).

In one embodiment, n is, on average, from 24 to 28. In one embodiment, n is, on average, from 25 to 27. In some embodiments, n may be, on average, about 26. In one embodiment, m is, on average, from 25 to 33. In one embodiment, m is, on average, from 26 to 32. In some embodiments, m may be, on average, about 29. In one embodiment, the PVP-PLA block copolymers have a number average molecular weight of 5400 Da to 6600 Da. In one embodiment, the PVP-PLA block copolymers have a number average molecular weight of 5500 Da to 6500 Da. In some embodiments, the number average molecular weight is about 6000 Da. In one embodiment, the PVP-PLA block copolymers have a number average molecular weight for the PLA block of 2200 Da to 2900 Da. In one embodiment, the PVP-PLA block copolymers have a number average molecular weight for the PLA block of 2300 Da to 2800 Da. In one embodiment, the PVP-PLA block copolymers have a number average molecular weight for the PVP block of 2700 Da to 3700 Da. In one embodiment, the PVP-PLA block copolymers have a number average molecular weight for the PVP block of 2800 Da to 3600 Da. In one embodiment, the ratio of the number average molecular weight of the PLA block to the number average molecular weight of the PVP block (PLA:PVP) of 0.5 to 1.0. In one embodiment, the ratio of the number average molecular weight of the PLA block to the number average molecular weight of the PVP block (PLA:PVP) of 0.6 to 0.9. In one embodiment, the weight average molecular weight ($M_w$) of PLA in the block copolymers is 35% to 50%, based on the total weight of the polymer. In one embodiment, the weight average molecular weight ($M_w$) of PVP in the block copolymers is 50% to 65%, based on the total weight of the polymer. In some embodiments, the average $M_w$ of PLA is about 45% and the average $M_w$ of PVP is about 55%.

In some embodiments, the PVP-PLA block copolymers may be defined by some or all of the parameters set forth for Group 4 polymers in Table 20.

Groups 1 to 4

In the above embodiments under Groups 1 to 4 and earlier, the number average molecular weight may be as measured by proton nuclear magnetic resonance (NMR).

In the above embodiments under Groups 1 to 4 and earlier, the weight average molecular weight may be is as measured by thermogravimetric analysis (TGA).

In one embodiment, the PVP-PLA block copolymers have a polydispersity index (PDI) of ≤1.8. In one embodiment, the PVP-PLA block copolymers have a polydispersity index (PDI) of ≤1.6. In one embodiment, the PVP-PLA block copolymers have a polydispersity index (PDI) of ≤1.5. In one embodiment, the polydispersity index is ≤1.4. In one embodiment, the polydispersity index is ≤1.3. In one embodiment, the polydispersity index is ≤1.2. In one embodiment, the polydispersity index is ≤1.1. In one embodiment, the PDI is as measured by gel permeation chromatography with light scattering (GPC-LS).

Nanovehicle Delivery System

In one aspect, there is provided a nanovehicle delivery system comprising micelles formed of the above-described PVP-PLA block copolymers. By "nanovehicle delivery system" is meant nanoparticles formed of the above-described block co-polymers. The nanoparticles may consist of the above-describe block co-polymers in some embodiments. The nanovehicle delivery system may be useful for solubilizing another molecule, which may be of low solubility or hydrophobic. The nanovehicle delivery system may be useful for solubilizing one or more API, as described herein.

Dry Pharmaceutical Formulation

In one aspect, there is provided a dry pharmaceutical composition comprising the above-described PVP-PLA block copolymers in molecular association with at least one active pharmaceutical ingredient (API).

By "dry pharmaceutical composition" is meant a formulation prepared by drying (e.g., removing solvent) a mixture of the API and the block copolymers to form an intimate mixture of the API and the block copolymers. "Dry" here will be understood to mean "substantially dry", and indicates that the at least about 90%, at least about 95%, 96%, 97%, 98%, 99%, or 99.9%, of the solvent has been removed during the drying process. The dry pharmaceutical composition may be in the form of a cake of a powder. The term "powder" refers to a substantially dry, free-flowing, particulate material having high bulk density. Spray-dried powders typically have a bulk density in the range of about 0.05-1.00 g/cc, more typically between about 0.2-0.5 g/cc. Advantageously, powders are suitable for incorporation into various non-intravenous dosage forms, including but not limited to, tablets, including rapid disintegrating tablets, caplets, capsules, sachets, solutions, suspensions, creams, gels, ointments, pessaries, suppositories, enema, drops, aerosol or dry powder inhalers, and the like. The term "cake", as compared to a powder, refers to a non-flowing, non-particulate material having a low bulk density, typically in the range of about 0.0001-0.05 g/cc. In accordance with the methods disclosed herein, a cake may be formed, for example, as a result of lyophilization or freeze-drying.

By "molecular association" is meant that at least a portion of the API is in intimate contact with the hydrophobic segment of the PVP-PLA block copolymers.

The solid pharmaceutical compositions may be in the form of, or formulated as, various dosage forms, in some embodiments. Examples include, but are not limited to tablets, caplets, capsules, sachet formulations, films, lozenges, chewing gum, pastes, ointments, sprays, aerosol inhalers, dry powder inhalers, suppositories, pessaries, etc.

By "active pharmaceutical ingredient (API)" refers to an agent that has a therapeutic or health-promoting effect when administered to a human or an animal, for example, an agent capable of treating or preventing a disease or condition. Examples of therapeutic agents include, but are not limited to, drugs, prodrugs, vitamins and supplements.

APIs contemplated herein include, for example, individual compounds of low solubility as defined herein include those drugs categorized as "slightly soluble", "very slightly soluble", "practically insoluble" and "insoluble" in USP 24, pp. 2254-2298; and those drugs categorized as requiring 100 ml or more of water to dissolve 1 g of the drug, as listed in USP 24, pp. 2299-2304.

Exemplary compounds, include, without limitation; compounds from the following classes: abortifacients, ACE inhibitors, α- and β-adrenergic agonists, α- and β-adrenergic blockers, adrenocortical suppressants, adrenocorticotropic hormones, alcohol deterrents, aldose reductase inhibitors, aldosterone antagonists, anabolics, analgesics (including narcotic and non-narcotic analgesics), anesthetics, androgens, angiotensin II receptor antagonists, anorexics, antacids, anthelminthics, antiacne agents, antiallergics, antialopecia agents, antiamebics, antiandrogens, antianginal agents, antiarrhythmics, antiarteriosclerotics, antiarthritic/antirheumatic agents, antiasthmatics, antibacterials, antibacterial adjuncts, anticholinergics, anticoagulants, anticonvulsants, antidepressants, antidiabetics, antidiarrheal agents, antidiuretics, antidotes to poison, antidyskinetics, antiezcematics, antiemetics, antiestrogens, antifibrotics, antiflatulents, antifungals, antiglaucoma agents, antigonadotropins, antigout agents, antihistaminics, antihyperactives, antihyperlipoproteinemics, antihyperphosphatemics, antihypertensives, antihyperthyroid agents, antihypotensives, antihypothyroid agents, anti-inflammatories, antimalarials, antimanics, antimethemoglobinemics, antimigraine agents, antimuscarinics, antimycobacterials, antineoplastic agents and adjuncts, antineutropenics, antiosteoporotics, antipagetics, antiparkinsonian agents, antipheochromocytoma agents, antipneumocystis agents, antiprostatic hypertrophy agents, antiprotozoals, antipruritics, antipsoriatics, antipsychotics, antipyretics, antirickettsials, antiseborrheics, antiseptics/disinfectants, antispasmodics, antisyphylitics, antithrombocythemics, antithrombotics, antitussives, antiulceratives, antiurolithics, antivenins, antiviral agents, anxiolytics, aromatase inhibitors, astringents, benzodiazepine antagonists, bone resorption inhibitors, bradycardic agents, bradykinin antagonists, bronchodilators, calcium channel blockers, calcium regulators, carbonic anhydrase inhibitors, cardiotonics, CCK antagonists, chelating agents, cholelitholytic agents, choleretics, cholinergics, cholinesterase inhibitors, cholinesterase reactivators, CNS stimulants, contraceptives, debriding agents, decongestants, depigmentors, dermatitis herpetiformis suppressants, digestive aids, diuretics, dopamine receptor agonists, dopamine receptor antagonists, ectoparasiticides, emetics, enkephalinase inhibitors, enzymes, enzyme cofactors, estrogens, expectorants, fibrinogen receptor antagonists, fluoride supplements, gastric and pancreatic secretion stimulants, gastric cytoprotectants, gastric proton pump inhibitors, gastric secretion inhibitors, gastroprokinetics, glucocorticoids, α-glucosidase inhibitors, gonad-stimulating principles, growth hormone inhibitors, growth hormone releasing factors, growth stimulants, hematinics, hematopoietics, hemolytics, hemostatics, heparin antagonists, hepatic enzyme inducers, hepatoprotectants, histamine H2 receptor antagonists, HIV protease inhibitors, HMG CoA reductase inhibitors, immunomodulators, immunosuppressants, insulin sensitizers, ion exchange resins, keratolytics, lactation stimulating hormones, laxatives/cathartics, leukotriene antagonists, LH-RH agonists, lipotropics, 5-lipoxygenase inhibitors, lupus erythematosus suppressants, matrix metalloproteinase inhibitors, mineralocorticoids, miotics, monoamine oxidase inhibitors, mucolytics, muscle relaxants, mydriatics, narcotic antagonists, neuroprotectives, nootropics, ovarian hormones, oxytocics, pepsin inhibitors, pigmentation agents, plasma volume expanders, potassium channel activators/openers, progestogens, prolactin inhibitors, prostaglandins, protease inhibitors, radio-pharmaceuticals, 5α-reductase inhibitors, respiratory stimulants, reverse transcriptase inhibitors, sedatives/hypnotics, serenics, serotonin noradrenaline reuptake inhibitors, serotonin receptor agonists, serotonin receptor antagonists, serotonin uptake inhibitors, somatostatin analogs, thrombolytics, thromboxane A2 receptor antagonists, thyroid hormones, thyrotropic hormones, tocolytics, topoisomerase I and II inhibitors, uricosurics, vasomodulators including vasodilators and vasoconstrictors, vasoprotectants, xanthine oxidase inhibitors, and combinations thereof.

Examples of APIs include, without limitation, acetaminophen, acetohexamide, acetylsalicylic acid, alclofenac, allopurinol, atropine, benzthiazide, carprofen, celecoxib, chlordiazepoxide, chlorpromazine, clonidine, codeine, codeine phosphate, codeine sulfate, deracoxib, diacerein, diclofenac, diltiazem, estradiol, etodolac, etoposide, etoricoxib, fenbufen, fendofenac, fenprofen, fentiazac, flurbiprofen, griseofulvin, haloperidol, ibuprofen, indomethacin, indoprofen, ketoprofen, lorazepam, medroxyprogesterone acetate, megestrol, methoxsalen, methylprednisone, morphine, morphine sulfate, naproxen, nicergoline, nifedipine, niflumic, oxaprozin, oxazepam, oxyphenbutazone, paclitaxel, palperidone, phenindione, phenobarbital, piroxicam, pirprofen, prednisolone, prednisone, procaine, progesterone, propofol, pyrimethamine, risperidone, rofecoxib, sulfadiazine, sulfamerazine, sulfisoxazole, sulindac, suprofen, temazepam, tiaprofenic acid, tilomisole, tolmetic, valdecoxib and ziprasidone.

Further exemplary APIs include, without limitation, Acenocoumarol, Acetyldigitoxih, Anethole, Anileridine, Benzocaine, Benzonatate, Betamethasone, Betamethasone Acetate, Betamethasone Valerate, Bisacodyl, Bromodiphenhydramine, Butamben, Chlorambucil, Chloramphenicol, Chlordiazepoxide, Chlorobutanol, Chlorocresol, Chlorpromazine, Clindamycin Palmitate, Clioquinol, Cortisone Acetate, Cyclizine Hydrochloride, Cyproheptadine Hydrochloride, Demeclocycline, Diazepam, Dibucaine, Digitoxin, Dihydroergotamine Mesylate, Dimethisterone, Disulfiram, Docusate Calcium, Docusate Sodium, Dihydrogesterone, Enalaprilat, Ergotamine Tartrate, Erythromycin, Erythromycin Estolate, Flumethasone Pivalate, Fluocinolone Acetonide, Fluorometholone, Fluphenazine Enanthate, Flurandrenolide, Guaifenesin, Halazone, Hydrocortisone, Levothyroxine Sodium, Methyclothiazide, Miconazole, Miconazole Nitrate, Nitrofurazone, Nitromersol, Oxazepam, Pentazocine, Pentobarbital, Primidone, Quinine Sulfate, Stanozolol, Sulconazole Nitrate, Sulfadimethoxine, Sulfaethidole, Sulfamethizole, Sulfamethoxazole, Sulfapyridine, Testosterone, Triazolam, Trichlormethiazide, and Trioxsalen.

In one embodiment, the dry pharmaceutical composition is reconstitutable in water or an aqueous solution into nanoparticles formed of the PVP-PLA block co-polymers and comprising the at least one API. The nanoparticles may be micelles.

In one embodiment, the dry pharmaceutical composition is freeze dried or spray dried. The composition may also be "bed dried", i.e. dried on a fluidized bed.

In one embodiment, the dry pharmaceutical composition is amorphous.

By "amorphous", is meant that the API is held is a generally disordered, i.e., non-crystalline state.

In one embodiment, the dry pharmaceutical composition is stable for at least six months at 40° C.

By "stable", in the context of a dry composition, is meant that that the dry composition may be stored for a period of time after which it is still reconstitutable for form for stable nanoparticles.

That period of time may be, e.g. 1 month, 2 months, 3 months, 4 months, 5 months, or 6 months. The temperature at which it is stable may, for example be ambient room temperature, for example about 25° C. It may also be 40° C. The composition may be stable over this period at 75% relative humidity. In some embodiments, the compositions are stable for 6 months at 40° C. and 75% relative humidity. The stable nanoparticles so reconstituted, in some embodiments, themselves stable for at least three days. The dry composition may be stable for 3 months at 25° C. The dry composition may be stable for 6 months at 25° C. The dry composition may be stable for 3 months at 40° C. The dry composition may be stable for 6 months at 60° C. The dry composition may be stable for 3 months at 25° C.

By "drug loading level" (DLL) as referred to herein is meant the weight ratio of drug to the sum of drug and polymer weight in the formulation.

In one embodiment, the dry pharmaceutical composition has a DLL of at least 10% wt/wt of the at least one API. In one embodiment, the dry pharmaceutical composition has a DLL of at least 20% wt/wt of the at least one API. In one embodiment, the dry pharmaceutical composition has a DLL of at least 30% wt/wt of the at least one API. DLL may be selected according to the API and according to requirements, and provided that requirements for administration are met. The DLL may be 5%, 7.5%, 10%, 12.5%, 15%, 17.5%, 20%, 22.5%, 25%, 27.5%, 30%, or greater than 30%.

In one embodiment, the at least one API is hydrophobic.

As used herein, "hydrophobic" means substantially immiscible with aqueous medium.

In one embodiment, the at least one API may be insoluble to sparingly soluble. In one embodiment, the at least one API has a solubility in water of 0 g/L to 33 g/L. The API may be insoluble to slightly soluble (i.e., 0 g/L to 10 g/L). In one embodiment, the at least one API has a solubility in water of 0 g/L to 14 g/L. The API may be sparingly soluble. In one embodiment, the API has a solubility in water of 10 g/L to 33 g/L.

In one embodiment, the at least one API is selected from Biopharmaceutical Classification System (BCS) class II and class IV.

In one embodiment, the at least one API comprises an analgesic.

By "analgesic" is meant any member of the group of drugs used to achieve reduction or relief of pain. Some examples include acetaminophen/paracetamol, nonsteroidal anti-inflammatory drugs (NSAIDs), COX-2 inhibitors, opioids, etc.

In one embodiment, the analgesic comprises a nonsteroidal anti-inflammatory drug (NSAID).

By "NSAID" is meant a non-narcotic drug that provides analgesic (pain-killing) and antipyretic (fever-reducing) effects, and, in higher doses, anti-inflammatory effects. Some examples include aspirin, ibuprofen and naproxen.

In one embodiment, the NSAID comprises flurbiprofen.

In one embodiment, the NSAID comprises a COX-2 inhibitor.

By "COX-2 inhibitor" is meant a drug that selectively inhibits the cyclooxygenase-2 enzyme. In one embodiment, the COX-2 inhibitor comprises celecoxib.

In one embodiment, the analgesic comprises acetaminophen.

In one embodiment, the at least one API comprises an anesthetic.

By "anesthetic" is meant one of the drugs used to prevent pain, e.g. during surgery. Non-limiting examples of non-opioid anesthetics include Barbiturates (e.g. Amobarbital, Methohexital, Thiamylal, Thiopental), Benzodiazepines (e.g., Diazepam, Lorazepam, Midazolam), Etomidate, Ketamine, and Propofol. Non-limiting examples of opioid anesthetics include Alfentanil, Fentanyl, Remifentanil, Sufentanil, Buprenorphine, Butorphanol, diacetyl morphine, Hydromorphone, Levorphanol, Meperidine, Methadone, Morphine, Nalbuphine, Oxycodone, Oxymorphone, and Pentazocine.

In one embodiment, the anesthetic comprises propofol.

In one embodiment, the dry pharmaceutical composition is orally administrable.

In one embodiment, the dry pharmaceutical composition is reconstitutable in water to form an essentially clear liquid comprising nanoparticles formed of the PVP-PLA block copolymers and comprising the at least one API.

In one embodiment, the essentially clear liquid comprises at least 20 g/L of the at least one API. In one embodiment, the essentially clear liquid comprises at least 30 g/L of the at least one API. In one embodiment, the essentially clear liquid comprises at least 40 g/L of the at least one API. In one embodiment, the essentially clear liquid comprises at least 50 g/L of the at least one API.

In one embodiment the dry pharmaceutical composition provides a pharmaceutically effective plasma level of the at least one API for at least 4 hours. In one embodiment the dry pharmaceutical composition provides a pharmaceutically effective plasma level of the at least one API for at least 6 fours. In one embodiment the dry pharmaceutical composition provides a pharmaceutically effective plasma level of the at least one API for at least 8 fours. In one embodiment the dry pharmaceutical composition provides a pharmaceutically effective plasma level of the at least one API for at least 12 hours.

In some embodiments, the dry pharmaceutical composition comprises at least two APIs, wherein the block copolymers are as defined as above under Group 2. In some embodiments, the at least two APIs comprise flurbiprofen and celecoxib.

In some embodiments, the dry pharmaceutical composition comprises at least three APIs, wherein the block copolymers are as defined as above under Group 3. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol In some embodiments, the dry pharmaceutical composition comprises at least three APIs, wherein the block copolymers are as defined as above under Group 4. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol Liquid Pharmaceutical Composition In one aspect, there is provided a liquid pharmaceutical composition comprising a nanoparticles formed of the above-described PVP-PLA block copolymers and comprising at least one active pharmaceutical ingredient (API).

In one embodiment, the liquid pharmaceutical composition is an essentially clear liquid.

In one embodiment, the essentially clear liquid is filterable through a sterilization filter. A "sterilization filter" will be understood as a filter that achieves filtration required to meet sterility requirements. For example, such a filter may have a pore size of 0.45 microns or 0.2 microns.

In one embodiment, the essentially clear liquid is parenterally deliverable. In one embodiment, the essentially clear liquid is injectable. In one embodiment, the essentially clear liquid is deliverable by intravenous. In one embodiment, the essentially clear liquid is deliverable by infusion. The essentially clear liquid may be deliverable parenterally, intravenously, by infusion, intraocularly, intrathecally, intramuscularly, intraperitoneally, or intraspinally.

In one embodiment, the liquid pharmaceutical composition is stable for at least three days at 25° C.

In one embodiment, the liquid pharmaceutical composition provides a pharmaceutically effective plasma level of the at least one API within 2 minutes. The liquid pharmaceutical composition may provide a pharmaceutically effective plasma level within 1 minute, 2 minutes, 5 minutes, 10 minutes, 20 minutes, or 30 minutes.

By "pharmaceutically effective plasma level" is meant an amount of the API that, when in plasma, is sufficient to achieve desired therapeutic efficacy. This level can vary depending, for example, on the API, the disease, disorder, and/or symptoms of the disease or disorder, severity of the disease, disorder, and/or symptoms of the disease or disorder, the age, weight, and/or health of the patient to be treated.

In one embodiment a pharmaceutically effective plasma level of the API is maintained for at least 4 fours. In one embodiment a pharmaceutically effective plasma level of the at least one API is maintained for at least 6 fours. In one embodiment a pharmaceutically effective plasma level of the at least one API is maintained for at least 8 fours. In one embodiment a pharmaceutically effective plasma level of the at least one API is maintained for at least 12 hours.

In one embodiment, the liquid pharmaceutical composition further comprising a pharmaceutically acceptable diluent, excipient, or carrier. "Pharmaceutically acceptable" refers to additives which are nontoxic when administered to a patient in an amount sufficient to provide a therapeutic effect of the API, and which do not destroy the biological activity of the at least one API. "Diluent, excipient, or carrier" will be understood as an additive having substantially no pharmacological activity of its own.

In one embodiment, the at least one API is hydrophobic.

In one embodiment, the at least one API may be insoluble to sparingly soluble. In one embodiment, the at least one API has a solubility in water of 0 g/L to 33 g/L. The API may be insoluble to slightly soluble (i.e., 0 g/L to 10 g/L). In one embodiment, the API has a solubility in water of 0 g/L to 14 g/L. The API may be sparingly soluble. In one embodiment, the API has a solubility in water of 10 g/L to 33 g/L.

In one embodiment, the at least one API is selected from Biopharmaceutical Classification System (BCS) class II and class IV.

In one embodiment, the at least one API comprises an analgesic.

In one embodiment, the analgesic comprises a nonsteroidal anti-inflammatory drug (NSAID).

In one embodiment, the NSAID comprises flurbiprofen.

In one embodiment, the NSAID comprises a COX-2 inhibitor.

In one embodiment, the COX-2 inhibitor comprises celecoxib.

In one embodiment, the analgesic comprises acetaminophen.

In one embodiment, the at least one API comprises an anesthetic.

In one embodiment, the anesthetic comprises propofol.

In one embodiment, the liquid pharmaceutical composition comprises at least 20 g/L of the at least one API. In one embodiment, the liquid pharmaceutical composition comprises at least 30 g/L of the at least one API. In one embodiment, the liquid pharmaceutical composition comprises at least 40 g/L of the at least one API. In one embodiment, the liquid pharmaceutical composition comprises at least 50 g/L of the at least one API.

In some embodiments, the liquid pharmaceutical composition comprises at least two APIs, wherein the block copolymers are as defined as above under Group 2. In some embodiments, the at least two APIs comprise flurbiprofen and celecoxib.

In some embodiments, the liquid pharmaceutical composition comprises at least three APIs, wherein the block copolymers are as defined as above under Group 3. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol In some embodiments, the liquid pharmaceutical composition comprises at least three APIs, wherein the block copolymers are as defined as above under Group 4. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol Haemolysis In one aspect, the above-described block copolymers may find application in mitigation of haemolytic effects.

In one aspect, the above-described block copolymers may find application in mitigation of haemolytic activity of a cargo molecule. The cargo may be a small or large molecule, such as an API.

By "haemolytic activity" or "haemolytic effects" will be understood the propensity for a particular molecule or formulation to cause haemolysis, i.e. lysis of red blood cells (RBCs). These may be mammalian RBCs, e.g., human red blood cells. The propensity to cause haemolysis may be may be determined in vitro, for example, using RBCs derived from blood, for example, derived from whole human blood. An example in vitro test is the method followed in Example 5. For example suspended RBCs isolated from whole human blood may be mixed with non-formulated cargo molecules or test formulations comprising the cargo molecule at a given final concentration with respect to the cargo molecule incubated at 37° C. for 60 minutes, and centrifuged to remove intact RBCs. Absorbance at 540 nm may then be measured and compared against control samples, e.g. for 0 and 100% haemolysis. The in vitro test may be one established to provide an indication of the haemolytic potential of the cargo molecule or the haemo-protective potential of the formulation in vivo.

Where mitigation of haemolysis is mentioned for a particular formulated cargo molecule (i.e. formulated with PVP-PLA block co-polymer), it will be understood that this means that there is a degree of protection afforded by the formulation (the haemo-protective potential) to RBCs against cargo molecule induced haemolysis which protection may be expressed as a percentage of that caused by the cargo molecule in an unformulated or conventionally formulated state. For example, the degree of haemo-protection afforded to RBCs by a PVP-PLA block co-polymer formulation of FLU against the haemolytic activity of unformulated or conventionally formulated FLU may be calculated as:

100%−((percent haemolysis observed for PVP-PLA FLU formulation)+(percent haemolysis observed for unformulated or conventionally formulated FLU)×100%).

Thus, in an example scenario in which unformulated FLU at a final concentration 5 g/L causes 90% haemolysis and PVP-PLA FLU causes 7% (i.e. similar to that of the negative control), the degree of protection would be 100%−(7/90×100%)=92%.

By "unformulated state" will be understood the molecule in the absence of the PVP-PLA block copolymers described herein. Likewise, "conventionally formulated" will be understood as some other formulation of the molecule that does not include the PVP-PLA block copolymers describe here.

In one embodiment, there is provided a use of the above-described block copolymers for mitigation of haemolytic activity of a cargo molecule, such as an API. In one embodiment there is provided a use of the above-described block copolymers for mitigation of the heamolytic potential of a cargo molecule, such as an API, to negative control levels. In some embodiments, the negative control levels will be understood to be the degree of haemolysis caused by addition of the negative control solution. An example is the negative control described in Example 5. In one embodiment, the block copolymers may be as defined for Group 1. In one embodiment, the block copolymers may be as defined for Group 2. In one embodiment, the block copolymers may be as defined for Group 3. In one embodiment, the block copolymers may be as defined for Group 4. In one embodiment, the degree of protection, as defined above, is at least 50%. In one embodiment, the degree of protection is at least 60%. In one embodiment, the degree of protection is at least 70%. In one embodiment, the degree of protection is at least 80%. In one embodiment, the degree of protection it at least 90%. In one embodiment, the degree of protection it at least 92%. In one embodiment, the degree of protection it at least 95%.

In one embodiment, there is provided a block copolymer, as described above, for use in mitigation of haemolytic activity of a cargo molecule, such as an API. In one embodiment there is provided a block copolymer for mitigation of the heamolytic potential of a cargo molecule, such as an API, to negative control levels. In some embodiments, the negative control levels will be understood to be the degree of haemolysis caused by addition of the negative control solution. An example is the negative control described in Example 5. In one embodiment, the block copolymers may be as defined for Group 1. In one embodiment, the block copolymers may be as defined for Group 2. In one embodiment, the block copolymers may be as defined for Group 3. In one embodiment, the block copolymers may be as defined for Group 4. In one embodiment, the degree of protection, as defined above, is at least 50%. In one embodiment, the degree of protection is at least 60%. In one embodiment, the degree of protection is at least 70%. In one embodiment, the degree of protection is at least 80%. In one embodiment, the degree of protection it at least 90%. In one embodiment, the degree of protection it at least 92%. In one embodiment, the degree of protection it at least 95%.

In one embodiment, there is provided a method of mitigating haemolytic activity of a cargo molecule, such as an API, the method comprising the steps of: mixing block copolymers described above with the API to form a liquid pharmaceutical composition, said liquid pharmaceutical composition exhibiting reduced or no hemolytic activity compared to the API in an non-formulated stated. In one embodiment, the block copolymers may be as defined for Group 1. In one embodiment, the block copolymers may be as defined for Group 2. In one embodiment, the block copolymers may be as defined for Group 3. In one embodiment, the block copolymers may be as defined for Group 4. In one embodiment, the degree of protection, as defined above, is at least 50%. In one embodiment, the degree of protection is at least 60%. In one embodiment, the degree of protection is at least 70%. In one embodiment, the degree of protection is at least 80%. In one embodiment, the degree of protection it at least 90%. In one embodiment, the degree of protection it at least 92%. In one embodiment, the degree of protection it at least 95%.

In one embodiment, the above-described dry pharmaceutical composition exhibits mitigated haemolytic effects for the API, when reconstituted to form a liquid pharmaceutical composition. In one embodiment, the above-described dry pharmaceutical composition exhibits mitigated haemolytic activity for the API, when reconstituted to form a liquid pharmaceutical composition, e.g. compared to the API alone. In one embodiment, the block copolymers may be as defined for Group 1. In one embodiment, the block copolymers may be as defined for Group 2. In one embodiment, the block copolymers may be as defined for Group 3. In one embodiment, the block copolymers may be as defined for Group 4. In one embodiment, the degree of protection, as defined above, is at least 50%. In one embodiment, the degree of protection is at least 60%. In one embodiment, the degree of protection is at least 70%. In one embodiment, the degree of protection is at least 80%. In one embodiment, the degree of protection it at least 90%. In one embodiment, the degree of protection it at least 92%. In one embodiment, the degree of protection it at least 95%.

In one embodiment, the above-described liquid formulation exhibits mitigated haemolytic activity for the API. In one embodiment, the above-described liquid formulation exhibits mitigated haemolytic activity for the API, e.g. compared to the API alone. In one embodiment, the block copolymers may be as defined for Group 1. In one embodiment, the block copolymers may be as defined for Group 2. In one embodiment, the block copolymers may be as defined for Group 3. In one embodiment, the block copolymers may be as defined for Group 4. In one embodiment, the degree of protection, as defined above, is at least 50%. In one embodiment, the degree of protection is at least 60%. In one embodiment, the degree of protection is at least 70%. In one embodiment, the degree of protection is at least 80%. In one embodiment, the degree of protection it at least 90%. In one embodiment, the degree of protection it at least 92%. In one embodiment, the degree of protection it at least 95%.

In one embodiment of the above, the API comprises celecoxib. In some of these embodiments, the DLL of the celecoxib is 5% to 15%. In one embodiment, the DLL of the celecoxib is about 10%.

In one embodiment of the above, the API comprises acetaminophen. In some of these embodiments, the DLL of the acetaminophen is 13% to 23%. In one embodiment, the DLL of the acetaminophen is about 18%.

In the above, the API may be one that causes haemolysis in an unformulated or conventionally formulated state. In some embodiments, the level of haemolysis caused by the API may be a level that precludes its administration to a subject. The API may be one that is known to cause haemolysis, e.g. when administered (e.g. parenterally) to a subject in an unformulated stated. The API may be an API that, in its unformulated state, causes more than 10% haemolysis of RBCs in the test set forth in Example 5. It will be understood that an API that "causes haemolysis" may do so at a desired level of administration in an unformulated or conventionally formulated state, and not necessarily at all (or to the same extend) at other levels in an unformulated or conventionally formulated state. One example API that causes haemolysis in an unformulated stated is flurbiprofen.

In some embodiments of the above, the API is flurbiprofen. In some of these embodiments, the DLL of the flurbiprofen is 15 to 25%. In one embodiment, the DLL of the flurbiprofen is about 20%.

Method of Forming Pharmaceutical Compositions

In one aspect, there is provide a method of forming a pharmaceutical composition comprising mixing the above-described block copolymers with at least one API to form nanoparticles comprising the at least one API.

In one embodiment, the at least one API comprises at least two APIs, and the block co-polymers are as defined above under Group 2. In some embodiments, the at least two APIs comprise flurbiprofen and celecoxib.

In one embodiment, the at least one API comprises at least three APIs, and the block co-polymers are as defined above under Group 3. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol.

In one embodiment, the at least one API comprises at least three APIs, and the block co-polymers are as defined above under Group 4. In some embodiments the at least three different APIs comprise at least three of flurbiprofen, celecoxib, acetaminophen, and propofol. In some embodiments, the at least three different APIs comprise all four of flurbiprofen, celecoxib, acetaminophen, and propofol.

In one embodiment, the above-described methods may comprise a step of drying the pharmaceutical composition.

In some embodiments involving a plurality of APIs, the plurality of APIs may be mixed together with the copolymers.

Alternative, the method may comprise separately mixing each API with an amount of the block copolymer prior to combining them. These embodiments may comprise an additional step of incubating the two populations of nanoparticles so-formed together for sufficient time for an exchange of APIs to take place as the mixture equilibrates.

Delivery Methods, Uses, and Kits

In one aspect, there is provided a method of delivering at least one active pharmaceutical ingredient (API) to a subject in need thereof, comprising administering the above-described dry pharmaceutical composition to the subject.

In one embodiment, the administering is orally administering.

In one aspect, there is provided a method of delivering at least one active pharmaceutical ingredient (API) to a subject in need thereof, comprising administering the above-described liquid pharmaceutical composition to the subject.

In one embodiment, said administering comprises injecting, parenterally administering, intravenously administrating, infusing, intraocularly administering, intrathecally administering, intramuscularly administering, intraperitoneally administering, or intraspinally administering.

In one embodiment, the pharmaceutically effective plasma level is maintained for at least 4 hours. In one embodiment, the pharmaceutically effective plasma level is maintained for at least 6 hours. In one embodiment, the pharmaceutically effective plasma level is maintained for at least 8 hours. In one embodiment, the pharmaceutically effective plasma level is maintained for at least 12 hours.

In one embodiment, the subject is in pain, and the at least one API comprises an analgesic. In one embodiment, the analgesic comprises an NSAID. In one embodiment, the NSAID i comprises s flurbiprofen. In one embodiment, the NSAID comprises celecoxib.

In one embodiment, the analgesic comprises acetaminophen.

In one embodiment, the subject is in need of anesthesia and the at least one API is an anesthetic. In one embodiment, the anesthetic is propofol.

In one aspect, there is provided the above-described dry pharmaceutical composition or the above-described liquid pharmaceutical composition for use in delivery of at least one active pharmaceutical ingredient (API) to a subject.

In one embodiment, the composition is for use in treatment of pain in the subject, wherein the at least one API comprises an analgesic.

In one embodiment, the analgesic comprises an NSAID.
In one embodiment, the NSAID comprises flurbiprofen.
In one embodiment, the NSAID comprises celecoxib.
In one embodiment, the analgesic comprises acetaminophen.

In one embodiment, the composition is for use in providing anesthesia to the subject, wherein the API comprises an anesthetic.

In one embodiment, the anesthetic is propofol.

In one aspect, there is provided a kit comprising the above-described dry pharmaceutical composition or the above-described liquid pharmaceutical composition, and instructions for use in delivery of at least one active pharmaceutical ingredient (API) to a subject.

In one aspect, there is provided a kit comprising the above-described dry pharmaceutical composition or the above-described liquid pharmaceutical composition, and instructions for use in delivery of at least one active pharmaceutical ingredient (API) for treatment of pain in a subject.

In one embodiment the at least one API comprises flurbiprofen, celecoxib, or acetaminophen.

In one aspect, there is provided a kit comprising the above-described dry pharmaceutical composition or the above-described liquid pharmaceutical composition, and instructions for use in delivery of at least one active pharmaceutical ingredient (API) for providing anesthesia to a subject.

In one embodiment, the at least one API comprises propofol.

Production Methods

In another aspect, there is provided a method of preparing PVP-PLA block copolymers as defined in Formula I:

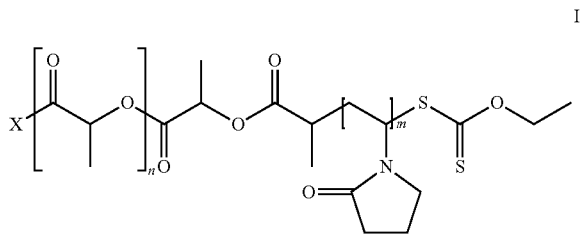

I wherein: x is an initiator alcohol having a boiling point greater than 145° C., n is, on average, from 20 and 40, and m is, on average, from 10 and 40, wherein the block copolymers have a number average molecular weight (Mn) of at least 3000 Da, the method comprising: initiating polymerization of D,L-Lactide from the initiator alcohol x to form poly(lactic acid) (PLA), adding a xanthate to the PLA to form a PLA macroinitiator, and polymerizing NVP, by controlled polymerization, onto the PLA macroinitiator to form the block copolymer compound of Formula I.

In one embodiment, the controlled polymerization is controlled radical polymerization.

In one embodiment, the PVP-PLA block copolymer are as defined herein.

In one embodiment, the PVP-PLA block copolymer are as defined above under Group 1.

In one embodiment, the PVP-PLA block copolymer are as defined above under Group 2.

In one embodiment, the PVP-PLA block copolymer are as defined above under Group 3.

In one embodiment, the PVP-PLA block copolymer are as defined above under Group 4.

In one embodiment, the polymerization of the D,L-Lactide is by an organocatalytic coordination-insertion polymerization. In one embodiment, the catalyst for the polymerization of the D,L-Lactide is 4-dimethylaminopyridine (DMAP). In one embodiment, the polymerization of the D,L-Lactide takes place at a temperature of at least 60° C. to 90° C. In one embodiment, the polymerization of the D,L-Lactide takes place for at least 24 hours. In one embodiment, the polymerizing of the D,L-Lactide takes place for at least 48 hours. In one embodiment, the polymerizing of the D,L-Lactide takes place for at least 60 hours.

In one embodiment, the polymerization of the D,L-Lactide is by an organocatalytic coordination-insertion polymerization. In one embodiment, the catalyst for the polymerization of the D,L-Lactide is or stannous octoate (Sn(Oct)$_2$). In one embodiment, the polymerization of the D,L-Lactide takes place at a temperature of at least 135° C. to 160° C. In one embodiment, the polymerizing of the D,L-Lactide takes place for at least 24 hours. In one embodiment, the polymerizing of the D,L-Lactide takes place for at least 48 hours. In one embodiment, the polymerizing of the D,L-Lactide takes place for at least 60 hours.

In one embodiment, the catalyst for the polymerizing of the NVP is azobisisobutyronitrile (AIBN). In one embodiment, the polymerizing of the NVP takes place at a temperature of at least 70° C. to 90° C. In one embodiment, the polymerizing of the NVP takes place for at least 24 hours. In one embodiment, the polymerizing of the NVP takes place for at least 48 hours. In one embodiment, the polymerizing of the NVP takes place for at least 60 hours.

In one embodiment, the method further comprises removing the xanthate.

In one embodiment, the method further comprises adding a functional moiety.

By "functional moiety" is meant a molecular modification or addition that provides a desired functional activity or reactivity. The "functional moiety" may be a "targeting moiety" designed to target the ensuing nanoparticles formed of the block copolymers to a particular cell type, e.g. by targeting a particularly cell surface protein or receptor. The addition of a functional moiety may result in nanoparticles that are functionalized or decorated. For example, functional moieties may include a dye, a tracer, or a terminal functional group.

In one embodiment, the functional moiety comprises a targeting moiety.

By "targeting moiety" is meant any chemical compound, including, e.g., a peptide or nucleic acid, that imparts a targeting function to micelles formed of the block-copolymers to which it is attached. Targeting moieties may, for example, have affinity for particularly cell surface proteins or receptors. This may be characteristic of a particular organ or cell type. In one embodiment, the targeting moiety comprises albumin, folate, or an aptamer. By "aptamer" is meant a single-stranded DNA or RNA (ssDNA or ssRNA) molecules that can bind to a pre-selected target, such as a protein or peptide, with high affinity and specificity.

EXAMPLES

Introduction to Examples 1 & 2

PVP-PLA technology can be used for formulation of drugs, e.g. with dose limiting solubility in water. The technology has the ability to form micelles independently of the pH when the polymer concentration in water is above the critical micellar concentration (CMC). The micelles are disrupted when the polymer concentration decreases below the CMC. Following this principle, a formulation comprising reconstituted PVP-PLA micelles will begin releasing its drug content, e.g., upon injection into blood. PVP-PLA technology remains challenging because of inefficient synthesis and polydispersity, and because of lack of flexible delivery platforms having the ability to formulate a variety of drugs and/or entrap them at sufficiently high concentration (i.e., drug loading level or DLL).

New PVP-PLA copolymers or methods of production were sought that would provide relevant physical or chemical properties, desired yield, efficiency of synthesis, low polydispersity, ease production, desired flexibility in formulating a range of drugs, and/or high DLL. Two main approaches were used to attempt to improve the synthesis of the PVP-PLA block copolymer.

In the first approach, the PVP-PLA was prepared using a polyvinylpyrrolidone with a terminal hydroxyl group (termed "PVP-OH") as a macro initiator followed by (i) an organometallic coordination-insertion polymerization (Scheme 1A), (ii) an anionic polymerization (Scheme 1B), or (iii) an organocatalytic coordination-insertion polymerization (see Scheme 1C) of the D,L-Lactide [1]. This approach will be subsequently referred to as the "PVP-OH approach". Scheme 1 shows each synthesis route for one type of catalyst, one solvent, and one specific temperature. However, each synthesis route was tested in two or three different solvents, using two types of catalysts and at two different temperatures. In total, 8 to 12 syntheses per route were carried out.

Scheme 1

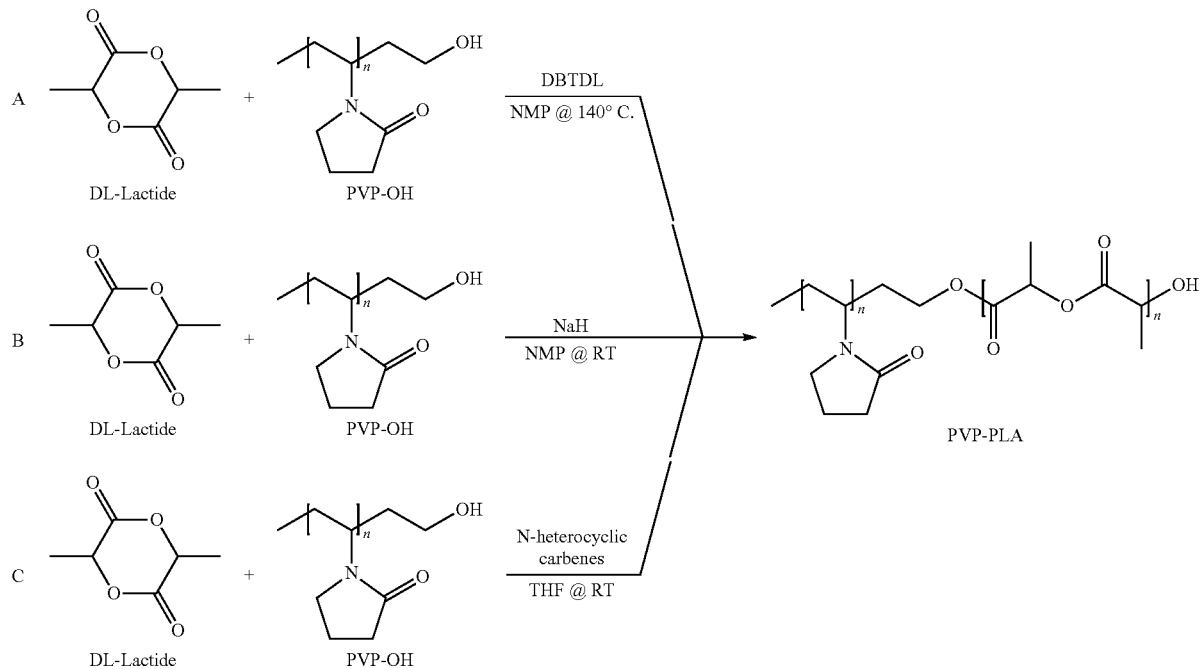

In the second approach, the PVP-PLA was produced starting with the preparation of the poly(D,L-lactide) with a terminal hydroxyl group (termed "PLA-OH") and the PLA-OH was used as a macro chain transfer agent to polymerize the N-vinyl-2-pyrrolidinone (NVP). The preparation of the PLA-OH was performed following either (i) an organocatalytic coordination-insertion polymerization (see Scheme 2A-1) or (ii) an organometallic coordination-insertion polymerization (see Schemes 2B-1 and 2C-1). The PLA-OH obtained was converted to a macro chain transfer agent by substituting the terminal hydroxyl group by an O-ethyl xanthate group. The substitution of the hydroxyl group required two steps as illustrated in Scheme 2. After the substitution, the resulting macro chain transfer agent of PLA was used to polymerize the NVP (see schemes 2A-4, 2B-4 and 2C-4). This second approach will be subsequently referred to as the "PLA-OH approach".

Scheme 2

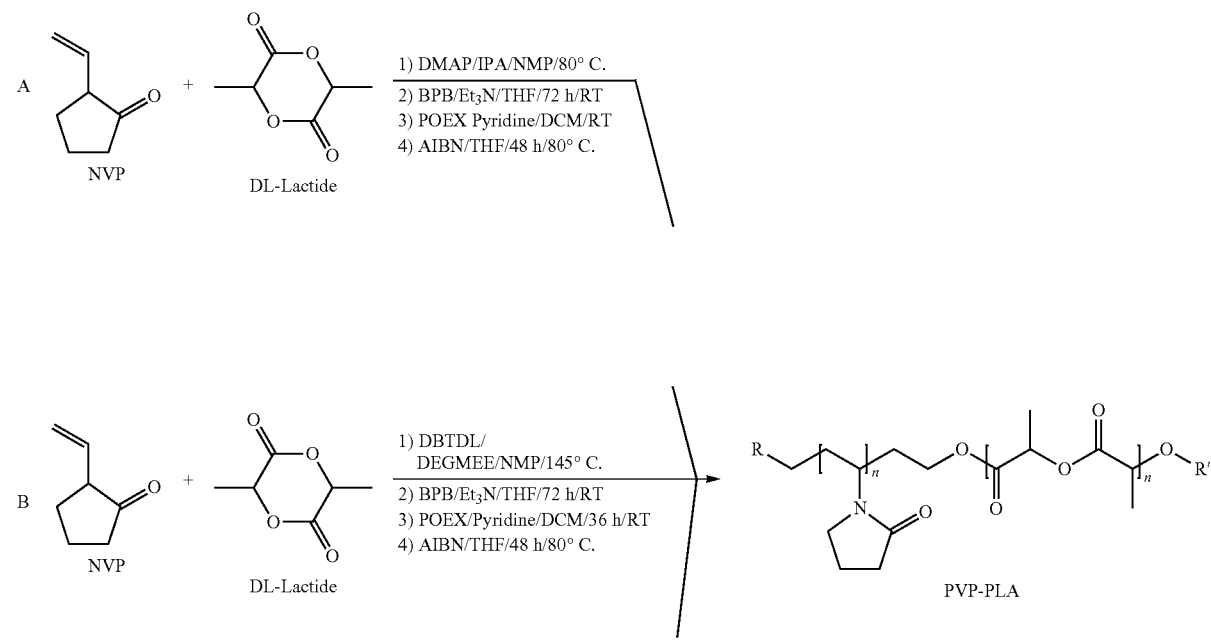

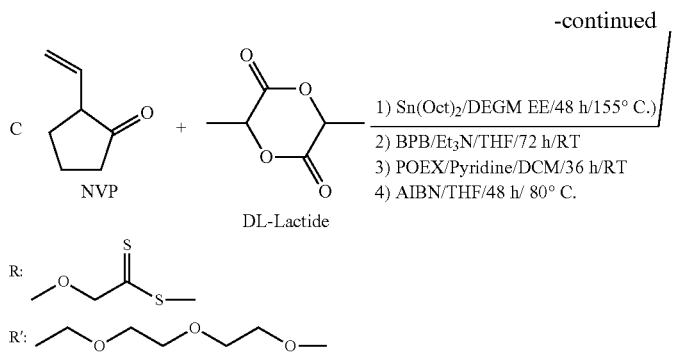

1) Sn(Oct)₂/DEGM EE/48 h/155° C.
2) BPB/Et₃N/THF/72 h/RT
3) POEX/Pyridine/DCM/36 h/RT
4) AIBN/THF/48 h/ 80° C.

R: [structure]

R': [structure]

Example 1: The PVP-OH Approach

PVP-PLA was obtained by using PVP-OH as a macro initiator for the polymerization of D,L-lactide. PVP-OH used during this project is a commercial polymer from Polysciences (Cat. Number 16693, Lot Number 652063 and Mw 2500). However, PVP-OH can also be made by a radical polymerization of N-vinyl-2-pyrrolidinone (NVP) in the presence of 2-isopropoxyethanol (IPE) or mercaptoethanol or functionalized disulfides as chain transfer agent (CTA) [2, 3]. Independently of the CTA, most of the PVP chains obtained had one or two chain transfer agents as a terminal group. The obtained polymer was a mixture of OH-PVP-OH, PVP-OH and PVP at different proportions. However, the proportion of PVP-OH can be increased by the type of chain transfer agent used and the experimental conditions of the polymerization. The synthesis of PVP-OH with a controlled molecular weight and polydispersity index (PDI) remains challenging.

Organometallic Coordination-Insertion Polymerization of PVP-PLA

The organometallic coordination-insertion polymerization of PVP-PLA was performed in the presence of either dibutyl tin dilaurate (DBTDL) or dibutyl tin oxide (DBTO) as catalyst. Scheme 3 shows the synthesis route for the preparation of PVP-PLA using DBTDL as catalyst in different experimental conditions and solvents.

Scheme 3

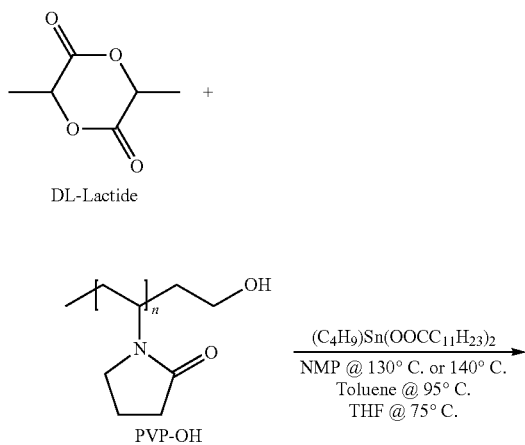

(C₄H₉)Sn(OOCC₁₁H₂₃)₂
NMP @ 130° C. or 140° C.
Toluene @ 95° C.
THF @ 75° C.

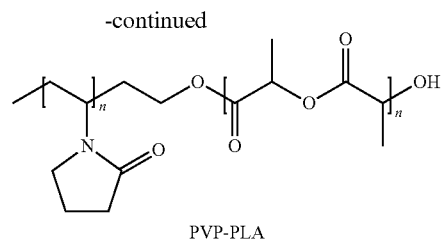

PVP-PLA

Procedure of the Synthesis

A required amount of PVP-OH (previously dried using toluene as solvent) was dissolved in N-Methyl-2-pyrrolidone (NMP) and then a certain quantity of dibutyl tin dilaurate was added to the mixture. After the dispersion of the DBTDL, a required ratio of D,L-lactide (the compound is previously dried after purification by recrystallization from ethyl acetate) was added to the mixture. The obtained reaction mixture solution was stirred under argon atmosphere for 1 h and then put at 130° C. and kept under argon atmosphere for another 4 hrs. The polymerization was left for 20 hrs more and then cooled to room temperature before the precipitation in diethyl ether. A white solid product was obtained after precipitation.

The cooled solution was added dropwise to a certain amount of diethyl ether and then the product was collected by filtration. The product obtained was washed with three portions of diethyl ether before being dried overnight at 40° C. Table 1 shows the amount of raw materials used for the preparation of PVP-PLA in the presence of DTBL as catalyst and NMP as solvent.

TABLE 1

| Compounds | Mw (g/mol) | Mass used (g) | Mole | Density (g/mL) |
|---|---|---|---|---|
| DL-Lactide | 144.13 | 32.00 | 0.2220 | N/A |
| PVP-OH | 2500 | 37.00 | 0.0148 | N/A |
| DBTDL | 631.56 | 9.47 | 0.0150 | 1.066 |
| NMP | 99.13 | 257.00 | 2.5926 | 1.028 |

Other Experimental Conditions

The synthesis of PVP-PLA by organometallic coordination-insertion polymerization was repeated under various experimental conditions. Table 2 illustrates all the conditions and the amount of raw materials used to generate the block copolymer of PVP-PLA.

TABLE 2

| Compounds | Mw (g/mol) | Mass used (g) | Mole | Density (g/mL) | Temperature (° C.) | Time (h) |
|---|---|---|---|---|---|---|
| DL-Lactide | 144.13 | 32.00 | 0.2220 | N/A | 140 | 4 |
| PVP-OH | 2500 | 37.00 | 0.0148 | N/A | | |
| DBTDL | 631.56 | 9.47 | 0.0150 | 1.066 | | |
| NMP | 99.13 | 257.00 | 2.5926 | 1.028 | | |
| DL-Lactide | 144.13 | 16.00 | 0.1110 | N/A | 95 | 24 |
| PVP-OH | 2500 | 19.00 | 0.0076 | N/A | | |
| DBTDL | 631.56 | 4.74 | 0.0075 | 1.066 | | |
| Toluene | 92.14 | 130.00 | 2.5926 | 0.865 | | |
| DL-Lactide | 144.13 | 16.00 | 0.1110 | N/A | 75 | 24 |
| PVP-OH | 2500 | 19.00 | 0.0076 | N/A | | |
| DBTDL | 631.56 | 4.74 | 0.0075 | 1.066 | | |
| THF | 72.11 | 222.25 | 3.0821 | 0.889 | | |
| DL-Lactide | 144.13 | 15.00 | 0.1041 | N/A | 120 | 36 |
| PVP-OH | 2500 | 15.00 | 0.0060 | N/A | | |
| DBTO | 248.94 | 0.50 | 0.0002 | N/A | | |
| NMP | 99.13 | 257.00 | 2.5926 | 1.028 | | |

Results

Independent of the experimental conditions used, a very viscous product was obtained for each case. However, the results from testing or different techniques show that the D,L-Lactide did not react with the PVP-OH as expected. Without being bound by theory, the limited proportion of PVP-OH may be the main cause of those results. As mentioned above, it is a challenge to obtain PVP-OH in a proportion greater than 50% [3]. The product obtained was usually a mixture of HO-PVP-OH, PVP-OH and PVP. In order to understand the results obtained, it was decided to repeat the synthesis with DBTDL and DBTO in NMP at 130° C. and 120° C., respectively. However, the PVP-OH was replaced by a commercial poly(ethylene glycol) monomethyl ether (MePEG-OH) from Sigma Aldrich. The MePEG-OH (Cat Number 202509, lot Number MKBS5550V and Mw 2000) contains more than 90% of one terminal hydroxyl group in comparison to 50% for PVP-OH. The results obtained with MePEG-OH were much better than with PVP-OH except in the case of MePEG-OH—the D,L-Lactide reacted with MePEG-OH but the yield was less than 25%. Moreover, the Mn was much smaller than expected. Based on these results, the organometallic coordination-insertion polymerization from PVP-OH was not a sufficiently good method to prepare PVP-PLA for cost-effective development of potent drug products that are marketable.

Anionic Polymerization of PVP-PLA

The anionic polymerization of PVP-PLA was performed in the presence of either the sodium hydride (NaH) or potassium hydride (KH) as catalyst. Scheme 4 shows the resulting synthetic route for the preparation of PVP-PLA using NaH as catalyst in different experimental conditions.

Scheme 4

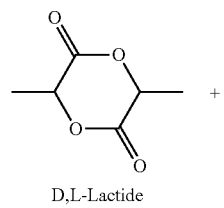

D,L-Lactide

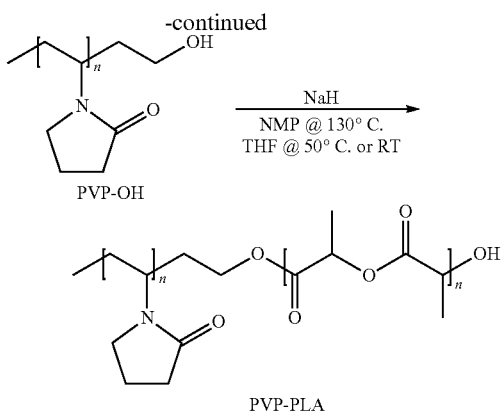

PVP-PLA

Procedure of the Synthesis

A required amount of PVP-OH was dissolved in N-Methyl-2-pyrrolidone (NMP) and then a certain quantity of NaH was added to the mixture. After the dispersion of the NaH, a required ratio of D,L-lactide (previously dried and purified by recrystallization from ethyl acetate) was added to the mixture. The mixture obtained was stirred under nitrogen atmosphere for 1 h and then put at 130° C. and kept under nitrogen atmosphere for another 4 hrs. The polymerization was left for 20 hrs and then cooled to room temperature before precipitation in diethyl ether.

The cooled solution was added dropwise to an amount of diethyl ether and then the product was collected by filtration. The product obtained was washed with three portions of diethyl ether before being dried overnight at 40° C. Table 3 shows the amounts of raw materials used for the preparation of PVP-PLA in the presence of NaH as catalyst and NMP as solvent.

TABLE 3

| Compounds | Mw (g/mol) | Mass used (g) | Mole | Density (g/mL) |
|---|---|---|---|---|
| DL-Lactide | 144.13 | 32.00 | 0.2220 | N/A |
| PVP-OH | 2500 | 37.00 | 0.0148 | N/A |
| NaH | 24.00 | 0.600 | 0.0150 | 0.600 |
| NMP | 99.13 | 257.00 | 2.5926 | 1.028 |

Other Experimental Conditions

As performed in the previous synthetic method, the synthesis of PVP-PLA by anionic polymerization was repeated under various experimental conditions. Table 4 illustrates all the conditions and the amounts of raw materials used to generate the PVP-PLA.

TABLE 4

| Compounds | Mw (g/mol) | Mass used (g) | Mole | Density (g/mL) | Temperature (° C.) | Time (h) |
|---|---|---|---|---|---|---|
| DL-Lactide | 144.13 | 32.00 | 0.2220 | N/A | RT | 24 |
| PVP-OH | 2500 | 37.00 | 0.0148 | N/A | | |
| NaH | 24.00 | 0.600 | 0.0150 | 0.600 | | |
| THF | 72.11 | 222.25 | 3.0821 | 0.889 | | |
| DL-Lactide | 144.13 | 32.00 | 0.2220 | N/A | 50 | 24 |
| PVP-OH | 2500 | 37.00 | 0.0148 | N/A | | |

TABLE 4-continued

| Compounds | Mw (g/mol) | Mass used (g) | Mole | Density (g/mL) | Temperature (° C.) | Time (h) |
|---|---|---|---|---|---|---|
| NaH | 24.00 | 0.600 | 0.0150 | 0.600 | | |
| THF | 72.11 | 222.25 | 3.0821 | 0.889 | | |
| DL-Lactide | 144.13 | 32.00 | 0.2220 | N/A | RT | 24 |
| PVP-OH | 2500 | 37.00 | 0.0148 | N/A | | |
| KH | 40.11 | 1.00 | 0.0250 | N/A | | |
| THF | 72.11 | 222.25 | 3.0821 | 0.889 | | |
| DL-Lactide | 144.13 | 32.00 | 0.2220 | N/A | 50 | 24 |
| PVP-OH | 2500 | 37.00 | 0.0148 | N/A | | |
| KH | 40.11 | 1.00 | 0.0250 | N/A | | |
| THF | 72.11 | 222.25 | 3.0821 | 0.889 | | |
| DL-Lactide | 144.13 | 32.00 | 0.2220 | N/A | 130 | 24 |
| PVP-OH | 2500 | 37.00 | 0.0148 | N/A | | |
| KH | 40.11 | 1.00 | 0.0250 | N/A | | |
| NMP | 99.13 | 257.00 | 2.5926 | 1.028 | | |

Results

Independent of the experimental conditions used, a white solid was obtained in each case. The results from different techniques show that the D,L-Lactide reacted partially with the PVP-OH only in the case of the synthesis with NaH in THF at room temperature. The yield obtained for this synthesis was always below 30%. These results suggest that the PVP-OH sodium salt is not as efficient as a macro initiator since 50% yield was expected instead of 30% [3]. The method also led to the production of a very small proportion of a homopolymer of PLA-OH, but enough to generate a bimodal micelle size distribution. The bimodal micelle size distribution is not suitable for parenteral formulations, especially if one of the sizes obtained is bigger than 500 nm. Moreover, whatever the purification process used, it is difficult to obtain only PVP-PLA with the expected molecular weight. For this reason, the final product contains, at different proportions, four polymers (PVP-PLA, PLA-OH, HO-PVP-OH and PVP). The main product remains PVP-PLA, but this method did not allow the control of molecular weight. The Mw is much smaller than expected. Based on the above noted results, the anionic polymerization was also not a sufficiently good method to prepare PVP-PLA for cost-effective development of potent drug products that are marketable.

Organocatalytic Coordination-Insertion Polymerization of PVP-PLA

The organocatalytic coordination-insertion polymerization method was attempted to produce the PVP-PLA in the presence 1,3-dimesitylimidazolinium chloride (DMIC) as catalyst. This type of N-heterocyclic carbene compound is known to produce a living ring-opening polymerization (ROP). However, DMIC compound has never been use in the polymerization of PLA when PVP-OH is used as a macro initiator. Furthermore, DMIC is not available commercially and needs to be prepared. The preparation of DMIC requires three steps and each step led to a yield greater than 85%. Schemes 5 to 7 illustrate the synthesis routes for the preparation of the DMIC. Table 5 to 7 show the amount of raw materials used for each step.

Step 1: Synthesis of DMEDI

Scheme 5 shows the Synthesis route of the first step of the preparation of DMEDI.

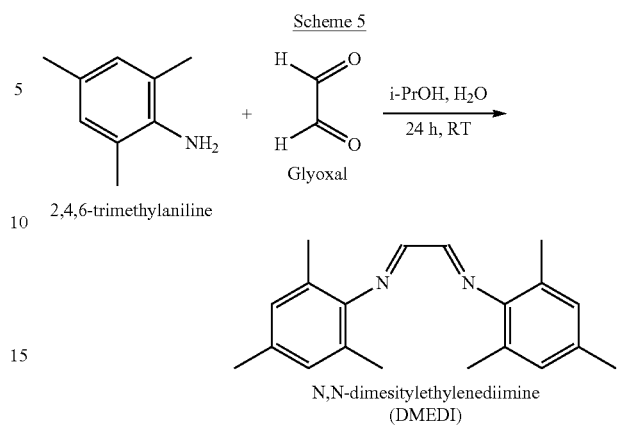

Scheme 5

TABLE 5

Raw Materials for Synthesis of DMEDI

| Compounds | Mw (g/mol) | Mass used (g) | Mole | Density (g/mL) |
|---|---|---|---|---|
| 2,4,6-trimethylaniline | 135.21 | 40.5 | 0.3000 | 0.963 |
| Glyoxal | 58.04 | 21.7 | 0.150 | 0.400 |
| Isopropyl alcohol | 60.10 | 0.600 | 0.0150 | 0.785 |

Step 2: Synthesis of DMEDADH

Scheme 6 depicts the synthesis route of the second step of the preparation of DMEDADH.

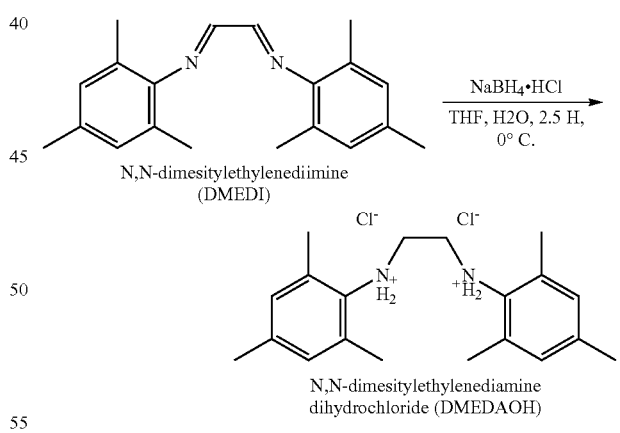

Scheme 6

TABLE 6

Raw Materials for the Synthesis of DMEDADH.

| Compounds | Mw (g/mol) | Mass used (g) | Mole | Density (g/mL) |
|---|---|---|---|---|
| DMEDI | 292.40 | 36.5 | 0.125 | N/A |
| NaBH$_4$ | 37.84 | 18.9 | 0.500 | N/A |
| HCl | 36.46 | 25.2 | 0.250 | N/A |

Step 3: Synthesis of DMIC

Scheme 7 depicts the synthesis route of the third step which led to the preparation of DMIC.

Scheme 7

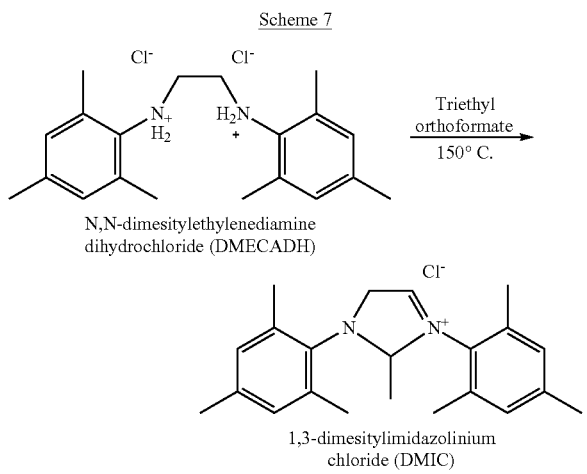

N,N-dimesitylethylenediamine dihydrochloride (DMECADH)

1,3-dimesitylimidazolinium chloride (DMIC)

TABLE 7

Raw Materials for the Synthesis of DMIC.

| Compounds | Mw (g/mol) | Mass used (g) | Mole | Density (g/mL) |
|---|---|---|---|---|
| DMEDADH | 369.60 | 18.5 | 0.050 | N/A |
| Triethyl orthoformate | 148.20 | 22.3 | 0.150 | 0.891 |

Procedure of the Synthesis

The procedure for the preparation of DMIC has been described by Delaude et al. [4]. As mentioned above, DMIC has not been used in the preparation of PVP-PLA.

Synthesis of PVP-PLA Using DMIC as a Catalyst

The preparation of PVP-PLA using DMIC as a catalyst and THF or DMSO as solvent is presented in Scheme 8.

Scheme 8

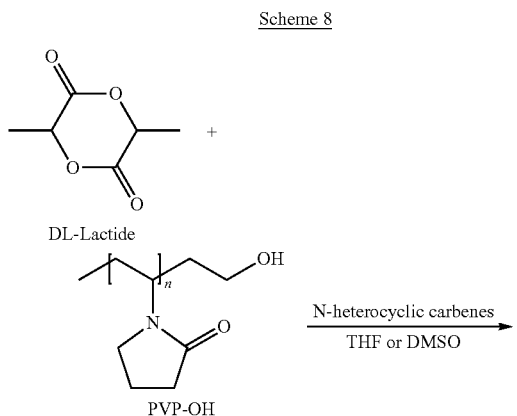

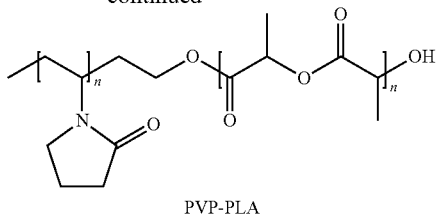

PVP-PLA

The preparation of the PVP-PLA in the presence of DMIC began with the dissolution of an amount of PVP-OH in THF or DMSO and then a quantity of DMIC was added to the mixture. After the dissolution of the DMIC, a required ratio of D,L-lactide (previously dried and purified by recrystallization from ethyl acetate) was added to the mixture. The obtained mixture was stirred under an argon atmosphere for 1 h and then put at 130° C. and kept under the argon atmosphere for another 4 hrs. The polymerization was left for 20 hrs more and then cooled to room temperature before the precipitation in diethyl ether.

The cooled solution was added dropwise to an amount of diethyl ether and then the product was collected by filtration. The product obtained was washed with three portions of diethyl ether before being dried overnight at 40° C. Table 8 shows the amount of raw materials used for the preparation of PVP-PLA in the presence of DTBL as catalyst and NMP as solvent.

TABLE 8

Raw Material for the Synthesis of PVP-PLA in the presence of DMIC

| Compounds | Mw (g/mol) | Mass used (g) | Mole | Density (g/mL) |
|---|---|---|---|---|
| DL-Lactide | 144.13 | 32.00 | 0.2220 | N/A |
| PVP-OH | 2500 | 37.00 | 0.0148 | N/A |
| DMIC | 342.91 | 5.14 | 0.0150 | N/A |
| THF | 72.11 | 222.25 | 3.0821 | 0.889 |

TABLE 9

Raw Material for the Synthesis of PVP-PLA in the presence of DMIC

| Compounds | Mw (g/mol) | Mass used (g) | Mole | Density (g/mL) |
|---|---|---|---|---|
| DL-Lactide | 144.13 | 32.00 | 0.2220 | N/A |
| PVP-OH | 2500 | 37.00 | 0.0148 | N/A |
| DMIC | 342.91 | 5.14 | 0.0150 | N/A |
| DMSO | 78.13 | 200.00 | 2.5598 | 1.100 |

Results

The data obtained from different techniques show that the D,L-Lactide reacted partially with the PVP-OH in both solvents. However, the yield for each synthesis was around 25%. This method seemed promising and its optimisation could lead to higher yield. Despite the low yield, this method led to a better control of the molecular weight. Results obtained suggest that the organocatalytic coordination-insertion polymerization could be a good method to prepare PVP-PLA for cost-effective development of potent drug products that are marketable.

Example 2: The PLA-OH Approach

As illustrated in Scheme 2, the PVP-PLA was obtained by using D,L-Lactide as raw material to generate the PLA-OH either by an organocatalytic coordination-insertion polymerization (see Scheme 2A-1) or by an organometallic coordination-insertion polymerization (see Schemes 2B-1 and 2C-1). Thus, the PLA-OH obtained was then converted to a macro chain transfer agent by substituting the terminal hydroxyl group with an O-ethyl xanthate group. The new macro chain transfer agent obtained was used to initiate the polymerization of NVP. D,L-Lactide used during this project was from Sigma Aldrich (Cat Number 303143, Lot Number STBF0369V and Mw 144.13) and was dried and purified by recrystallization from ethyl acetate before being used.

The idea behind the PLA-OH approach was to take advantage of the knowledge acquired from the lack of success with the PVP-OH approach to generate a PVP-PLA with a high yield as well as a high purity. It is desirable to avoid having a material with three different homopolymers remaining before the next polymerization step, as observed in the case of the preparation of PVP-OH. For that reason, PLA-OH was prepared first by avoiding using the anionic polymerization method. For that reason, two different coordination-insertion methods were selected to test the tactic of PLA-OH approach.

Organocatalytic Coordination-Insertion Polymerization of PLA-OH

The organocatalytic coordination-insertion polymerization of PLA-OH was performed in the presence of 4-dimethylaminopyridine (DMAP) as catalyst and isopropyl alcohol (IPA) as initiator. Scheme 9 shows the synthetic route for the preparation of PLA-OH in NMP at 80° C.

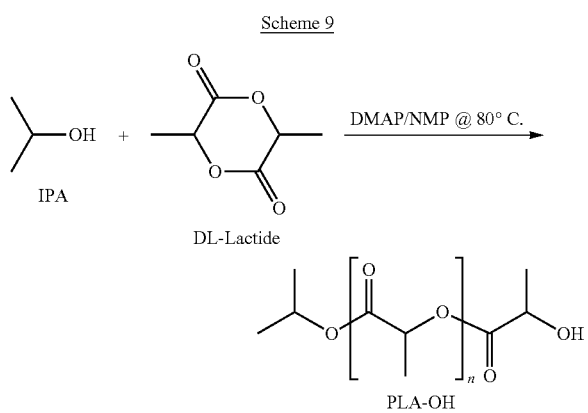

Scheme 9

Procedure of the Synthesis

PLA-OH is synthesized via ring opening polymerization (ROP) of D,L-lactide using an amount of IPA as initiator and DMAP as the catalyst. The procedure began by putting the D,L-lactide (recrystallized from ethyl acetate before used) in a dry round flask under an argon atmosphere. NMP and IPA were added and followed by the addition of DMAP in the reaction flask. The reaction mixture was heated at 80° C. for 24 hrs and kept under an argon atmosphere during that period of time. After cooling to room temperature, the obtained crude product was dissolved in DCM and precipitated from hexanes. The precipitated polymer was collected and dissolved again in DCM followed by another precipitation from hexanes. Finally, the collected PLA-OH was dried under vacuum at 40° C. for 48 hrs. Table 10 illustrates the quantity of reactants used for the synthesis of PLA-OH.

TABLE 10

Raw Materials Used for the Synthesis of PLA-OH in the Presence of DMAP

| Compounds | Mw (g/mol) | Mass used (g) | Mole | Density (g/mL) |
|---|---|---|---|---|
| DL-Lactide | 144.13 | 22.00 | 0.1526 | N/A |
| Isopropyl alcohol | 60.10 | 1.02 | 0.0170 | 0.785 |
| DMAP | 122.17 | 1.20 | 0.0099 | N/A |
| NMP | 99.13 | 128.50 | 1.2962 | 1.028 |

Results

The data obtained from the preparation of PLA-OH show that the D,L-Lactide polymerized in the presence of DMAP and IPA. The yield obtained for the synthesis was close to 60%. As for DMIC, this method seems promising and its optimisation could lead to higher yield. Despite the low yield, this method also led to a better control of the molecular weight. Results obtained show that the organocatalytic coordination-insertion polymerization of PLA-OH has the potential to generate potent, inexpensive and marketable drug products.

Organometallic Coordination-Insertion Polymerization of PLA-OH

Two organometallic coordination-insertion polymerization methods were used to produce the PLA-OH. For each method a different catalyst was used. Schemes 10 and 11 show the synthesis route in the presence of DBTDL or Sn(Oct)$_2$ as catalyst. As illustrated, the other main difference between the two syntheses is that NMP was used as solvent for the synthesis with DBTDL while that performed in the presence of Sn(Oct)$_2$ is in bulk. The temperature required for both syntheses was very close (145° C. and 150° C., respectively). Tables 11 and 12 illustrate the quantity of reactants required for each polymerization.

Scheme 10 shows the synthesis route for the preparation of PLA-OH using DBTDL as catalyst in NMP at 145° C.

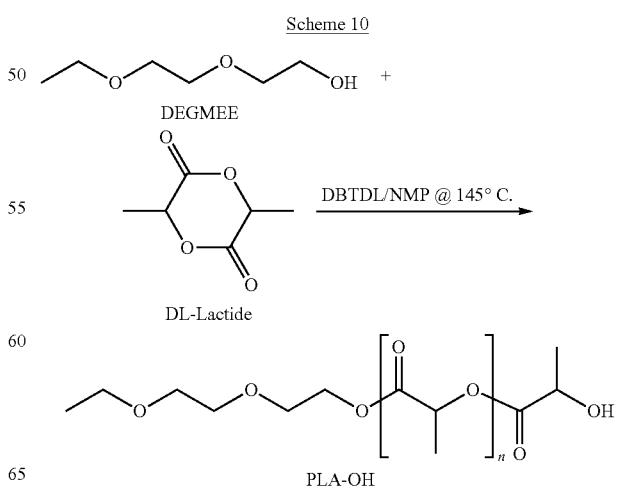

Scheme 10

TABLE 11

Raw Materials Used for the Synthesis of PLA-OH in the Presence of DBTDL

| Compounds | Mw (g/mol) | Mass used (g) | Mole | Density (g/mL) |
|---|---|---|---|---|
| DL-Lactide | 144.13 | 21.00 | 0.1457 | N/A |
| Diethylene glycol monoethyl ether | 134.17 | 1.59 | 0.0119 | 0.999 |
| DBTDL | 631.57 | 0.21 | 0.0003 | 1.066 |
| NMP | 99.13 | 10.28 | 0.1037 | 1.028 |

Scheme 11 shows the synthesis route for the preparation of PLA-OH in bulk at 145° C. and using $Sn(Oct)_2$ as catalyst.

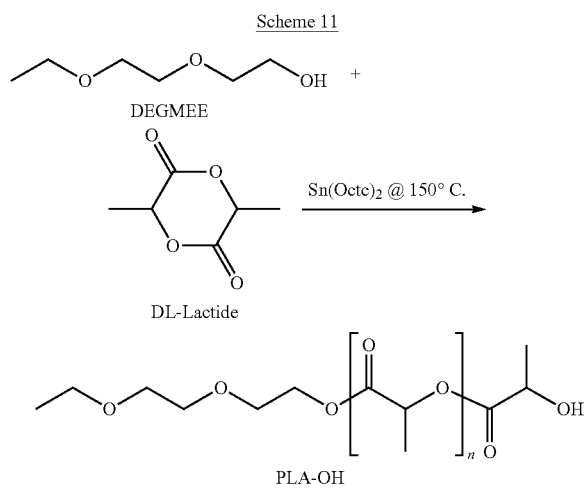

Scheme 11

TABLE 12

Raw Materials Used for the Synthesis of PLA-OH in the Presence of $Sn(Oct)_2$

| Compounds | Mw (g/mol) | Mass used (g) | Mole | Density (g/mL) |
|---|---|---|---|---|
| DL-Lactide | 144.13 | 27.20 | 0.1457 | N/A |
| Diethylene glycol monoethyl ether | 134.17 | 1.87 | 0.0139 | 0.999 |
| $Sn(Octc)_2$ | 405.12 | 0.12 | 0.0003 | 1.066 |

Procedure of the Synthesis

PLA-OH was synthesized via the ROP of D,L-lactide using in that case diethylene glycol monoethyl ether (DEGMEE) as initiator and either DBTDL or $Sn(Oct)_2$ as the catalyst. For the synthesis in the presence of $Sn(Oct)_2$, the procedure began by putting the D,L-lactide (recrystallized from ethyl acetate before use) in a dry round flask under an argon atmosphere. DEGMEE and $Sn(Oct)_2$ were added to the flask. Then, the reaction mixture was heated at 150° C. for 24 hrs. After cooling to room temperature, the crude product obtained was dissolved in certain quantity of DCM and precipitated from hexanes. The precipitated polymer was collected by filtration and then redissolved in DCM followed by precipitation from hexanes once again. Finally, the collected PLA-OH was dried under vacuum at 40° C. for 48 hrs.

Results

Results show that D,L Lactide was polymerized using both organometallic coordination-insertion polymerization methods. Table 13 illustrates the selected results obtained from both synthesis methods as well as the result for the organocatalytic coordination-insertion polymerization in the presence of DMAP.

TABLE 13

Results obtained from three methods of preparation of PLA-OH.

| Method | Mn (g/mol) | Mass (g) | Yield (%) | Time/Temperature/Solvent | Selected |
|---|---|---|---|---|---|
| DMAP | 1550 | 12.9 | 56 | 24 h/80° C./NMP | Yes |
| DBTDL | 1600 | 14.0 | 62 | 72 h/145° C./NMP | No |
| $Sn(Octc)_2$ | 1750 | 27.3 | 94 | 24 h/150° C./None | Yes |

As illustrated, all three syntheses led to a comparable molecular weight (Mn) and those values are inside the expected range value of Mn which is between 1500 and 2500. However, the yields obtained from each method are very different. Table 13 also illustrates that the synthesis in the presence of DBTDL required 72 hrs to produce a yield of 62% while the synthesis with $Sn(Oct)_2$ led to a yield of 94% in 24 hrs. In the case of the synthesis in the presence of DMAP, the yield obtained is similar to the DBTDL method, except in this case only 24 hrs were required. All three methods seem very promising but the methods with DMAP and $Sn(Oct)_2$ have been selected for more development and preliminary optimization. The selection was made strictly based on the yield obtained without any optimization and the experimental conditions, especially the time required to produce the obtained yield.

Synthesis of PVP-PLA

PLA-OH obtained from the DMAP and $Sn(Oct)_2$ was used to produce PVP-PLA. Both PLA-OHs were converted to a macro chain transfer agent by substituting the terminal hydroxyl group by an O-ethyl xanthate group. The substitution of the hydroxyl group required two steps as illustrated in Schemes 12 and 13. After the substitution, the resulting macro chain transfer agent of PLA was used to polymerize the NVP as indicated in Scheme 14.

Preparation of PLA-Br

PLA-OH was dissolved in THF (distilled before use) in a dried round-bottom flask with triethylamine while stirring under argon atmosphere. The reaction mixture was cooled in an ice bath. After the cooling, 2-bromopropionyl bromide was added drop wise from an addition flask. The reaction mixture was then stirred for 72 hrs at room temperature. The precipitated trimethylamine salt was removed by filtration and the filtrate was evaporated until dryness. The solid product was dissolved in dichloromethylene (DCM) and washed methodically with saturated sodium bicarbonate solution (4×200 mL). The organic layer was washed with water (4×300 mL), dried over anhydrous sodium sulphate, and filtered. The filtrate was concentrated by evaporation and precipitated from hexanes and dried under vacuum at 40° C. for 48 hrs. Table 14 and Scheme 12 illustrate, respectively, the quantity of reactants used and the synthesis route of the preparation of PLA-Br.

TABLE 14

Quantity of each compound used for the preparation of PLA-Br.

| Compounds | Mw (g/mol) | Mass used (g) | Mole | Density (g/mL) |
|---|---|---|---|---|
| PLA-OH | 1550 | 12.50 | 0.0081 | N/A |
| 2-Bromopropionyl bromide | 215.87 | 4.37 | 0.0203 | 2.061 |
| Triethylamine | 101.19 | 2.58 | 0.0255 | 0.726 |
| THF | 72.11 | 183.14 | 2.5397 | 0.889 |

Scheme 12 depicts a synthesis route for the preparation of PLA-Br using the PLA-OH previously obtained.

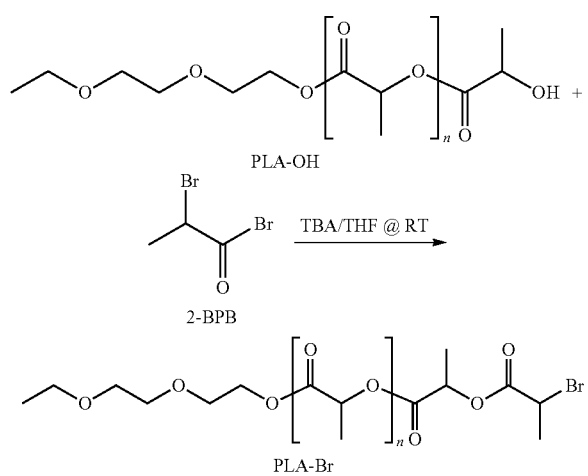

Scheme 12

Potassium O-Ethyl Xanthate Incorporation to Produce PLA-POEX

The prepared PLA-Br was mixed with potassium ethyl xanthogenate (previously prepared and dried under vacuum at 40° C.) in a dried round-bottom flask, dried DCM was added to disperse the both solids and the mixture was purged with argon during 2 hrs. In another dried round-bottom flask, pyridine was mixed with DCM while stirring under argon for also 2 hrs. The DCM solution was added to the reaction mixture of PLA-Br and kept under continuous stirring and argon for 1 h. Then, the reaction mixture was stirred at room temperature for 48 hrs. The reaction solution was washed consecutively with saturated ammonium chloride solution (4×200 mL) and saturated sodium bicarbonate solution (4×200 mL). The organic layer was washed with more water (4×200 mL), dried over anhydrous sodium sulphate, and filtered. The filtrate was concentrated by evaporation and precipitated from hexanes and dried under vacuum at 40° C. for 48 hrs. Table 15 and Scheme 13 illustrate, respectively, the quantity of reactants used and the synthesis route of PLA-POEX.

TABLE 15

Quantity of each compound used for the preparation of PLA-POEX.

| Compounds | Mw (g/mol) | Mass used (g) | Mole | Density (g/mL) |
|---|---|---|---|---|
| PLA-Br | 1685 | 10.00 | 0.0059 | N/A |
| Potassium O-Ethyl Xanthate | 160.3 | 4.08 | 0.0255 | 2.061 |
| Pyridine | 101.19 | 2.58 | 0.0255 | 0.726 |
| DCM | 84.93 | 185.00 | 2.1783 | 1.325 |

Scheme 13 depicts a synthesis route for the preparation of PLA-POEX using the PLA-Br obtained previously.

Scheme 13

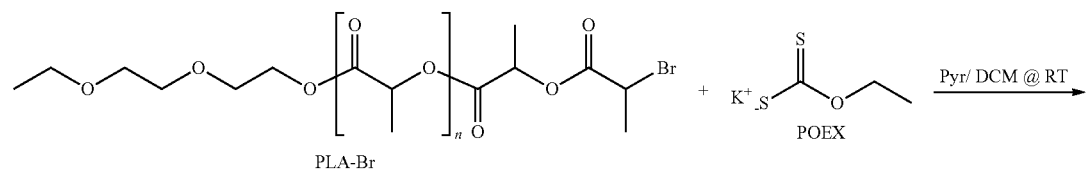

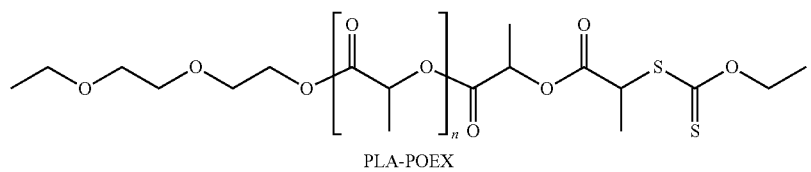

PLA-POEX

Preparation of PVP-PLA

In a dried round-bottom flask, PLA-POEX (previously dried under vacuum at 40° C.) was dissolved in THF (freshly distilled or freshly open anhydrous bottle). To this solution, NVP and AIBN were added and dissolved. The homogeneous solution was stirred and degassed with argon for 2 hours. The reaction flask was put in an oil bath preheated at 80° C. for 48 hours. After this time, the crude PVP-PLA was dissolved in DCM, precipitated from hexanes and dried under vacuum at 40° C. for overnight. The polymer was purified more by repeated the dissolution in DCM and precipitated from hexanes a second time, and finally dried under vacuum at 40° C. for 48 hrs. Table 16 and Scheme 14 illustrate, respectively, the quantity of reactants used and the scheme of the synthesis of PVP-PLA.

TABLE 16

Amount of each raw material used for the preparation of PVP-PLA

| Compounds | Mw (g/mol) | Mass used (g) | Mole | Density (g/mL) |
|---|---|---|---|---|
| PLA-POEX | 1925 | 9.75 | 0.0051 | N/A |
| NVP | 111.14 | 15.34 | 0.1380 | 1.040 |
| AIBN | 164.21 | 0.75 | 0.0046 | N/A |
| THF | 72.11 | 80.01 | 1.1096 | 0.889 |

Scheme 14 depicts a synthesis route for the preparation of PVP-PLA using the PLA-POEX obtained previously.

Characteristics of PVP-PLA Obtained

Four batches of PVP-PLA were prepared, one from PLA-OH with DMAP as the catalyst and the three others from PLA-OH with $Sn(Oct)_2$ as the catalyst. All four batches were characterized using multiple of techniques. The goal was to confirm the properties according to requirements and also to show the reproducibility and robustness of the method.

Table 17 illustrates the yield obtained for each synthesis. All three syntheses with $Sn(Oct)_2$ led to a much better yield and efficiency than the synthesis with DMAP.

TABLE 17

Obtained yield and efficiency for the preparation of PVP-PLA

| Method | Quantity (g) | Yield (%) PLA-OH | PLA-Br | PLA-POEX | PLA-PVP | Efficiency |
|---|---|---|---|---|---|---|
| DMAP | 12.0 | 56 | 85 | 80 | 64 | 25% |
| $Sn(Octc)_2$-1 | 20.5 | 94 | 93 | 80 | 82 | 57% |
| $Sn(Octc)_2$-2 | 23.8 | 94 | 91 | 81 | 95 | 66% |
| $Sn(Octc)_2$-3 | 23.6 | 94 | 91 | 81 | 94 | 65% |

Following the validation of the molecular weight using GPC-LS and proton NMR techniques, thermogravimetric analysis (TGA) as well as elemental analysis (EA) and proton NMR were applied to determine the PLA content of each polymer.

Scheme 14

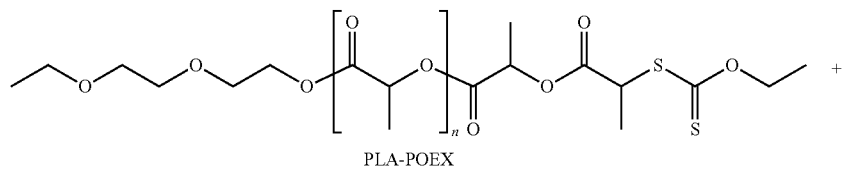

PLA-POEX

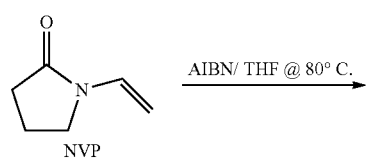

NVP

AIBN/ THF @ 80° C.

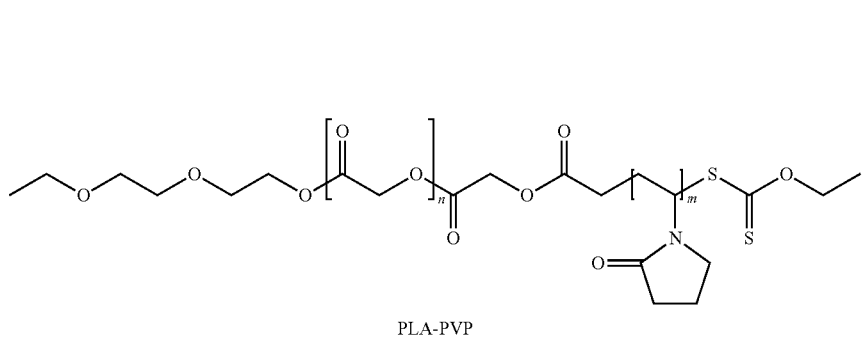

PLA-PVP

Table 18 illustrates the results obtained from each method. As expected from the molecular weight results, the PLA content was be between 35 and 45%. The results from the proton NMR and EA techniques again show the reproducibility of the $Sn(Oct)_2$ method.

TABLE 18

Obtained PLA content value from TGA, EA and proton NMR.

| Polymers | PLA %[1] | | |
|---|---|---|---|
| | TGA (wt %) | EA (wt %) | NMR (wt %) |
| WB-DMAP | 70 | 52.5 | 57 |
| WB-1 | 54 | 40.7 | 42 |
| WB-2 | 43 | 39.4 | 36 |
| WB-3 | 44 | 42.5 | 37 |

[1]The average PLA % from the Labopharm method is 33% for TGA and 36.3 for EA.

Polymer Properties in Solution

To establish the capacity of each polymer to form micelle, a polymer solution was prepared at a concentration of 90 mg/mL in phosphate buffer 100 mM at 25° C. and then the size distribution of each polymer was measured. FIG. 1 shows the size distribution profile obtained for each polymer. Once again, the size distribution confirms the reproducibility of the $Sn(Oct)_2$ method. However the size distribution observed for WB-DMAP polymer is completely different (more than 2 times smaller). This result is not surprising given that the molecular weight obtained for this polymer is 35% lower than the average value for polymers WB-1, WB-2 and WB-3. All four polymers show a unimodal size distribution. Further purification was required to obtain this unimodal distribution.

FIG. 1 depicts micelle size distribution obtained from three different batches of the new PVP-PLA polymer.

Table 19 shows the size value and the PDI value measured for all four polymers. As shown, polymers from $Sn(Oct)_2$ method led to equivalent sizes. Critical micelle concentration (CMC) is another physical property measured, and the results obtained for all polymers from $Sn(Oct)_2$ method are also equivalent. The results are very different from DMAP method.

TABLE 19

Obtained Particle size and CMC for each polymer.

| | Particle Size | | CMC |
|---|---|---|---|
| Polymers | Size (nm) | PDI | (mg/mL) |
| WB-DMAP | 16 | 0.085 | 3.0 |
| WB-1 | 47 | 0.207 | 1.8 |
| WB-2 | 45 | 0.198 | 1.6 |
| WB-3 | 51 | 0.261 | 2.0 |

Here, CMC in 10 mM PBS solution at room temperature was determined from pyrene excitation spectra (lem=390 nm) and expressed as a ratio of excitation intensity at 337 and 333 nm.

Synthesis of Additional Polymers

Given the success with the $Sn(Oct)_2$ method, five additional polymers, WB-4 to WB-8 were prepared using the PLA-OH approach with $Sn(Oct)_2$ as the catalyst. Table 20 lists characteristics of polymers produced by the PLA-OH approach. Herein, it should be noted that $M_n$ was determined by proton nuclear magnetic resonance (NMR) in deuterated DMSO at room temperature, and by from gel permeation chromatographic with light scattering detector (GPC-LS). Values from GPC-LS were determined in DMF-LiBr (10 mM) at a polymer concentration of 5 mg/mL and using a standard of Polystyrene with $M_n$ of 30 k and a PDI of 1.008 to calibrate the system. The required do/dc value for each polymer was measured and the temperature of the system was fixed at 35° C. Percent values under "TGA" were determined from $M_w$ values determined by thermogravimetric analysis. Table 20 lists the properties of various polymers produced. It should be noted that the PLA:PVP values is calculated using the PLA-POEX Mn value obtained from Proton NMR, from which the mass of PEOX (121.2) and the initiator alcohol (134.2) have been subtracted.

| | | Mn from Proton NMR | | | | | |
|---|---|---|---|---|---|---|---|
| Method | Name | PLA-OH | PLA-Br | PLA-PEOX | PVP | PVP-PLA | PLA-PVP |
| DMAP | WB-DMAP | 1550 | 1690 | 1810 | 1340 | 3150 | 1.16 |
| $Sn(Oct)_2$ | WB-2 | 1750 | 1960 | 2100 | 2850 | 4950 | 0.65 |
| $Sn(Oct)_2$ | WB-2 | 1750 | 2100 | 2250 | 4050 | 6300 | 0.49 |
| $Sn(Oct)_2$ | WB-3 | 1750 | 2100 | 2250 | 3900 | 6150 | 0.51 |
| $Sn(Oct)_2$ | WB-4 | 2110 | 2470 | 2720 | 2865 | 5585 | 0.86 |
| $Sn(Oct)_2$ | WB-5 | 1970 | 2185 | 2915 | 3505 | 6420 | 0.76 |
| $Sn(Oct)_2$ | WB-6 | 1930 | 2370 | 2665 | 3325 | 5990 | 0.72 |
| $Sn(Oct)_2$ | WB-7 | 2030 | 2195 | 2365 | 1960 | 4325 | 1.08 |
| $Sn(Oct)_2$ | WB-8 | 1880 | 1965 | 2745 | 2055 | 4800 | 1.21 |

| | Polymers | Min | Max | Ave | Min | Max | Ave | Min | Max | Ave |
|---|---|---|---|---|---|---|---|---|---|---|
| Group 1 | All | 1550 | 2110 | 1858 | 1690 | 2470 | 2115 | 1810 | 2915 | 2424 |
| Group 2 | WB1-6 & 8 | 1750 | 2110 | 1877 | 1950 | 2470 | 2164 | 2100 | 2925 | 2521 |
| Group 3 | WB1-6 | 1750 | 2110 | 1877 | 1960 | 2470 | 2193 | 2100 | 2915 | 2483 |
| Group 4 | WB4-6 | 1930 | 2110 | 2003 | 2185 | 2470 | 2342 | 2665 | 2925 | 2767 |

| | Min | Max | Ave | Min | Max | Ave | Min | Max | Ave |
|---|---|---|---|---|---|---|---|---|---|
| Group 1 | 1340 | 4050 | 2872 | 3150 | 6420 | 5297 | 0.49 | 1.21 | 0.83 |
| Group 2 | 2055 | 4050 | 3221 | 4800 | 6420 | 5742 | 0.49 | 1.22 | 0.74 |
| Group 3 | 2850 | 4050 | 3416 | 4950 | 6420 | 5899 | 0.49 | 0.86 | 0.67 |
| Group 4 | 2855 | 3505 | 3232 | 5585 | 6420 | 5998 | 0.72 | 0.86 | 0.78 |

-continued

| Name | Average unit number | | Mn and PDI from GPC-LS$^2$ | | TGA | |
|---|---|---|---|---|---|---|
| | PVP (m) | PLA* (n) | PVP-PLA | PDI | % PLA | % PVP |
| WS-DMAP | 12 | 21 | 3708 | 1.11 | | |
| WB-1 | 26 | 22 | 5192 | 1.37 | 54 | 46 |
| WB-2 | 36 | 22 | 6283 | 1.13 | 43 | 57 |
| WB-3 | 35 | 22 | 5828 | 1.32 | 44 | 56 |
| WB-4 | 26 | 27 | 5693 | 1.35 | 43 | 57 |
| WB-5 | 32 | 26 | 5994 | 1.64 | 40.1 | 59.9 |
| WB-6 | 30 | 25 | 5566 | 1.25 | 43.8 | 56.2 |
| WB-7 | 18 | 26 | 6848 | 1.37 | 52.7 | 47.3 |
| WB-8 | 19 | 24 | 6594 | 1.25 | 52.7 | 47.3 |

| Polymers | Min | Max | Ave | Min | Max | Ave | Min | Max | Ave |
|---|---|---|---|---|---|---|---|---|---|
| All | 12 | 36 | 26 | 21 | 27 | 24 | 3708 | 6848 | 5745 |
| WB1-6 & 8 | 19 | 36 | 29 | 22 | 27 | 24 | 5192 | 6594 | 5879 |
| 1-6 | 26 | 36 | 31 | 22 | 27 | 24 | 5192 | 6283 | 5759 |
| 4-6 | 26 | 32 | 29 | 25 | 27 | 26 | 5566 | 5994 | 5751 |

| Polymers | Min | Max | Ave | Min | Max | Ave | Min | Max | Ave |
|---|---|---|---|---|---|---|---|---|---|
| All | 1.11 | 1.64 | 1.31 | 40 | 54 | 47 | | | |
| WB1-6 & 8 | 1.13 | 1.64 | 1.33 | 40 | 54 | 45 | 46 | 60 | 54 |
| 1-6 | 1.13 | 1.64 | 1.34 | 40 | 54 | 45 | 46 | 60 | 55 |
| 4-6 | 1.25 | 1.64 | 1.41 | 40 | 44 | 42 | 56 | 60 | 58 |

Discussion of Examples 1 & 2

From all syntheses and characterizations performed and presented, the PLA-OH approach is the most promising, being unexpectedly more efficient than counterpart PVP-OH approaches.

Of the three methods illustrated for the advantageous PLA-OH approach, the Sn(Oct)$_2$ method gave the highest total yield for the preparation of PVP-PLA (66% in comparison of 25% for DMAP). This method has also shown very good reproducibility and robustness. Even without any additional optimization, a good control of the molecular weight and PDI with the Sn(Oct)$_2$ method was achieved. For all those reasons, the Sn(Oct)$_2$ method and polymers produced using this method were selected for further study and optimization.

Example 3: Pharmaceutical Formulations

Introduction

Control of pain is a significant burden on patients, health services, and society. For example, there are over 100 million surgeries performed in the USA alone each year and 80% of patients experience postoperative pain that is moderate severe necessitating analgesic intervention.

In over 50% of cases, patients receive an opioid drug administered intravenously to combat the pain. The second most commonly used agents to treat postoperative pain are non-steroidal anti-inflammatory drugs (NSAIDS) and acetaminophen; these drugs may be used alone to treat moderate pain and as part of a multimodal approach to supplement and reduce the dose and frequency of concomitant opioid analgesia where they have been proven effective. NSAID drugs and acetaminophen however suffer one common drawback in their use as intravenous analgesics: that of poor solubility coupled in many cases with relatively low potency. Previous attempts to overcome this drawback have been varied.

For instance, the high required dose (up to 4000 mg/day) and low solubility of acetaminophen have been circumvented by the development of products such as Ofirmev™ (Mallinckrodt) and Caldolor (Cumberland Pharmaceuticals). These are low concentration large volume formulations that must be infused slowly to the patient. While such low concentration solutions provide benefit the patient must be fitted with a new intravenous line to administer the product (causing inconvenience, discomfort and treatment cost) and the slow infusion results in a lower Cmax and later Tmax for the product than could be achieved if a bolus or slow push intravenous dose was administered. These products must be administered every 4-6 hours Elsewhere, Pfizer developed a water soluble pro-drug new chemical entity of their potent COX-2 inhibitor valdecoxib (Bextra™), called Dynastat® (parecoxib), in order to overcome the intrinsic insolubility of valdecoxib. The product must be administered every 4-6 hrs. While this is an excellent post-operative analgesic, the costs and time required to develop new chemical entities, along with the inherent patient to patient variability that results with pro-drugs does not make this a cost-effective option. The time taken for pro-drug hydrolysis and activation may also delay analgesic onset for the first, most important administration.

Products such as Toradol™ (ketorolac for injection) and Dynastat™ (diclofenac for injection) use novel formulation approaches to overcome intrinsic NSAID insolubility. Thus Toradol employs organic solvents (not beneficial for the patient) in which ketorolac is soluble while Dyloject employs hydroxypropyl beta-cyclodextrin as a solubilizing agent. Unfortunately, despite these approaches, both Toradol and Dyloject suffer from instability problems and have been the subject of numerous product recalls and market withdrawals; supply shortages are common; again these products must be administered every 4-6 hours.

Pain control drugs of low solubility (including Fluriboprofen, Celecoxib, and Acetaminophen) were selected as examples for formulation with the block copolymers described herein. In parallel, the hydrophobic non-opioid anesthetic propofol was selected as further example for formulation.

Methods & Results

Flurbiprofen Formulations

Flurbiprofen Formulation with Polymer WB-2

Flurbiprofen (termed "Flu") formulation was prepared as follows. 12.8 g of the PVP-PLA block copolymer WB-2 and 3.2 g of flurbiprofen were dissolved in 16 mL of ethanol at room temperature for approximately 15 minutes to give a final solution having a concentration of 200 mg/mL flurbiprofen and of 800 mg/mL PVP-PLA, respectively. To this solution, 16 mL mL of water was added drop-by-drop at the rate of approximately 2 mL/min under vigorous stirring using a stirring bar. To this mixture, 13 mL of 1N NaOH aqueous solution was added under stirring to bring pH to approximately 6.9. Next, 260 mL of water was added to the mixture over ca. 25 min under vigorous stirring followed by the addition of 12.8 mL of 100 mM sodium phosphate buffer pH 7.0. The mixture was then maintained under magnetic stirring over approximately 10 min. Next, the solution was concentrated to approximately 65% of its initial weight under reduced pressure in a Büchi Collegiate Rotavapor® equipped with a dry ice solvent trap and a Heidolph Rotavac Valve vacuum pump. The temperature of water bath was maintained at 30-35° C. The mixture was then diluted with water to obtain final flurbiprofen concentration of 12.5 mg/mL and filtered through 0.2 um Nylon Target2 filters (Thermo Scientific). The resulting solution had an ethanol content ca. 0.2% (wt/wt). The filtered formulation was then transferred into 10 mL glass vials by 4 mL aliquots, corresponding to 50 mg of flurbiprofen. The vials containing the mixture were freeze-dried using a VirTis Genesis 25EL lyophilizer. The composition of the resulting lyophilized flurbiprofen cakes is shown in Table 21.

TABLE 21

| Ingredients | mg/vial | %/vial |
| --- | --- | --- |
| Flurbiprofen | 50.0 | 19.2 |
| PVP-PLA copolymer WB-2 | 200.0 | 76.5 |
| Sodium hydroxide | 8.3 | 3.2 |
| Sodium phosphate monobasic | 1.6 | 0.6 |
| Sodium phosphate dibasic | 1.4 | 0.5 |
| Total | 261.3 | 100% |

Accordingly, a drug loading level (DLL) of almost 20% (wt/wt) was achieved.

Figure 2:
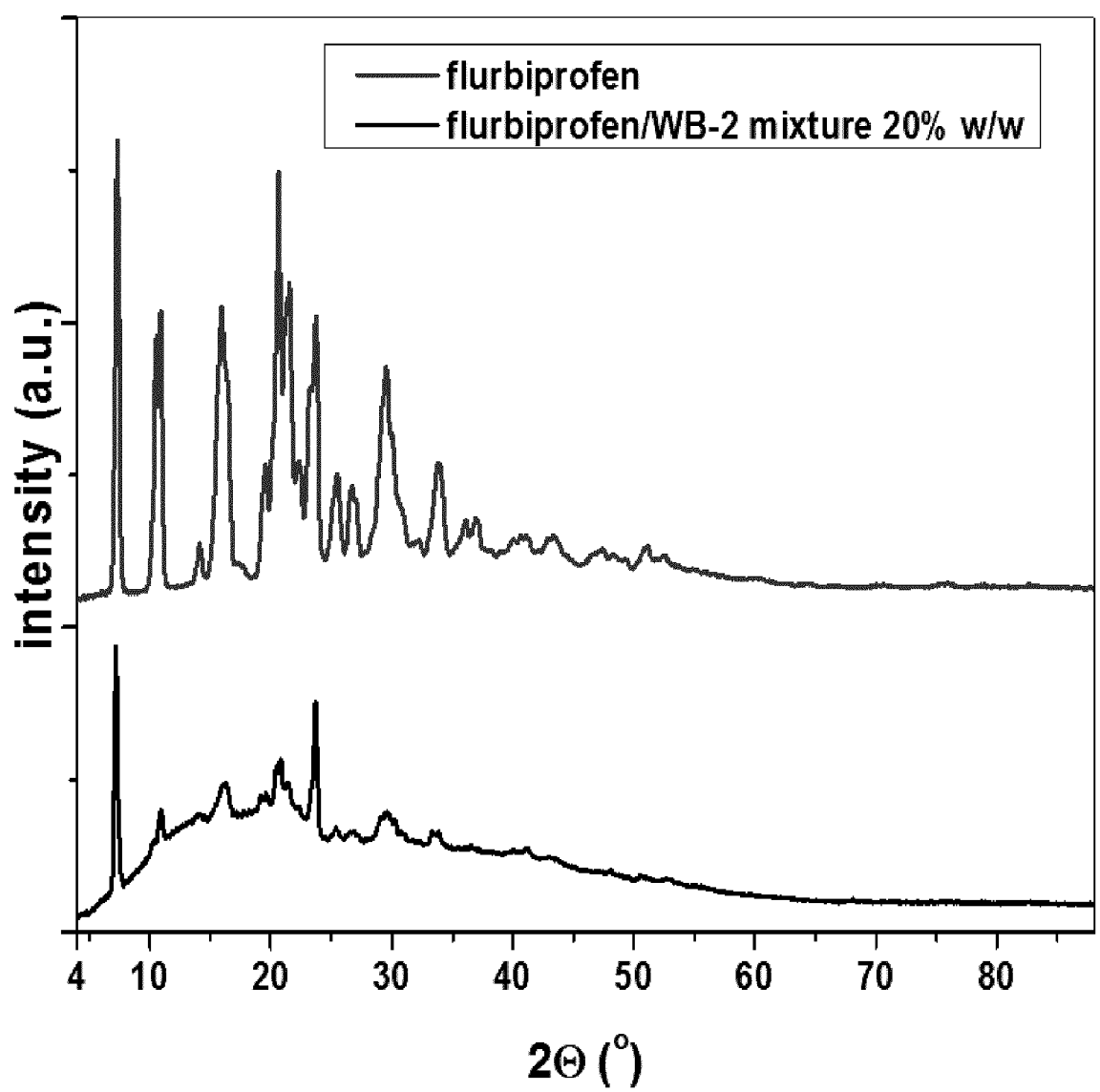
FIG. 2 depicts the XRPD patterns for flurbiprofen (top line) and its physical mixture with PVP-PLA (bottom line).

X-ray powder diffraction patterns (XRPD) were registered for flurbiprofen API, a physical mixture of flurbiprofen and PVP-PLA block copolymer WB-2 containing 20% (w/w) of API, and for the lyophilized flurbiprofen cake. XRPD measurements for flurbiprofen and the physical mixture were performed on a Bruker D8 Discover diffractometer, whereas the diffraction pattern for the lyophilized cake was registered on a Bruker D8 Advanced instrument. Both instruments were equipped with copper K$\alpha$1 source of X-rays ($\lambda$=1.54 Å) and used Bragg-Brentano $\Theta$-2$\Theta$ geometry. FIG. 2 shows the XRPD patterns for flurbiprofen and its physical mixture with PVP-PLA. In both cases, the presence of well-defined sharp peaks confirms the crystalline nature of the API.

Figure 3:
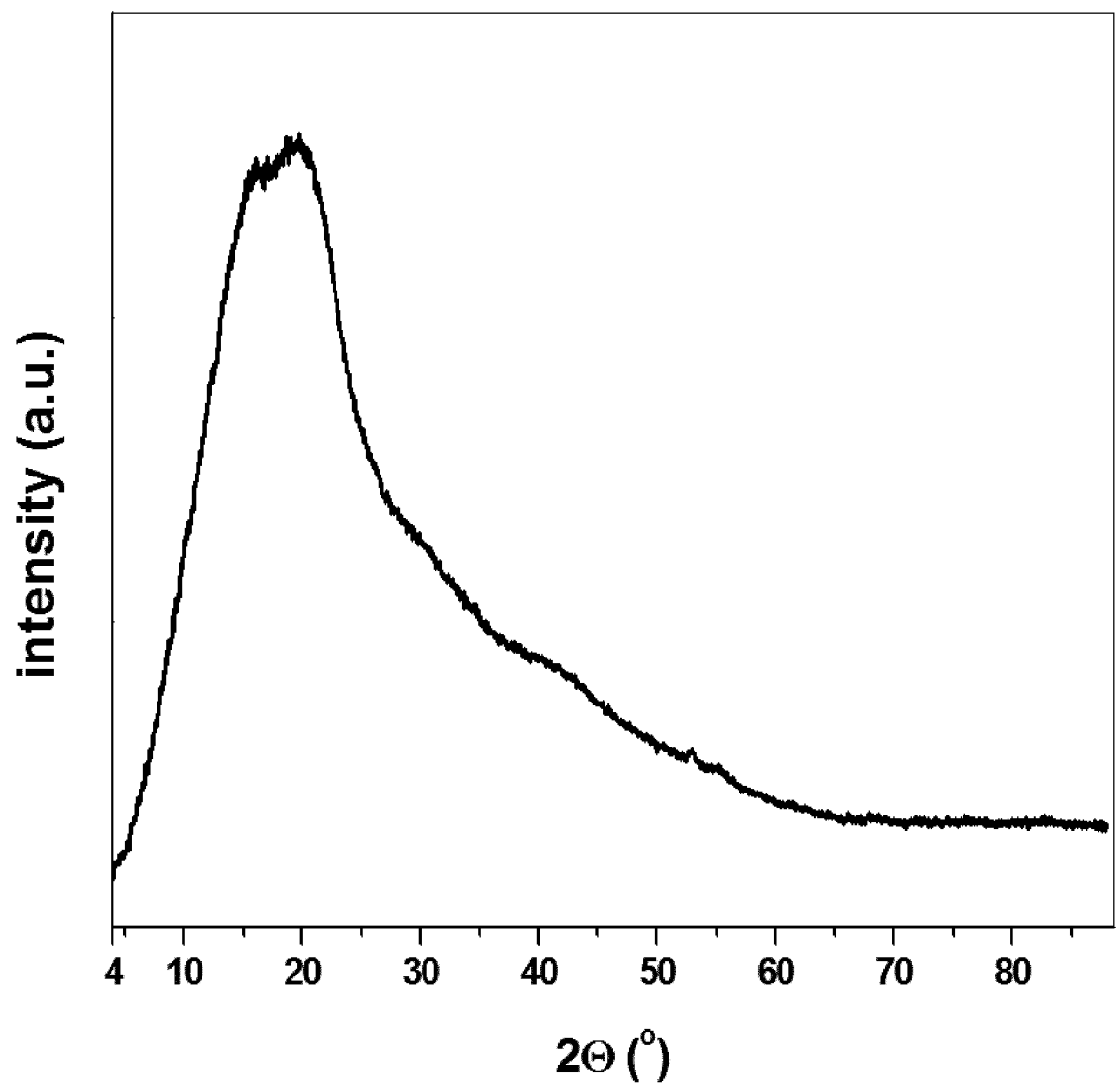
FIG. 3 depicts the XRPD pattern of lyophilized flurbiprofen cake that contains similar amount of the API as physical mixture shown in FIG. 2.

FIG. 3 shows the XRPD pattern of lyophilized flurbiprofen cake that contains the same amount of the API as the physical mixture shown in FIG. 2. However, in this case, the sharp peaks of crystalline flurbiprofen were not observed. This confirms that in the freeze-dried solid formulation of flurbiprofen, the API is present in amorphous state.

Figure 4:
FIG. 4 shows pictures, with panel A showing the picture of the freeze-dried cake and the solution obtained after reconstitution of the cake with water for injection at flurbiprofen concentration of 50 mg/mL, and panel B showing a closer view of the solution of panel A.

FIG. 4, panel A shows the picture of the freeze-dried cake and the solution obtained after reconstitution of the cake with water for injection at a flurbiprofen concentration of 50 mg/mL. The cake shows a fine sponge-like structure with no cracking or collapse. Closer inspection of the reconstituted liquid (FIG. 4, panel B) confirms the clarity of solution and the absence of visible solid particles.

Lyophilized cakes were reconstituted in water for injection in less than 2 min to give clear, particle-free solutions having a flurbiprofen concentration of 50 mg/mL. The pH of reconstituted solutions was in the range from 7.2 to 7.4 measured using an Accumet AP61 pH-meter equipped with a gel-filled epoxy-body combination electrode. Optical transmittance was determined in 1-cm disposable polystyrene cuvettes on an Agilent Cary UV-Vis-NIR 5000 spectrometer. The measurements were performed at 650 nm and room temperature using empty cuvette as a blank. The reconstituted mixtures had optical transmittance between 99% and 102%. Osmolarity of reconstituted samples was measured with a freezing point depression 3300 Micro-Osmometer (Advanced Instruments) and it was in the range of 320 to 340 mOsm/kg. Z-average size of micelles and their size distribution was determined at 25° C. by dynamic light scattering using a Malvern Zetasizer Nano ZS equipped with 10 mW He—Ne laser operating at 633 nm. Z-average particle size and its polydispersity varied from 31.5 to 31.8 nm and from 0.24 to 0.28, respectively.

Figure 5:
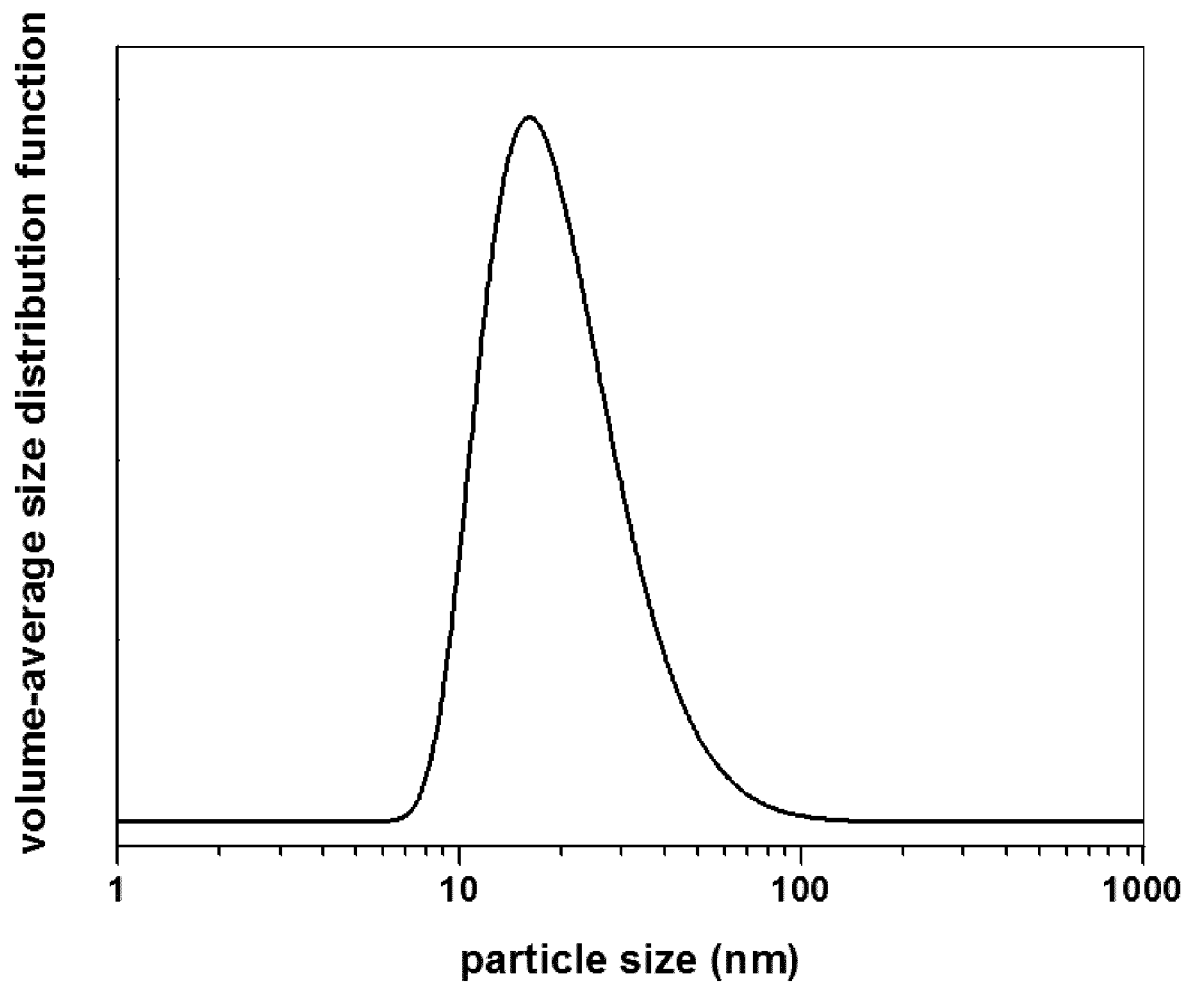
FIG. 5 depicts the particle size distribution of a flurbiprofen formulation reconstituted at 50 mg/mL.

FIG. 5 shows that the particle size distribution for the flurbiprofen formulation reconstituted at 50 mg/mL is unimodal and that the volume-average size of micelles varies from ca. 8 to ca. 100 nm.

Figure 6:
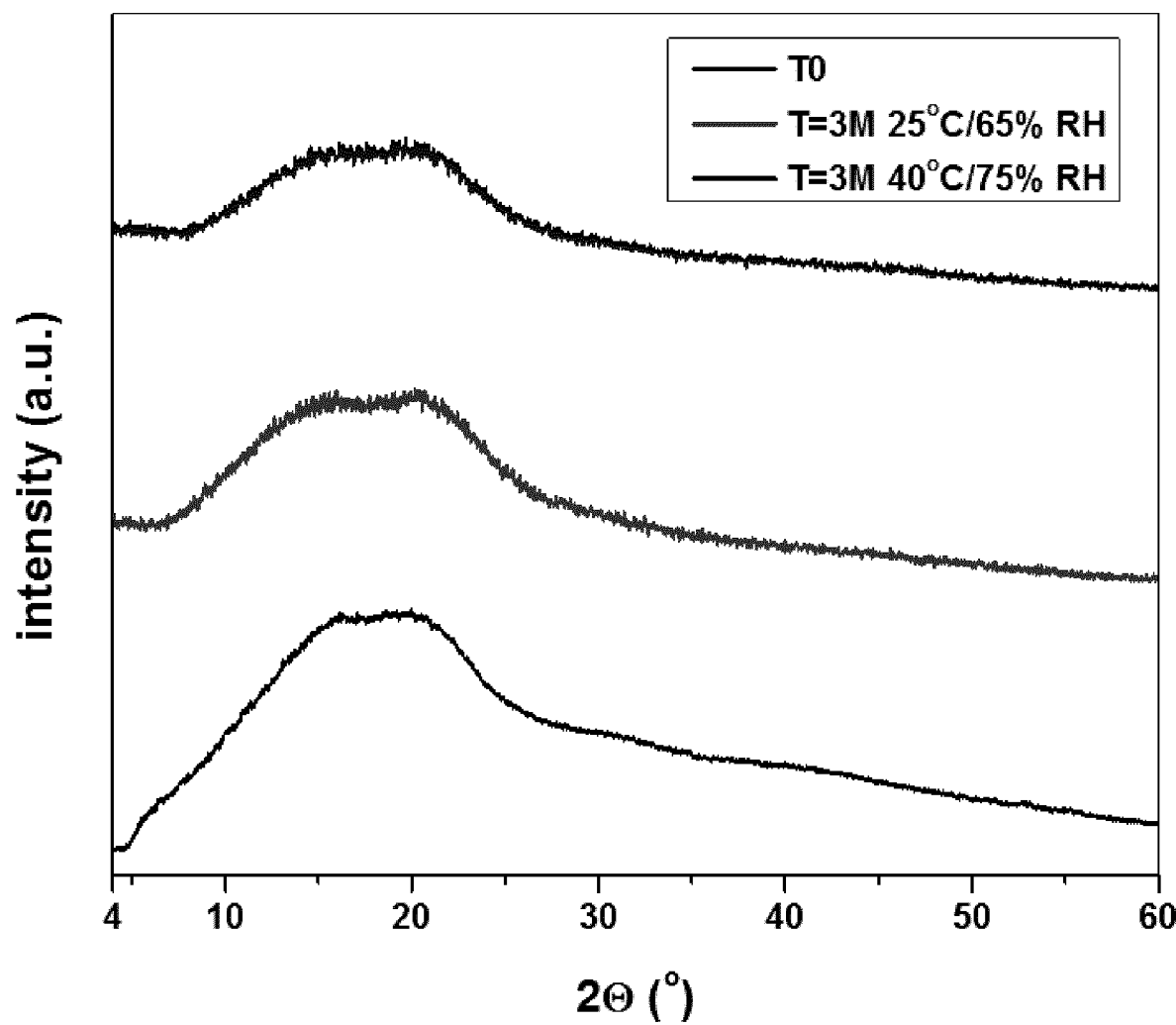
FIG. 6 depicts XRPD pattern of the FLU product at time zero and after T=3 months of storage in both conditions.

Stability of the freeze-dried flurbiprofen cakes prepared with the PVP-PLA block copolymer WB-2 was monitored at 25° C./65% RH and 40° C./75% RH. FIG. 6 shows the XRPD pattern of the drug product at time zero and after T=3 months of storage in both conditions. The absence of well-resolved sharp peaks of crystalline flurbiprofen confirms that the API can preserve its amorphous state at least for 3 months in both conditions. This data has been extended to T=6 months, wherein the absence of well-resolved sharp peaks of crystalline Flurbiprofen again confirmed that the API can preserve its amorphous state at least for 6 months at both conditions (data not shown).

The characteristics of reconstituted cakes (flurbiprofen=50 mg/mL) at different stages of stability assessment are shown in Table 22. No significant changes were observed upon 6 months of storage at both 25 and 40° C., confirming thus the stability of the freeze-dried product.

TABLE 22

| | Flurbiprofen assay (%) | pH | Optical transmittance (%) | Z-average size (nm) | Osmolality (mOsm/kg) |
| --- | --- | --- | --- | --- | --- |
| T0 | 98.3 | 7.33 | 101.7 | 31.2 | 332 |
| T = 1 M (40° C./75% RH) | 99.3 | 7.32 | 101.8 | 35.4 | 334 |
| T = 2 M (40° C./75% RH) | 101.0 | 7.25 | 101.6 | 39.2 | 348 |

TABLE 22-continued

| | Flurbiprofen assay (%) | pH | Optical transmittance (%) | Z-average size (nm) | Osmolality (mOsm/kg) |
|---|---|---|---|---|---|
| T = 3 M (40° C./75% RH) | 98.4 | 7.13 | 99.2 | 40.0 | 354 |
| T = 6 M (40° C./75% RH) | 99.7 | 6.87 | 100.6 | 43.6 | 378 |
| T = 3 M (25° C./65% RH) | 100.2 | 7.44 | 98.8 | 31.1 | 312 |
| T = 6 M (25° C./65% RH) | 101.0 | 7.39 | 101.5 | 31.4 | 317 |

Flurbiprofen Formulations with Polymers WB-4 and WB-7

Given the success with WB-2, formulations of FLU with WB-4 and WB-7 polymers were attempted. WB-4 or WB-7 PVP-PLA block copolymers were each dissolved together with flurbiprofen in 2.75 mL of ethanol under magnetic stirring in a glass beaker at room temperature for approximately 15 minutes to give the solution a concentration of 200 and 800 mg/mL of flurbiprofen and PVP-PLA block copolymer, respectively. To both these solutions, 2.75 mL of water was added drop-by-drop over ca. 1 min. and under vigorous stirring using a magnetic stirring bar and stirring plate. 1N NaOH aqueous solution was added next under stirring to bring pH close to neutral (6.2-6.8). Finally, water was added to the mixture under vigorous stirring, followed by the addition of 2.2 mL of 100 mM sodium phosphate buffer pH 7.0. The mixtures were then kept under magnetic stirring over approximately 10 min. Next, both solutions were concentrated to approximately 60% of their initial weight under reduced pressure in a Büchi Collegiate Rotavapor® equipped with a dry ice solvent trap and a Heidolph Rotavac Valve vacuum pump. The temperature of the water bath was maintained at 30-35° C. Resulting transparent solutions were then diluted with water to obtain a final flurbiprofen concentration of 12.5 mg/mL, and filtered through 0.2 um Nylon Target2 filters (Thermo Scientific). Filtered formulations were transferred as 4 mL aliquots (corresponding to 50 mg of Flurbiprofen) into 10 mL glass vials. Filled vials were freeze-dried using a VirTis Genesis 25EL lyophilizer. In Table 23 are shown amounts of products used for preparation of flurbiprofen formulations with WB-4 or WB-7 polymers. The composition of the resulting lyophilized flurbiprofen cakes prepared using WB-4 or WB-7 polymers are shown in Table 24 and Table 25, respectively.

Figure 7:
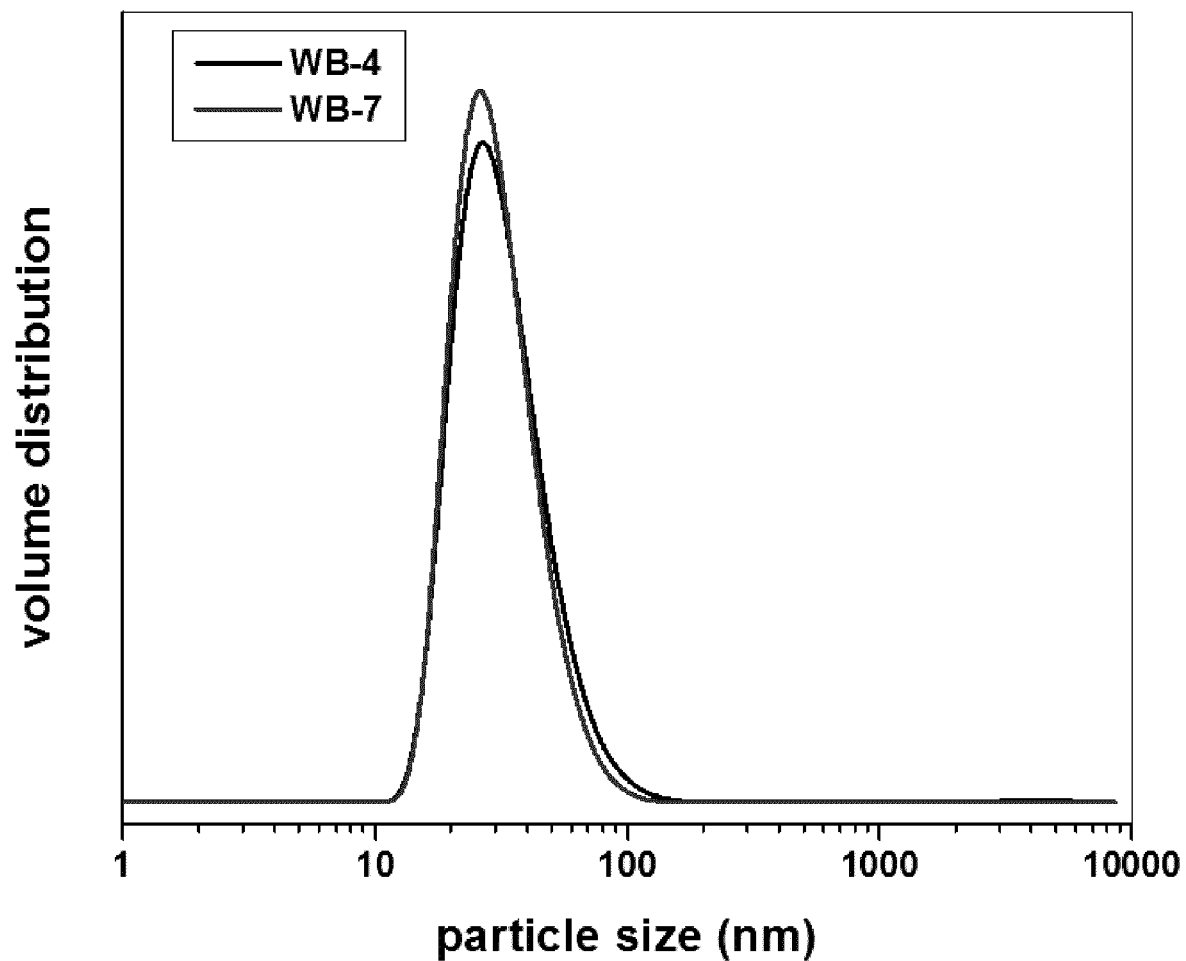
FIG. 7 depicts particle size distributions of flurbiprofen formulations prepared using WB-4 and WB-7 polymers.

Lyophilized cakes were reconstituted in water for injection in less than 1 min to give clear, particle-free solutions having flurbiprofen concentration of 50 mg/mL. pH of reconstituted solutions for the formulations obtained with both polymers was in the range from 7.2 to 7.4 as measured using an Accumet AP61 pH-meter equipped with a gel-filled epoxy-body combination electrode. Osmolality of reconstituted samples was measured with a freezing point depression 3300 Micro-Osmometer (Advanced Instruments) and it was in the range of 380 to 420 mOsm/kg. Optical transmittance was determined in 1-cm disposable polystyrene cuvettes using an Agilent Cary UV-Vis-NIR 5000 spectrometer. The measurements were performed at 650 nm and room temperature using empty cuvette as a blank. The reconstituted solutions prepared form the cakes containing WB-4 polymer showed optical transmittance between 98% and 100%. The solutions of the samples prepared using polymer WB-7 have slightly lower transmittance, in the range 84-85%. Z-average size of micelles and their size distribution was determined at 25° C. by dynamic light scattering using a Malvern Zetasizer Nano ZS equipped with 10 mW He—Ne laser operating at 633 nm. Z-average particle size for both reconstituted formulations of the cakes containing WB-4 and WB-7 was similar and equal to 43.9 and 43.6 nm, respectively. FIG. 7 shows that particle size distributions for formulations prepared using two different polymer samples WB-4 and WB-7 and reconstituted at 50 mg/mL have similar shape with the volume-average size of micelles from ca. 10 to ca. 200 nm. Values of the parameters determined upon characterization of reconstituted Flurbiprofen formulations are shown in Table 26.

TABLE 23

| | WB-4 | WB-7 |
|---|---|---|
| PVP-PLA copolymer (WB-4 or WB-7), mg | 2200 | 2200 |
| Flurbiprofen, mg | 550 | 550 |
| Ethanol, mL | 2.75 | 2.75 |
| Water (before evaporation), mL | 44.50 | 45.50 |
| Sodium hydroxide solution (1N), mL | 3.40 | 2.40 |
| Sodium phosphate buffer (100 mM, pH 7.0), mL | 2.20 | 2.20 |
| Ratio of formulation weight after and before evaporation | 0.63 | 0.59 |
| Water added after evaporation to adjust FLU concentration to 12.5 mg/mL | 10.00 | 12.70 |

TABLE 24

| Ingredients | mg/vial | %/vial |
|---|---|---|
| Flurbiprofen | 50.0 | 17.2 |
| PVP-PLA copolymer WB-4 | 200.0 | 68.7 |
| Sodium hydroxide | 12.3 | 4.2 |
| Sodium phosphate monobasic 120 | 13.2 | 4.5 |
| Sodium phosphate dibasic 142 | 15.6 | 5.4 |
| Total | 291.1 mg | 100% |

TABLE 25

| Ingredients | mg/vial | %/vial |
|---|---|---|
| Flurbiprofen | 50.0 | 17.3 |
| PVP-PLA copolymer WB-7 | 200.0 | 69.4 |
| Sodium hydroxide | 9.6 | 3.3 |
| Sodium phosphate monobasic | 13.2 | 4.6 |
| Sodium phosphate dibasic | 15.6 | 5.4 |
| Total | 288.4 mg | 100% |

TABLE 26

| Parameter | WB-4 | WB-7 |
|---|---|---|
| Reconstitution time (s) | 30 | 50 |
| pH | 7.29 | 7.22 |
| Osmolality (mOsm/kg) | 419 | 380 |
| Optical transmittance (%) | 99.1 | 84.2 |
| Z-average particle size (nm) | 43.9 | 43.6 |
| Particle size distribution | 0.273 | 0.233 |

Flurbiprofen Formulations with Other PLA-OH Polymers

Given the above successes, the ability of other polymers derived from the PLA-OH method were tested for their ability to formulate FLU, i.e., polymers WB-DMAP, WB-1, WB-3, WB-5, WB-6, and WB-8. All polymers were found to be capable of formulating FLU, achieving a suitably clear solutions having a suitable DLL.

Acetaminophen Formulations

Acetaminophen Formulation with Polymer WB-2 (no antioxidant)

Acetaminophen (APAP) formulation was prepared as follows. 4.40 g of APAP was dissolved in 29 mL of ethanol in a glass beaker under stirring at room temperature for approximately 10 minutes following the addition of 20.05 g WB-4 block copolymer and an additional 10 minutes stirring. To this solution, 200 mL mL of water was added drop-by-drop at the rate of approximately 10 mL/min and under vigorous stirring using a stirring bar. To this mixture, 0.38 mL of 1N NaOH aqueous solution was added under stirring to bring the pH to approximately 7.1. Next, 200 mL of water was added to the mixture over ca. 20 min under vigorous stirring following by the addition of 12.2 mL of aqueous solution of mannitol at concentration 100 mg/mL. Stirring continued for an additional 10 min. Next, the solution was concentrated during ca. 2 hrs to 42% of its initial weight under reduced pressure in a Büchi Collegiate Rotavapor® equipped with a dry ice solvent trap and a Heidolph Rotavac Valve vacuum pump. The temperature of the water bath was maintained at 30-35° C. To the concentrated solution, 4.9 mL of 100 mM sodium phosphate buffer pH 7.0 was added. The mixture was then diluted with 29 mL of water to obtain final APAP concentration of 20 mg/mL and filtered through 0.2 um Nylon Target2 filters (Thermo Scientific). Filtered formulation was then transferred into 10 mL glass vials by 5 mL aliquots, corresponding to 100 mg of APAP. The vials containing the formulation were freeze-dried using a VirTis Genesis 25EL lyophilizer. The composition of the resulting lyophilized acetaminophen cakes is shown in Table 27.

TABLE 27

| Ingredients | mg/vial | %/vial |
| --- | --- | --- |
| Acetaminophen | 100.0 | 17.09% |
| PVP-PLA copolymer WB-4 | 455.6 | 77.88% |
| Mannitol | 27.8 | 4.75% |
| Sodium hydroxide | 0.2 | 0.03% |
| Sodium phosphate monobasic | 0.6 | 0.11% |
| Sodium phosphate dibasic | 0.8 | 0.13% |
| Total | | 100% |

According, a DLL of over 17% was achieved.

Figure 8:
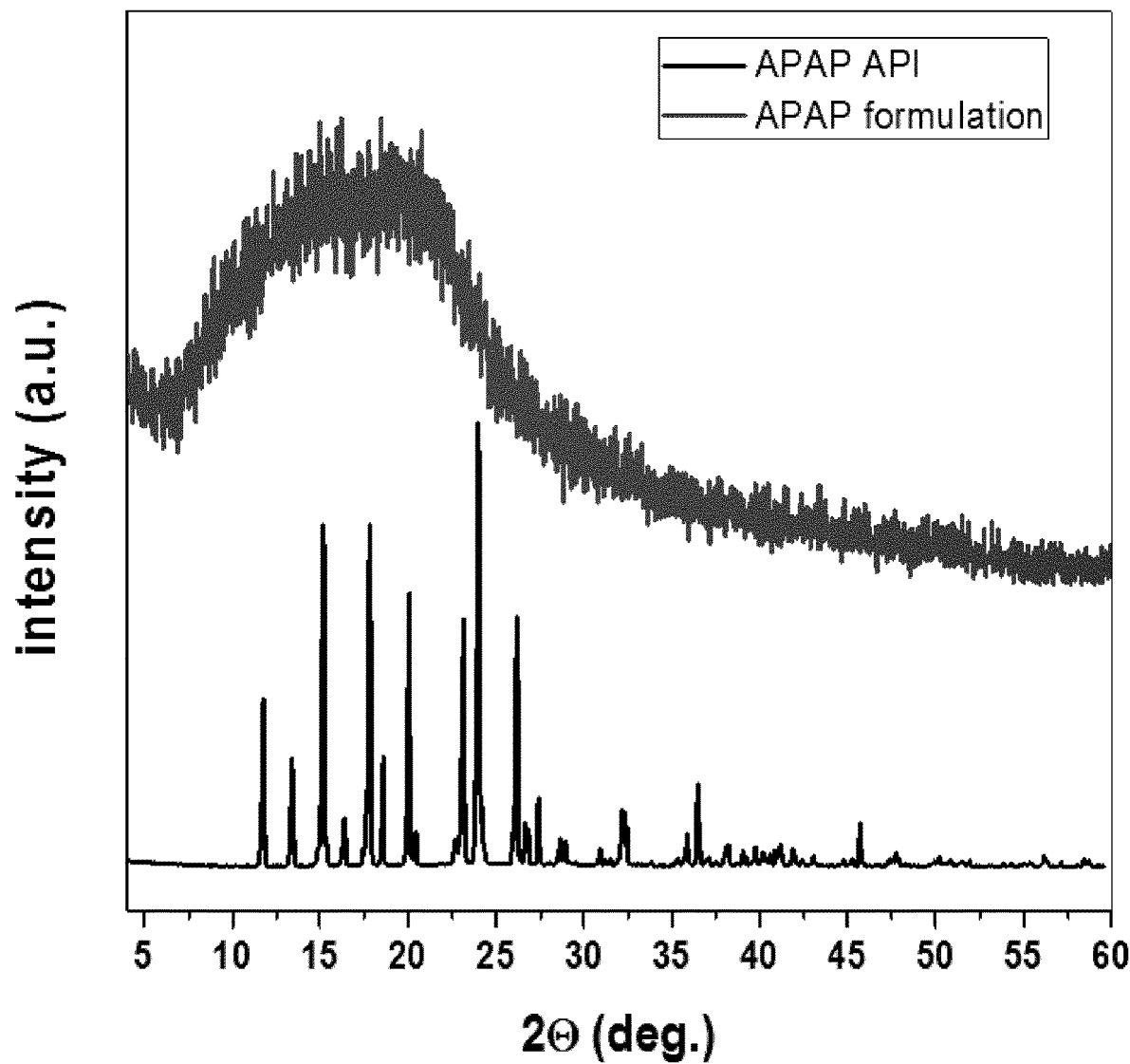
FIG. 8 depicts XRPD patterns for acetaminophen API and lyophilized cake of the drug product.

X-ray powder diffraction patterns (XRPD) were registered for acetaminophen API and for the lyophilized acetaminophen cake. XRPD measurements were registered on a Bruker D8 Advanced instrument equipped with copper $K\alpha_1$ source of X-rays ($\lambda=1.54$ Å) and used Bragg-Brentano $\Theta$-$2\Theta$ geometry. FIG. 8 shows the XRPD patterns for acetaminophen API and lyophilized cake of drug product. The presence of sharp peaks characteristic for crystalline acetaminophen was not detected, in the case of APAP formulation, not observed, confirming that in the freeze-dried solid cakes the API is present in amorphous state.

Figure 9:
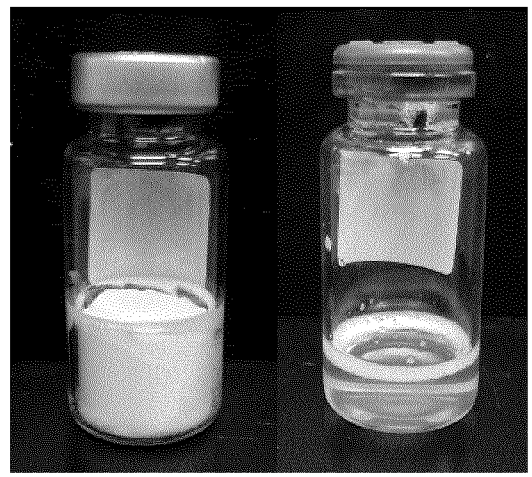
FIG. 9 depicts a picture of the freeze-dried acetaminophen cake and the solution obtained after reconstitution of the cake with water for injection at the acetaminophen concentration of 50 mg/mL.

FIG. 9 shows the picture of the freeze-dried cake and the solution obtained after reconstitution of the cake with water for injection at the acetaminophen concentration of 50 mg/mL. The cake show fine sponge-like structure with no cracking or collapse. Close inspection of the reconstituted liquid (FIG. 9b) confirms the clarity of solution and the absence of visible solid particles.

Figure 10:
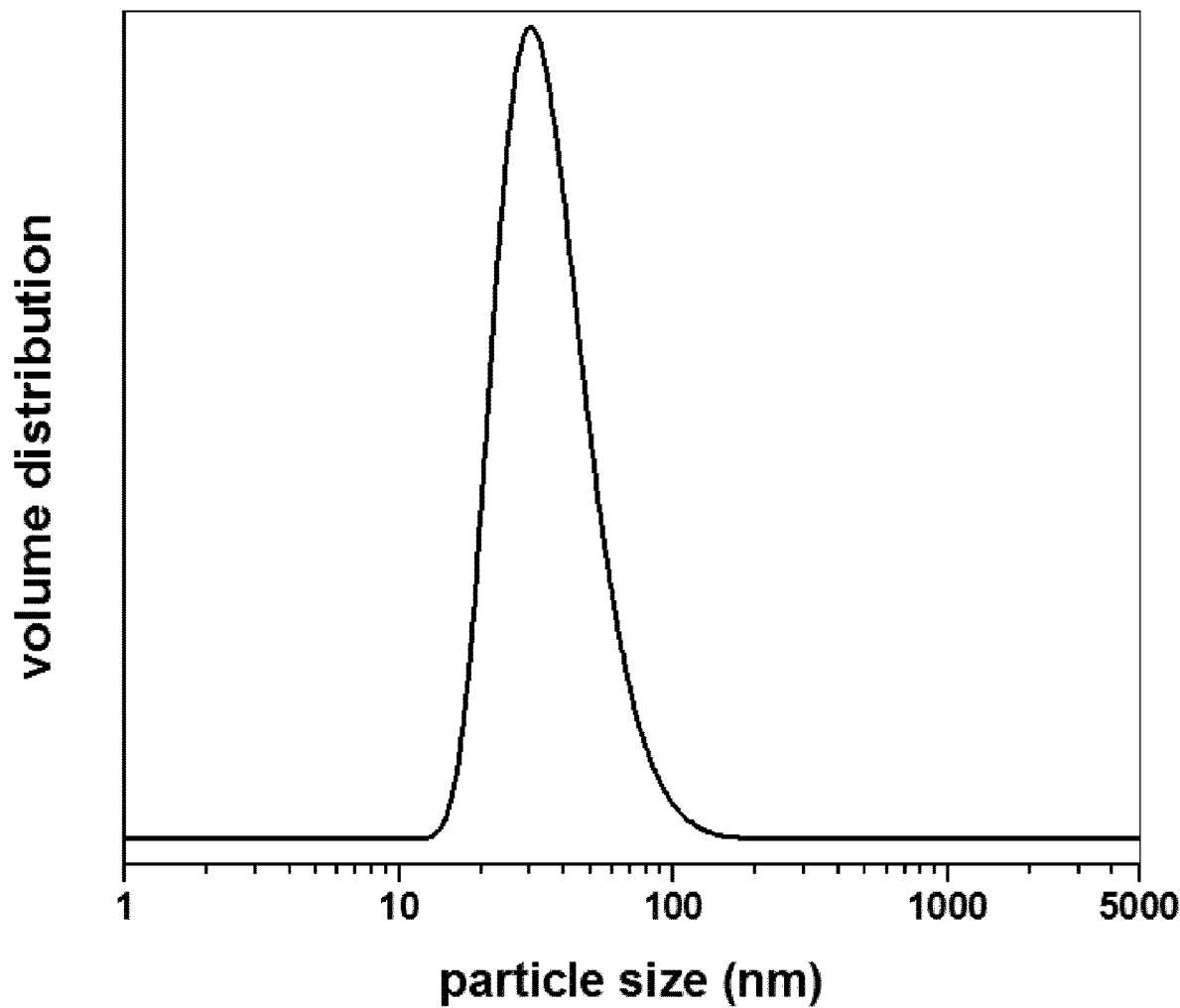
FIG. 10 depicts particle size distribution for APAP formulation reconstituted at 50 mg/mL.

Lyophilized cakes undergo complete dissolution in water in ca. 2-3 min to give clear, particle-free solutions having acetaminophen concentration of 50 mg/mL. pH of reconstituted solutions was in the range from 7.5 to 7.7 as measured using an Accumet AP61 pH-meter equipped with a gel-filled epoxy-body combination electrode. Optical transmittance was determined in 1-cm disposable polystyrene cuvettes on an Agilent Cary UV-Vis-NIR 5000 spectrometer. The measurements were performed at 650 nm and room temperature using empty cuvette as a blank. The reconstituted mixtures had an optical transmittance of around 86%. Osmolality of reconstituted samples was measured with a freezing point depression 3300 Micro-Osmometer (Advanced Instruments) and it was in the range of 250 to 265 mOsm/kg. Z-average size of micelles and their size distribution was determined at 25° C. by dynamic light scattering using a Malvern Zetasizer Nano ZS equipped with 10 mW He—Ne laser operating at 633 nm. Z-average particle size and its polydispersity varied from 48 to 51 nm and from 0.19 to 0.22, respectively. FIG. 10 shows that particle size distribution for APAP formulation reconstituted at 50 mg/mL is monomodal and that the volume-average size of micelles varies from ca. 15 to ca. 200 nm.

Acetaminophen Formulations with Polymers WB-4 and WB-7

Given the above success, APAP formulations with WB-4 and WB-7 polymers were prepared as follows. APAP was dissolved in 3 mL of ethanol in a glass beaker under stirring at room temperature for approximately 5 minutes following addition of WB-4 or WB-7 block copolymer and an additional 10 minutes stirring. To these solutions, 40 mL of water was added drop-by-drop at the rate of approximately 10 mL/min. and under vigorous stirring. Next, 0.1N NaOH aqueous solution was added to bring pH to approximately 7.2 following by the addition of 40 mL of water over ca. 10 min. In the next step, 1.25 mL of aqueous solution of mannitol at concentration 100 mg/mL was added to both solutions and the stirring continued for the additional 10 min. Both formulations were subsequently concentrated for ca. 30-40 min. to 20-40% of its initial weight under reduced pressure in a Büchi Collegiate Rotavapor® equipped with a dry ice solvent trap and a Heidolph Rotavac Valve vacuum pump. Temperature of the water bath was maintained at 40-45° C. To each of these concentrated solutions, 0.5 mL of 100 mM sodium phosphate buffer pH 7.0 was added. The mixtures were then diluted with water to obtain final APAP concentration of 20 mg/mL. The solutions were filtered through 0.2 um Nylon Target2 filters (Thermo Scientific). Filtered formulations were then transferred into 10 mL glass lyophilisation vials in 5 mL aliquots, corresponding to 100 mg of APAP. The vials containing the formulations were freeze-dried using a VirTis Genesis 25EL lyophilizer. In Table 28 are listed the products used to prepare solid reconstituted acetaminophen formulations containing WB-4 or WB-7 polymers. The compositions of the resulting lyophilized cakes are shown in Tables 29 and 30, respectively.

Figure 11:
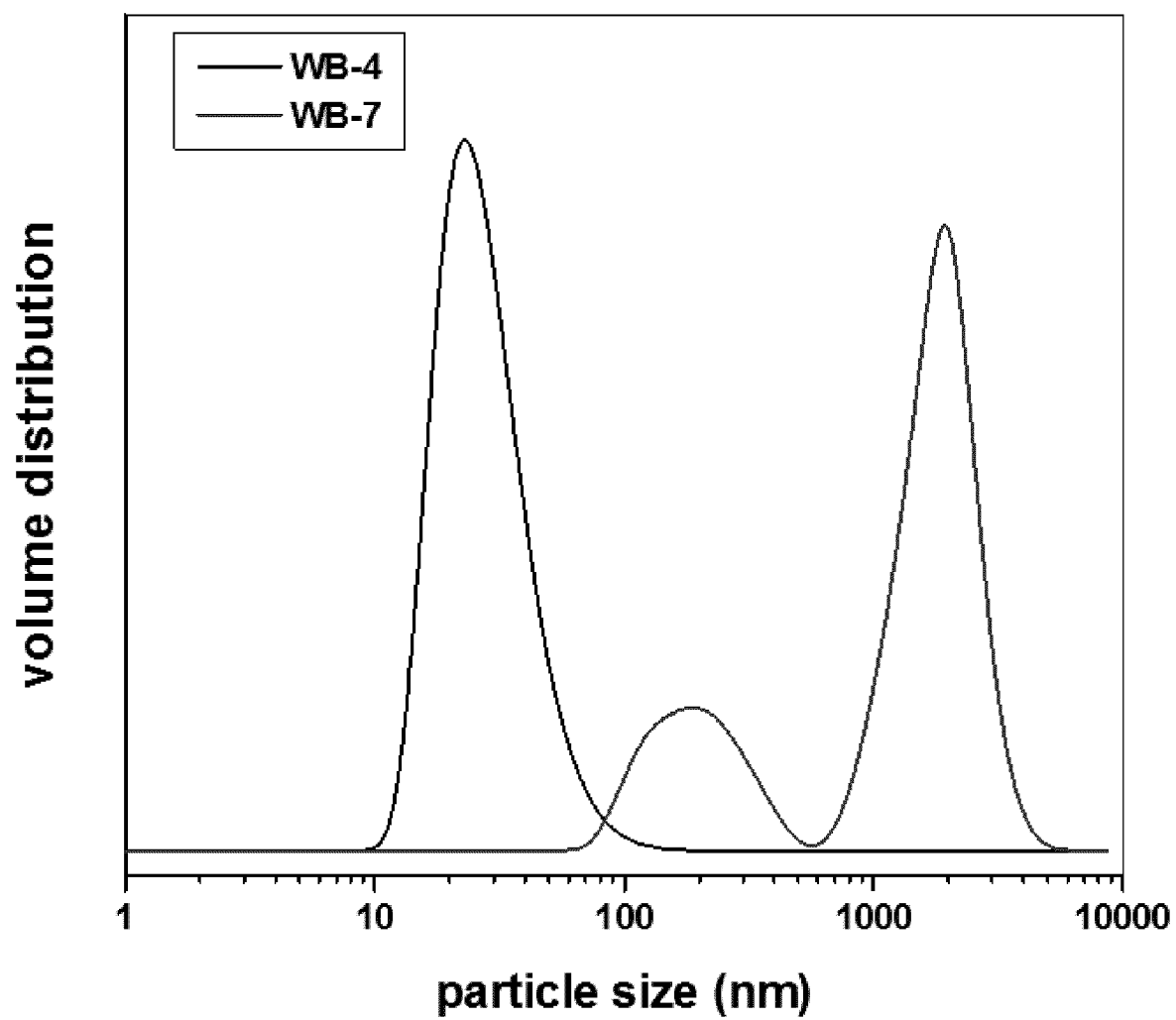
FIG. 11 depicts particle size distributions for acetaminophen formulations prepared using two different polymers WB-4 and WB-7 and reconstituted at 50 mg/mL.

Lyophilized cakes of formulation prepared using polymer WB-4 were reconstituted in water for injection in less than 3 minutes to give clear, particle-free solutions of acetaminophen concentration 50 mg/mL. In contrast, the reconstitution of the cakes prepared with WB-7 polymer was much faster (less than 1 min.), but the resulting solutions showed significant cloudiness in this case. This difference is further supported by optical transmittance measurements. The reconstituted formulations containing WB-4 polymer are characterized by optical transmittance of ca. 95%. The solutions of the formulations prepared using polymer WB-7 have significantly lower transmittance, in the range 40-42%. While Z-average particle size for reconstituted formulations of the cakes APAP/WB-4 was 44.3 nm, the size of the particles in the reconstituted formulation of APAP/WB-7 was much higher and equal to 218 nm. FIG. 11 shows that particle size distributions for formulations prepared using two different polymers WB-4 and WB-7 and reconstituted at 50 mg/mL have different shapes with the volume-average size of micelles from ca. 10 to ca. 200 nm. This is in strong contrast with the behavior of flurbiprofen formulations prepared with these two polymers. pH of reconstituted solutions for the formulations obtained with both polymers was similar and in the range 7.20-7.25. Osmolality of the reconstituted samples was also similar for both polymers and comprised in the range 271-281 mOsm/kg. Values of the parameters determined upon characterization of reconstituted APAP formulations are shown in Table 31.

TABLE 28

|  | WB-4 | WB-7 |
| --- | --- | --- |
| PVP-PLA copolymer (WB-4 or WB-7), mg | 2550 | 2550 |
| Acetaminophen, mg | 450 | 450 |
| Ethanol, mL | 3.00 | 3.00 |
| Water (added before evaporation), mL | 40.00 | 40.00 |
| 0.1N NaOH solution, mL | 0.43 | 0.36 |
| Mannitol (solution of 100 mg/mL), mL | 1.25 | 1.25 |
| Ratio of formulation weight after and before evaporation | 0.20 | 0.37 |
| Water added after evaporation to adjust final APAP concentration to 20 mg/mL, mL | 12.9 | 4.9 |
| Sodium phosphate buffer (100 mM, pH 7.0), mL | 0.50 | 0.50 |

TABLE 29

| Ingredients | mg/vial | %/vial |
| --- | --- | --- |
| Acetaminophen | 100.0 | 14.4 |
| PVP-PLA copolymer WB-4 | 566.7 | 81.4 |
| Mannitol | 27.8 | 4.0 |
| Sodium hydroxide | 0.4 | >0.1 |
| Sodium phosphate monobasic | 0.6 | >0.1 |
| Sodium phosphate dibasic | 0.8 | 0.1 |
| Total | 696.3 mg | 100% |

TABLE 30

| Ingredients | mg/vial | %/vial |
| --- | --- | --- |
| Acetaminophen | 100.0 | 14.4 |
| PVP-PLA copolymer WB-7 | 566.7 | 81.4 |
| Mannitol | 27.8 | 4.0 |
| Sodium hydroxide | 0.3 | >0.1 |
| Sodium phosphate monobasic | 0.6 | >0.1 |
| Sodium phosphate dibasic | 0.8 | 0.1 |
| Total | 696.2 mg | 100% |

TABLE 31

| Parameter | WB-4 | WB-7 |
| --- | --- | --- |
| Reconstitution time (s) | 150 | 55 |
| pH | 7.20 | 7.25 |
| Osmolality (mOsm/kg) | 271 | 281 |
| Optical transmittance (%) | 95.2 | 41.7 |
| Z-average particle size (nm) | 44.3 | 218 |
| Particle size distribution | 0.252 | 0.393 |

Accordingly, DLLs of almost 15% were achieved.

WB-7 was not able to formulate APAP in manner suitable for administration due to the presence of visible and sub-visible particles.

With WB-4, the resulting solution was deemed to possess properties suitable for administration. Further experiments indicated that WB-4 could formulate APAP at a DLL of 18% (90% optical transmittance), 20% (84% optical transmittance), and 25% (78% optical transmittance).

Acetaminophen Formulations with Other Polymers

Given the above success with WB-4, other APAP test formulations were attempted based on the above protocols with polymers WB-5, WB-6, and WB-8 (data not shown). In summary, polymers WB-5, and WB-6 were deemed capable of making nanodispersions of APAP that were suitable to meet requirements for administration.

Celecoxib Formulations

Celecoxib Formulations with Polymer WB-4

Celecoxib (CEL) formulation was prepared as follows. 450 mg of WB-4 block copolymer was dissolved in 1 mL of water for injection under magnetic stirring during ca. 10 minutes. To the polymer solution, 0.4 mL of 0.1N NaOH aqueous solution was added under stirring to bring the pH to approximately 7.5. Next, 0.25 mL of 100 mM sodium phosphate buffer pH 7.0 was added to the solution followed by the addition of 1.25 mL of aqueous solution of mannitol at concentration 100 mg/mL. Next, 50 mg of celecoxib was dissolved in 1 mL of ethanol in glass vial under magnetic stirring at room temperature and added drop by drop to polymer solution during ca. 1 min. Resulting clear solution was cooled down in the ice bath and placed in a cold chamber at 6° C. under stirring for ca. 20 min. After removing the sample from a cold chamber, 1.10 mL of water was added to the formulation. Next, the solution was concentrated during ca. 30 min. to 25% of its initial weight under reduced pressure in a Büchi Collegiate Rotavapor® equipped with a dry ice solvent trap and a Heidolph Rotavac Valve vacuum pump. The temperature of the water bath was maintained at 30-35° C. To the concentrated solution, 3.64 mL of water was added to obtain the formulation of final CEL concentration 10 mg/mL. The formulation was then filtered through 0.2 um Nylon Target2 filters (Thermo Scientific). Filtered formulation was transferred into 10 mL glass vial and freeze-dried using a VirTis Genesis 25EL lyophilizer. The composition of the resulting lyophilized celecoxib cakes is shown in Table 32.

TABLE 32

| Ingredients | mg/vial | %/vial |
|---|---|---|
| Celecoxib | 50.0 | 7.8% |
| PVP-PLA copolymer WB-4 | 450.0 | 70.0% |
| Mannitol | 125 | 19.4% |
| Sodium hydroxide | 1.6 | 0.2% |
| Sodium phosphate monobasic | 7.5 | 1.2% |
| Sodium phosphate dibasic | 8.9 | 1.4% |
| Total | 643 | 100% |

Accordingly, a DLL of almost 8% was achieved.

Figure 12:
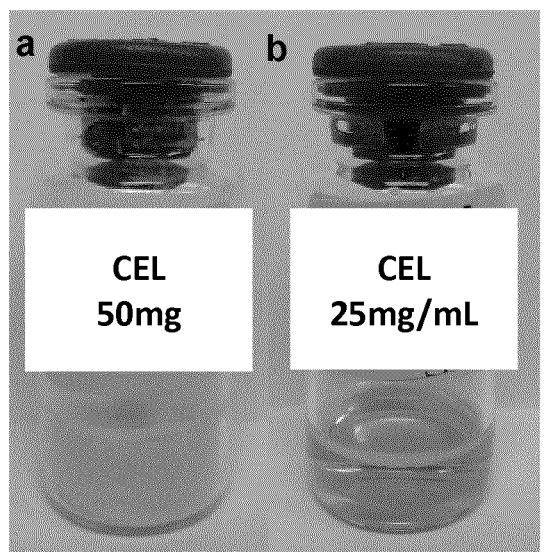
FIG. 12 depicts a picture of the freeze-dried celecoxib cake and the solution obtained after reconstitution of the cake with water for injection at the CEL concentration of 25 mg/mL.

FIG. 12 shows a picture of the freeze-dried cake and the solution obtained after reconstitution of the cake with water for injection at the CEL concentration of 25 mg/mL. The cake shows fine sponge-like structure with no cracking or collapse. Close inspection of the reconstituted liquid (FIG. 12b) confirms the clarity of solution and the absence of visible solid particles.

Figure 13:
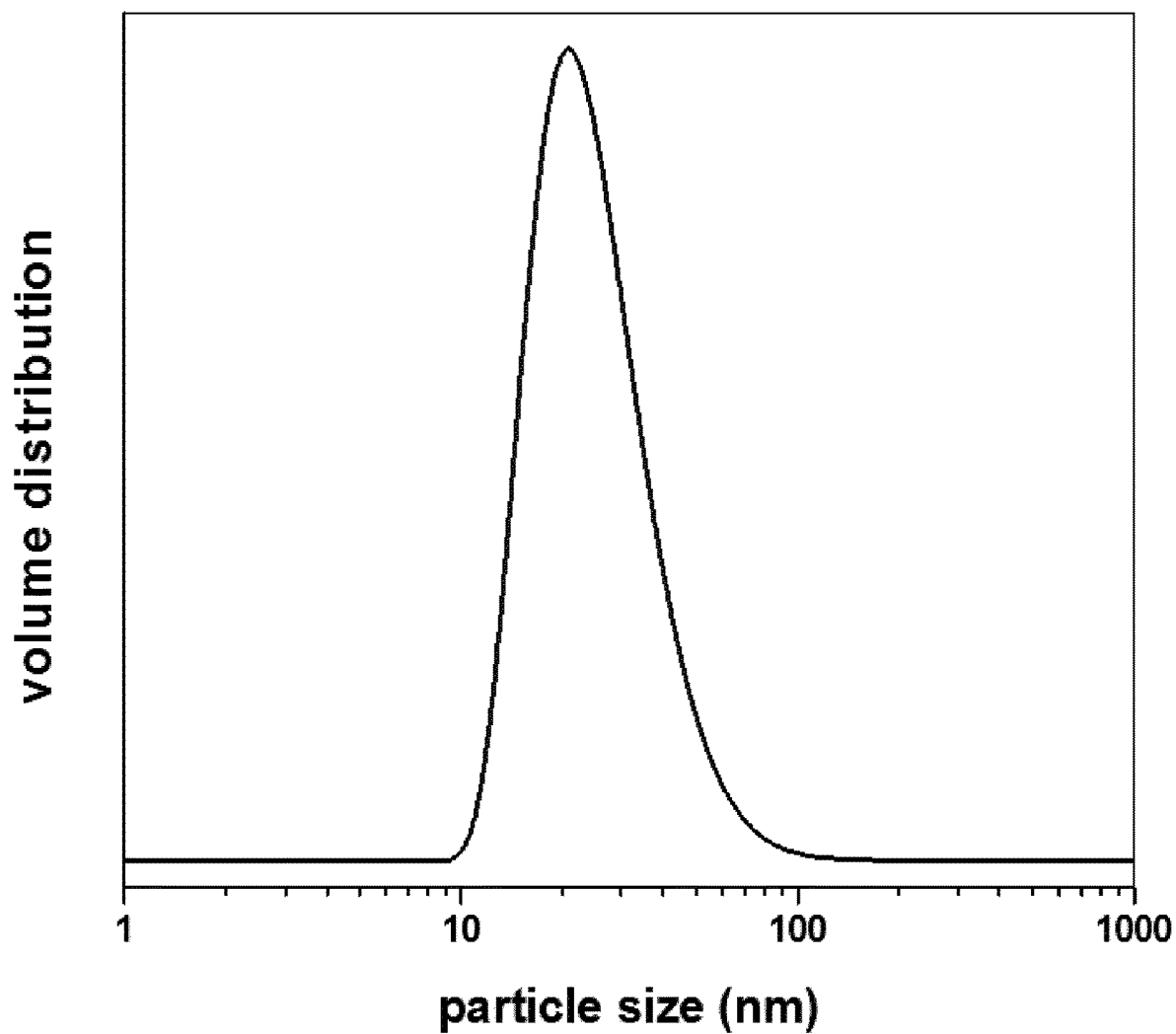
FIG. 13 depicts particle size distribution for celecoxib formulation reconstituted at 25 mg/mL.

Lyophilized cakes undergo dissolution in water in less than 1 min to give clear, particle-free solutions having celecoxib concentration of 25 mg/mL. pH of the reconstituted solutions was in the range from 6.8 to 7.2 as measured using an Accumet AP61 pH-meter equipped with a gel-filled epoxy-body combination electrode. Optical transmittance was determined in 1-cm disposable polystyrene cuvettes on an Agilent Cary UV-Vis-NIR 5000 spectrometer. The measurements were performed at 650 nm and room temperature using empty cuvette as a blank. The reconstituted mixtures had optical transmittance of around 92%. Osmolality of reconstituted samples was measured with a freezing point depression 3300 Micro-Osmometer (Advanced Instruments) and it was in the range of 420 to 450 mOsm/kg. Z-average size of micelles and their size distribution was determined at 25° C. by dynamic light scattering using a Malvern Zetasizer Nano ZS equipped with 10 mW He—Ne laser operating at 633 nm. Z-average particle size and its polydispersity varied from 47 to 52 nm and from 0.38 to 0.45, respectively. FIG. 13 shows that particle size distribution for celecoxib formulation reconstituted at 25 mg/mL is monomodal and that the volume-average size of micelles varies from ca. 10 to ca. 200 nm.

Celecoxib Formulations with Other Polymers

Given the above success with WB-4, other CEL test formulations were attempted with polymers WB-5 to WB-8 based on the above protocols (data not shown). In summary, polymers WB-5, WB-6, and WB-8 were deemed capable of making nanodispersions of CEL that were suitable to meet requirements for administration.

Propofol Formulations

Propofol (PPF) formulations were prepared as follows. 900 mg of PVP-PLA polymer (WB-4, WB-5, WB-6, WB-7, and WB-8) was dissolved in 7.5 mL of 100 mM phosphate buffer pH 7.0 in a glass vial under stirring at room temperature for approximately 10 minutes following the addition of 100 mg (107 uL) of PPF. Solutions were kept under vigorous stirring at room temperature for approx. 16 h followed by addition of 2.5 mL of water. FIG. 1 shows the pictures of the formulations before filtration. Size distribution of the particles obtained before filtration is shown in FIG. 2. Formulations prepared using polymers WB-4, WB-5, and WB-6 are homogenous and transparent solutions. They show monomodal particle size distribution with the Z-average size of 33 to 44 nm. These formulations were subsequently filtered through 0.2 um Nylon Target2 filters (Thermo Scientific), transferred into 5 mL glass vials by 2 mL aliquots and freeze-dried using a VirTis Genesis 25EL lyophilizer. In contrast, samples prepared using polymers WB-7 and WB-8 polymers show bimodal size distribution and z-average size of ca. 120 nm, they cannot be filtered using 0.2 um filters and were not analyzed any further.

Figure 14:
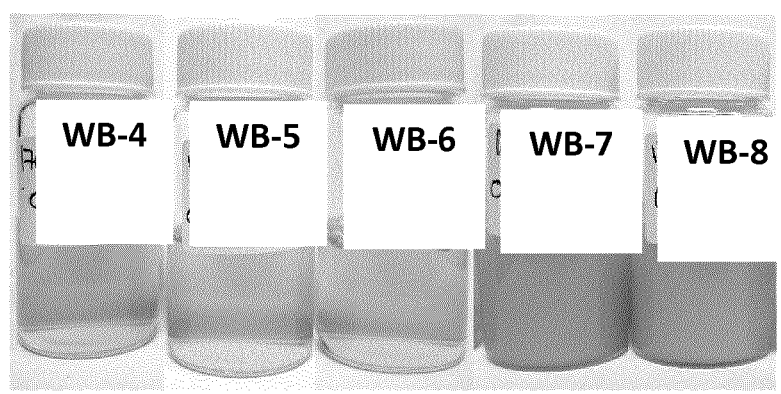
FIG. 14 depicts a photograph of formulations of PPF prepared with WB-4 to WB-8 polymer samples before filtration and freeze-drying.

FIG. 14 depicts a photograph of formulations of PPF prepared with WB-4 to WB-8 polymer samples before filtration and freeze-drying, with WB-4 to WB-6 producing relatively clear solutions.

Figure 15:
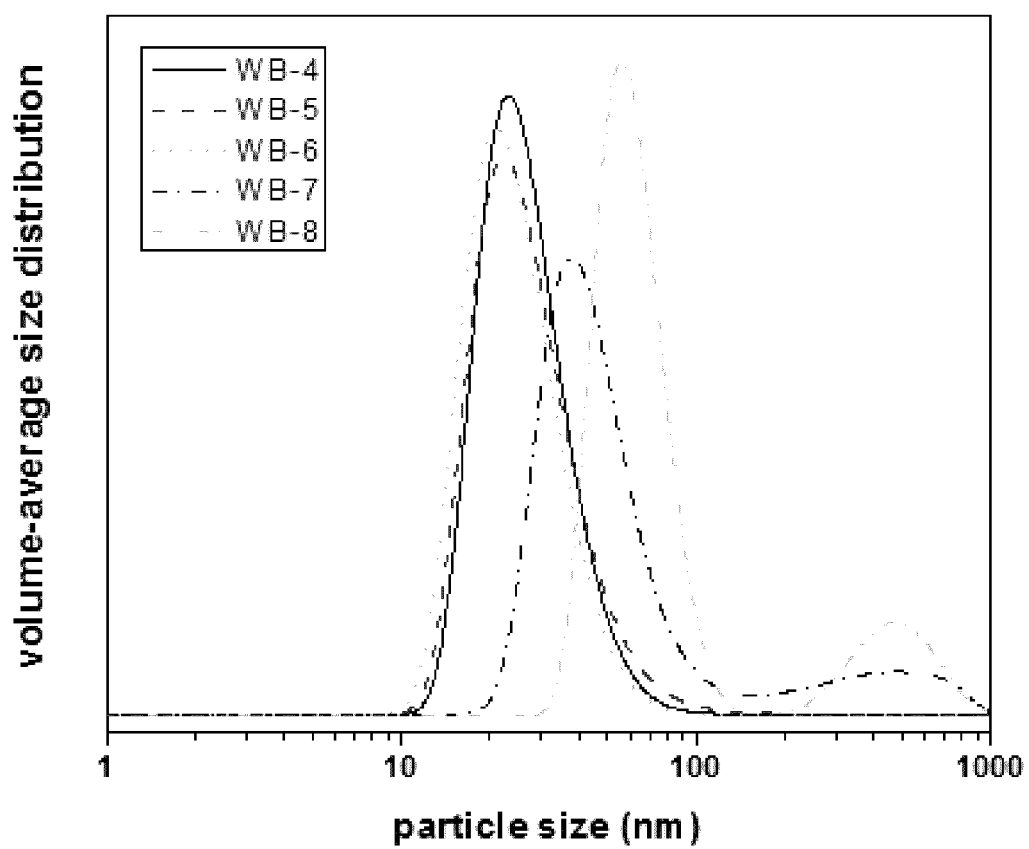
FIG. 15 depicts volume-average size distribution of particles in formulations of PPF and polymers WB-4 to WB-8 before filtration and freeze-drying.

FIG. 15 depicts volume-average size distribution of particles in formulations of PPF and polymers WB-4 to WB-8 before filtration and freeze-drying.

Freeze-dried cakes (20 mg of PPF) were reconstituted with 2 water in less than 1 min. upon gentle shaking to give clear, particle-free solutions having PPF concentration of 10 mg/mL. Table 2 shows physicochemical properties of reconstituted formulations. pH of reconstituted solutions was 7.02-7.03 as measured using an Accumet AP61 pH-meter equipped with a gel-filled epoxy-body combination electrode. Optical transmittance was determined in 1-cm disposable polystyrene cuvettes on an Agilent Cary UV-Vis-NIR 5000 spectrometer. The measurements were performed at 650 nm and room temperature using empty cuvette as a blank. The reconstituted mixtures had optical transmittance between ca. 77 and 83%. Osmolality of reconstituted samples was measured with a freezing point depression 3300 Micro-Osmometer (Advanced Instruments) and it was in the range of 188 to 223 mOsm/kg. Z-average size of micelles and their size distribution was determined at 25° C. by dynamic light scattering using a Malvern Zetasizer Nano ZS equipped with 10 mW He—Ne laser operating at 633 nm. Z-average particle size varied from 43.5 to 58.7 nm.

Figure 16:
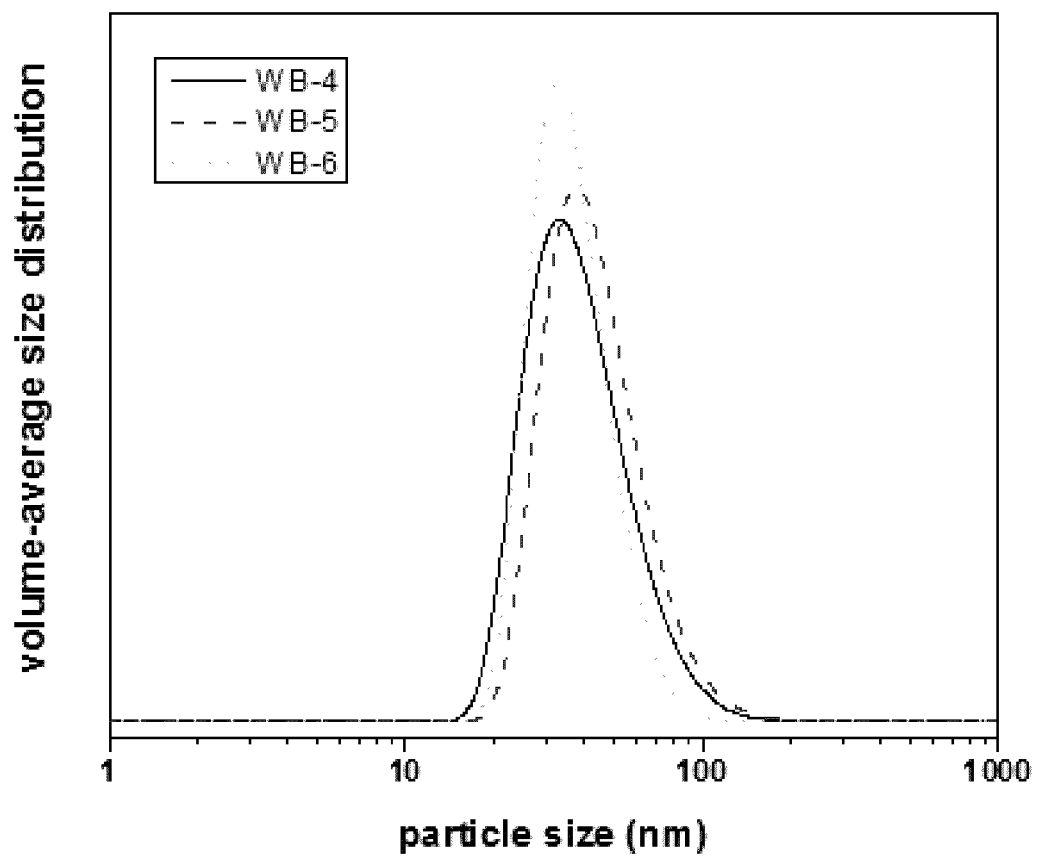
FIG. 16 shows that particle size distribution for PPF formulations prepared using polymers WB-4, WB-5, and WB-6 is monomodal and that the volume-average size of micelles varies from ca. 15 to 150 nm.

FIG. 16 shows that particle size distribution for PPF formulations prepared using polymers WB-4, WB-5, and WB-6 is monomodal and that the volume-average size of micelles varies from ca. 15 to 150 nm.

Table 33 depicts physicochemical characterization of PPF formulations prepared with WB-4, WB-5, and WB-6 polymer samples and reconstituted at 10 mg/mL.

TABLE 33

| | Polymer batch used in formulation | | |
|---|---|---|---|
| | WB-4 | WB-5 | WB-6 |
| Z-average size (nm) | 52.2 | 58.7 | 43.5 |
| pH | 7.02 | 7.03 | 7.03 |
| Optical transmittance (% T) | 77.0 | 83.1 | 83.0 |
| Osmolality (mOsm/kg) | 201 | 223 | 188 |

All three formulations were suitable for administration.

Summary

Table 34 briefly summarizes formulation results, indicating which polymers successfully formulated (Y) which APIs, and which did not (N).

TABLE 34

| | FLU | APAP | CEL | PPF |
|---|---|---|---|---|
| WB-DMAP | Y | | | |
| WB-1 | Y | | | |
| WB-2 | Y | | | |
| WB-3 | Y | | | |
| WB-4 | Y | Y | Y | Y |
| WB-5 | Y | Y | Y | Y |
| WB-6 | Y | Y | Y | Y |
| WB-7 | Y | N | N | |
| WB-8 | Y | N | Y | |

Discussion

PVP-PLA block copolymers described herein have been used to increase the water solubility of a range of drug molecules many thousand fold, and to produce solid products that reconstitute rapidly in aqueous solution to generate very high concentration, low viscosity liquids. Further these formulations have been lyophilized to optimize their stability at both room temperature and elevated temperatures as could occur from time to time. These copolymers are able to achieve DLL and concentrations in solution that are suitable for delivery.

The polymers can be classified in terms of their ability to formulate APIs as follows.

Group 1 polymers have been show to effectively formulate at least one API, i.e. FLU as a micellar composition suitable for delivery to a subject. These include WB-1 to WB-8. WB-DMAP may also be included in this group.

Group 2 polymers have been show to effectively formulate at least two APIs, i.e. FLU and CEL. WB-4 to WB-6 and WB-8 are included in this group. WB-1 to WB-3 were not tested, but should are included due to similar properties.

Group 3 polymers have been shown to effectively formulate at least three APIs. In fact, they also formulate all four that were tested, i.e. FLU, CEL, APAP, and PPF. WB-4 TO WB-6 are included in this group. Again, WB-1 to WB- are also included due to similar properties.

Group 4 polymer may be thought of as a subset of Group 3 that has been subject to the most rigorous testing, and includes WB-4 TO WB-6.

These groups are listed in Table 20, wherein minimum, maximum, and average values for various parameters have been listed for the groups. Trends are apparent in this data, with narrowed ranges or different average values across Groups 1 through 4 being indicative of unexpected increases in flexibility. Design parameters could be readily selected from within these ranges to generate polymers having desired characteristics. Selection of target variables for block-copolymers will depend on requirements, e.g. if it is desired to select a block co-polymer based on ability to solubilize a specific API, or whether a flexible drug-delivery platform is preferred.

Example 4: Pharmacokinetic Study

Introduction

The present study examined the pharmacokinetics (PK) of flurbiprofen (FLU) formulated using SmartCelle micellar nanotechnology (PPI-1501) after intravenous (IV) delivery to rats as described in JRF Report: Single Dose Pharmacokinetic study of Flurbiprofen Formulation through Intravenous Route in Wistar Rats; JRF International—September 2016. FLU pharmacokinetics as presented in the report were fitted using both non-compartmental and two compartment models to assess goodness of fit.

The fitted results obtained in the JRF study were then compared to those in the literature, generated after administering a non-micellar low concentration simple FLU solution IV to rats. This was undertaken to determine potential differences in FLU pharmacokinetics induced by the micellar formulation.

Both sets of rodent data were then extrapolated using published human FLU PK parameters to estimate the PK of FLU post IV administration of PPI 1501 or non-formulated FLU to humans.

Finally the predicted FLU pharmacokinetics following PPI-1501 administration to humans were compared to those generated by the IV administration of the FLU pro-drug flurbiprofen axetil (FA) to humans. The impact of the micellar formulation on FLU pharmacodynamics compared to a simple solution or the pro-drug were then assessed.

Methods

As per the JRF protocol, Wistar rats were dosed with reconstituted PPI 1501 by intravenous injection over 15 seconds via the jugular vein at 3 doses these being; 2.5 mg/kg, 10 mg/kg and 30 mg/kg. These doses were selected to produce exposures in rats encompassing potential human therapeutic doses, taking into account the differences in clearance rate between rats and humans.

Blood samples were collected from 3 rats at the following time points: 2, 15, 30, mins, and 1, 2, 4, 6, 12, and 24 hours. Each rat was sampled 2 times from the jugular vein.

Results

Variability

Figure 17:
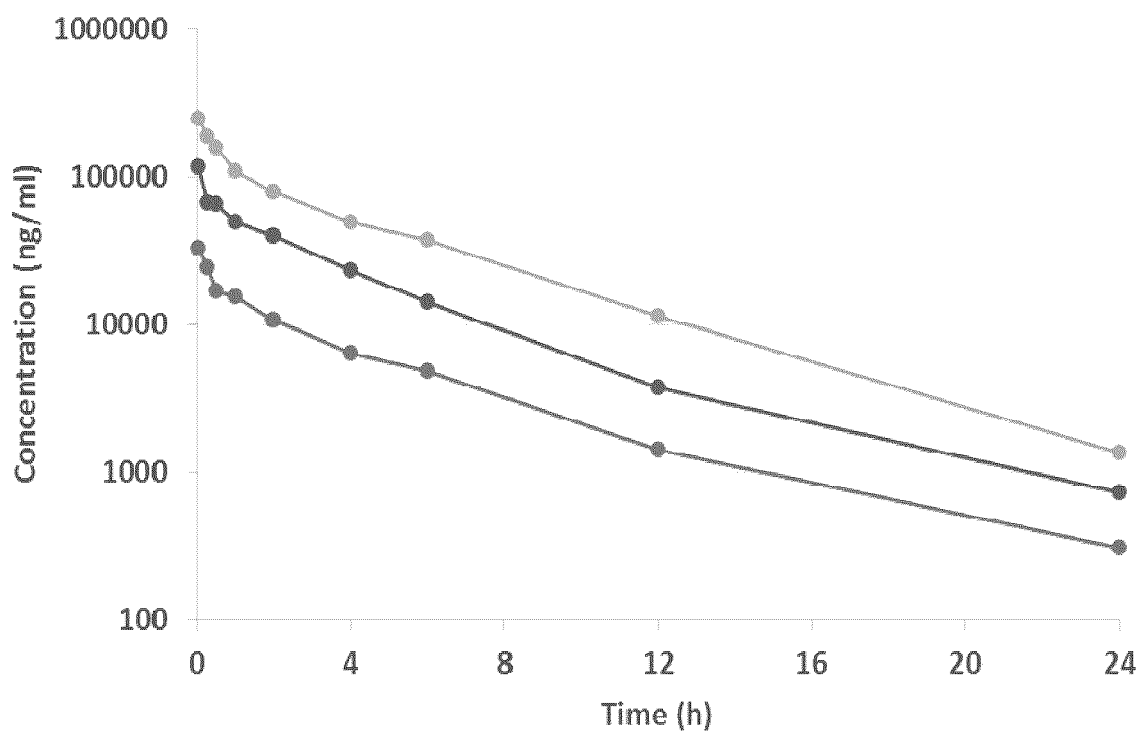
FIG. 17 depicts time concentration profiles of FLU fin rats following an IV dose of 2.5 (lower line), 10 (middle line) or 30 mg/kg (upper line) PPI-1501.

The time-concentration profiles of FLU generated by the PPI 1501 formulation are summarized in Tables 35-37 and FIG. 17.

TABLE 35

Time concentration profile of FLU in the rats following an IV dose of 2.5 mg/kg PPI-1501

| Time (h) | Mean | SD | CV % |
|---|---|---|---|
| 0.033 | 32711.7 | 5254.8 | 16.1 |
| 0.25 | 24044.5 | 4245.6 | 17.7 |
| 0.50 | 16917.7 | 3666.3 | 21.7 |
| 1 | 15327.0 | 126.9 | 0.8 |
| 2 | 10691.6 | 452.0 | 4.2 |
| 4 | 6349.6 | 1002.5 | 15.8 |
| 6 | 4823.7 | 580.8 | 12.0 |
| 12 | 1422.0 | 292.3 | 20.6 |
| 24 | 308.4 | 26.1 | 8.5 |

TABLE 36

Time concentration profile of FLU in the rats following an IV dose of 10 mg/kg PPI-1501.

| Time (h) | Mean | SD | CV % |
|---|---|---|---|
| 0.033 | 116699.1 | 3811.8 | 3.3 |
| 0.25 | 66360.2 | 20807.0 | 31.4 |
| 0.5 | 64874.4 | 6517.0 | 10.0 |
| 1 | 49676.0 | 5011.7 | 10.1 |
| 2 | 39275.7 | 2915.4 | 7.4 |
| 4 | 23363.5 | 2819.5 | 12.1 |
| 6 | 14256.6 | 4141.6 | 29.1 |

TABLE 36-continued

Time concentration profile of FLU in the rats
following an IV dose of 10 mg/kg PPI-1501.

| Time (h) | Mean | SD | CV % |
|---|---|---|---|
| 12 | 3710.3 | 688.9 | 18.6 |
| 24 | 723.7 | 667.9 | 92.3 |

TABLE 37

Time concentration profile of FLU in the rats
following an IV dose of 30 mg/kg PPI-1501.

| Time (h) | Mean | SD | CV % |
|---|---|---|---|
| 0.033 | 250167.4 | 39639.2 | 15.8 |
| 0.25 | 188737.7 | 6123.3 | 3.2 |
| 0.5 | 156477.7 | 7084.9 | 4.5 |
| 1 | 109774.2 | 12488.7 | 11.4 |
| 2 | 79479.2 | 4120.6 | 5.2 |
| 4 | 49066.4 | 1650.1 | 3.4 |
| 6 | 37523.6 | 3727.7 | 9.9 |
| 12 | 11361.0 | 2090.2 | 18.4 |
| 24 | 1350.8 | 595.5 | 44.1 |

FIG. 17 itself depicts time concentration profiles of FLU fin rats following an IV dose of 2.5 (lower line), 10 (middle line) or 30 mg/kg (upper line) PPI-1501.

The inter-animal variability (CV) for most time-points were within 20%. Greater degrees of variation were only seen at later time points when levels of FLU were closer to the levels of quantitation of the bio-assay.

Linearity

The data were first analysed using a standard non-compartmental model, results being summarized in Table 38.

TABLE 38

IV PK parameters of FLU from PPI1501 based on
standard non-compartmental analysis (NCA)

| Parameter | 2.5 mg/kg | 10 mg/kg | 30 mg/kg |
|---|---|---|---|
| t½ (h) | 4.55 | 4.05 | 3.81 |
| Cmax (ng/ml) | 32712 | 116699 | 250167 |
| $C_0$ (ng/ml) | 34298 | 127287 | 261251 |
| $AUC_t$ (ng/ml*h) | 90790 | 294180 | 698474 |
| $AUCi_{nf}$ (ng/ml*h) | 92814 | 298404 | 705906 |
| MRT (h) | 5 | 4 | 5 |
| Vz (ml/kg) | 177 | 196 | 234 |
| CL (ml/h/kg) | 27 | 34 | 42 |
| Vss (ml/kg) | 138 | 150 | 198 |

TABLE 38-continued

IV PK parameters of FLU from PP11501 based on
standard non-compartmental analysis (NCA)

| Parameter | 2.5 mg/kg | 10 mg/kg | 30 mg/kg |
|---|---|---|---|
| $C_0$/Dose | 13719 | 12729 | 8708 |
| AUC 0-t/D | 36316 | 29418 | 23282 |
| AUC 0-inf/D_obs | 37126 | 29840 | 23530 |

The dose-normalized plasma concentrations at time 0 ($C_0$) and $AUC_{inf}$ at the 10 mg/kg dose were 93% and 80% respectively of those observed at 2.5 mg/kg while values for these parameters for the 30 mg/kg dose were both only 63% of those seen at the 2.5 mg/kg dose. These data suggest acceptable dose linearity at doses between 10 mg/kg and 2.5 mg/kg but a reduction in exposure with increasing dose.

For this reason comparisons with rodent intravenous solution data and extrapolations to potential human results shown later in this report were performed with the 2.5 mg/kg rat data only. As the predicted human dose of PPI-1501 is 100 mg BID (see below) 2.5 mg/kg represents the upper range of the potential treatment regimen (175 mg for a 70 kg individual).

The results from the JRF study were then compared to literature values for FLU PK administered as an IV solution as generated by Park and Kim (1) and Knihinicki et al (2); the comparison is shown in Table 39.

TABLE 39

Differences of NCA PK parameters between FLU in PPI
1501 versus solutions at an IV dose of 2.5 mg/kg

| Parameter | PPI 1501 | Park & Kim | Ratio PPI-1501 to Park & Kim | Knihinicki et al | Ratio PPI-1501 to Knihinicki | Park & Kim/ Knihinicki |
|---|---|---|---|---|---|---|
| $t_{1/2}$ (h) | 4.55 | 2.78 | 1.64 | 3.07 | 1.48 | 0.91 |
| MRT (h) | 5.11 | 3.40 | 1.50 | 4.07 | 1.26 | 0.83 |
| CL (ml/min/kg) | 26.94 | 47.94 | 0.56 | 54 | 0.50 | 0.88 |
| Vss (ml/kg) | 137.76 | 156.78 | 0.88 | 220 | 0.63 | 0.72 |
| $AUC_{inf}$ (ng/ml*h) | 92814 | 54080 | 1.72 | 46296 | 2.00 | 1.17 |
| Vz (ml/kg) | 177 | 192.31 | 0.92 | 239 | 0.74 | 0.8 |

As may be seen, rodent PK results obtained separately for a simple low dose FLU solution by Park and Kim or Knihinicki were similar for all parameters measured (differences 0.72 to 1.17) indicating that an inter-study meta-analysis, while not providing absolute comparative data, is acceptable for identifying significant differences between administration of FLU in micellar and non-micellar forms. Parameters where considerable differences occurs between simple solution and micellar delivery are highlighted Thus, when comparing simple solution values with those obtained with the micellar formulation a number of differences are evident;

1. The half-life (t1/2) of FLU delivered by PPI-1501 is considerable greater than when administered as a solution.

2. The mean residence time (MRT) of FLU delivered by PPI-1501 is greater than when administered as a solution.

3. The clearance rate (CL) of FLU delivered by PPI-1501 is considerable slower than when administered as solution.

4. Most importantly the exposure of the rats to FLU (AUCinf) is very considerably greater when FLU is administered in a micellar form.

Figure 18:
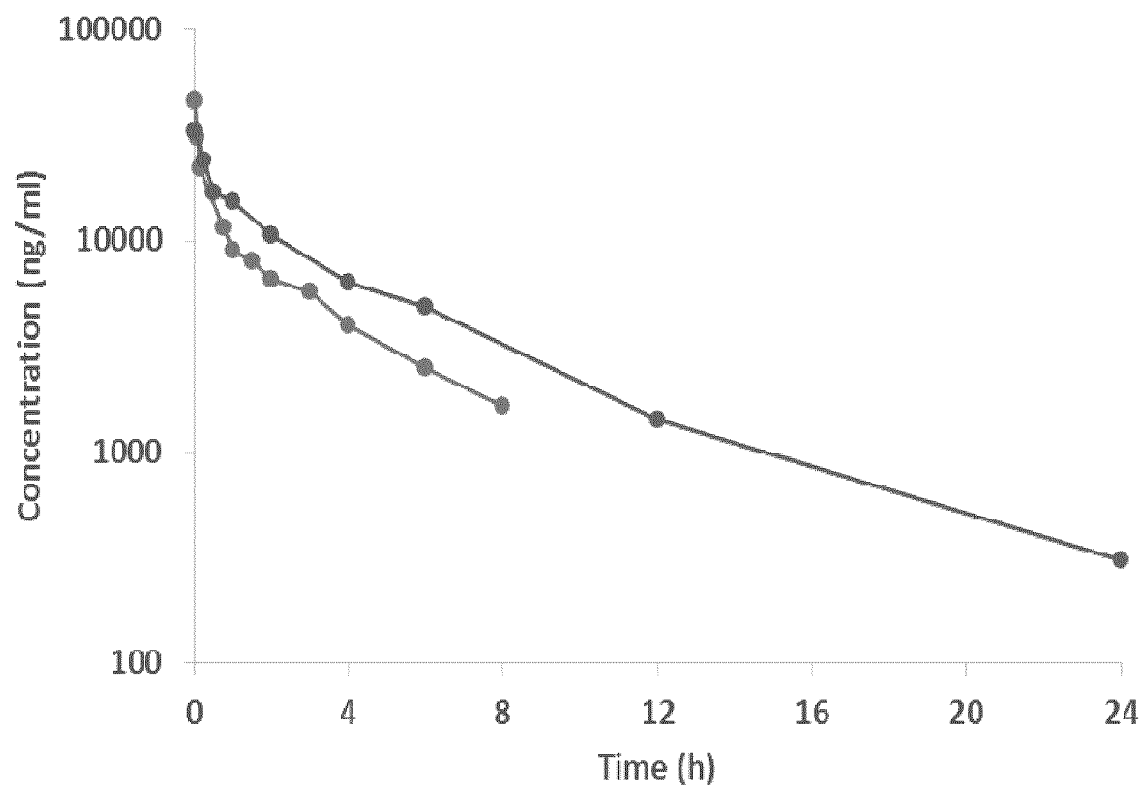
FIG. 18 depicts a comparative plasma time-concentration profiles of FLU following the IV dosing of a 2.5 mg/kg FLU solution (redrawn from Reference 1; bottom line) and following IV dosing of PPI-1501 at 2.5 mg/kg (top line).

FIG. 18 depicts a comparative plasma time-concentration profiles of FLU following the IV dosing of a 2.5 mg/kg FLU solution (redrawn from Reference 1; bottom line) and following IV dosing of PPI-1501 at 2.5 mg/kg (top line). Results across the test period highlight the more rapid clearance of FLU when administered as a solution and also the lower Cmax achieved when FLU is administered in micellar form. Note the more rapid initial clearance/redistribution of FLU when administered as a simple solution. In conclusion, administration in micellar form appears to increase the exposure of the rats to FLU.

Analysis using a Two Compartment Model

Figure 19:
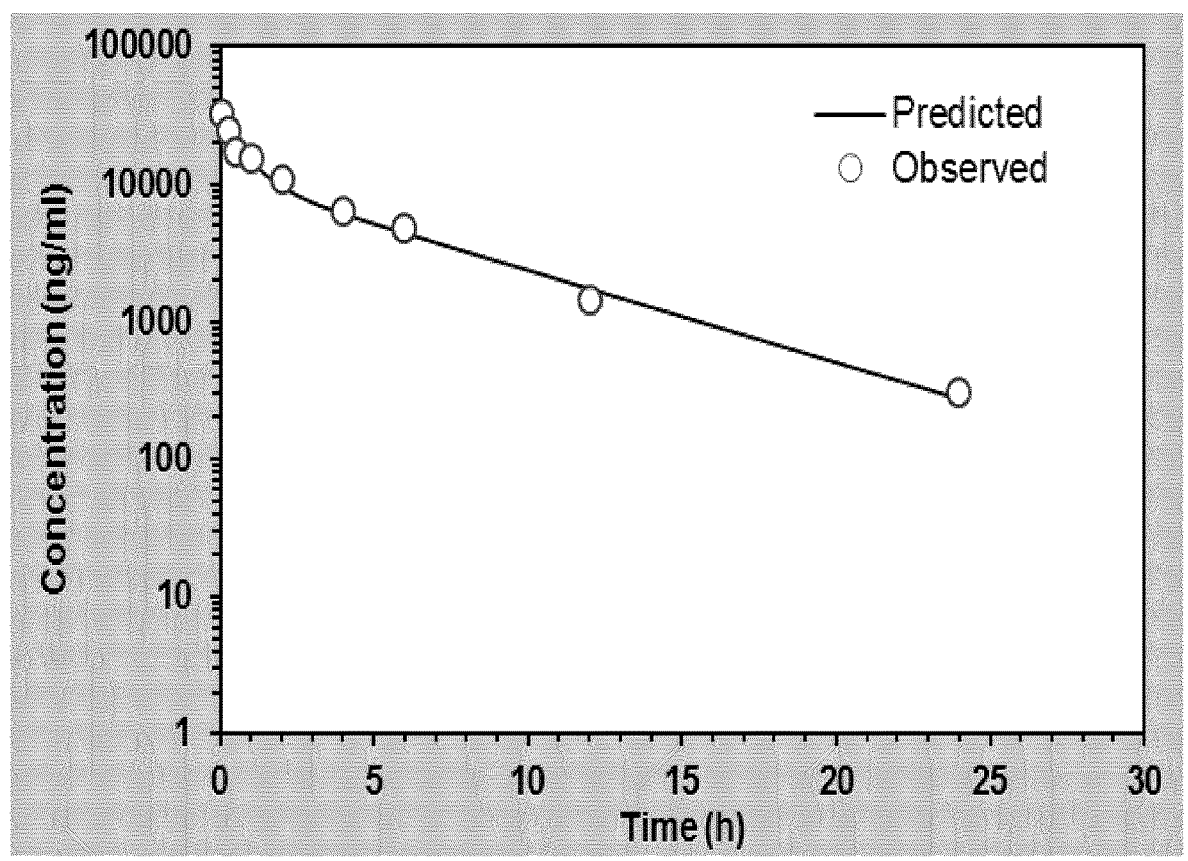
FIG. 19 depicts two compartmental model fitting of the plasma concentration profile of FLU dosed as PPI 1501 at the IV dose of 2.5 mg/kg.
Figure 20:
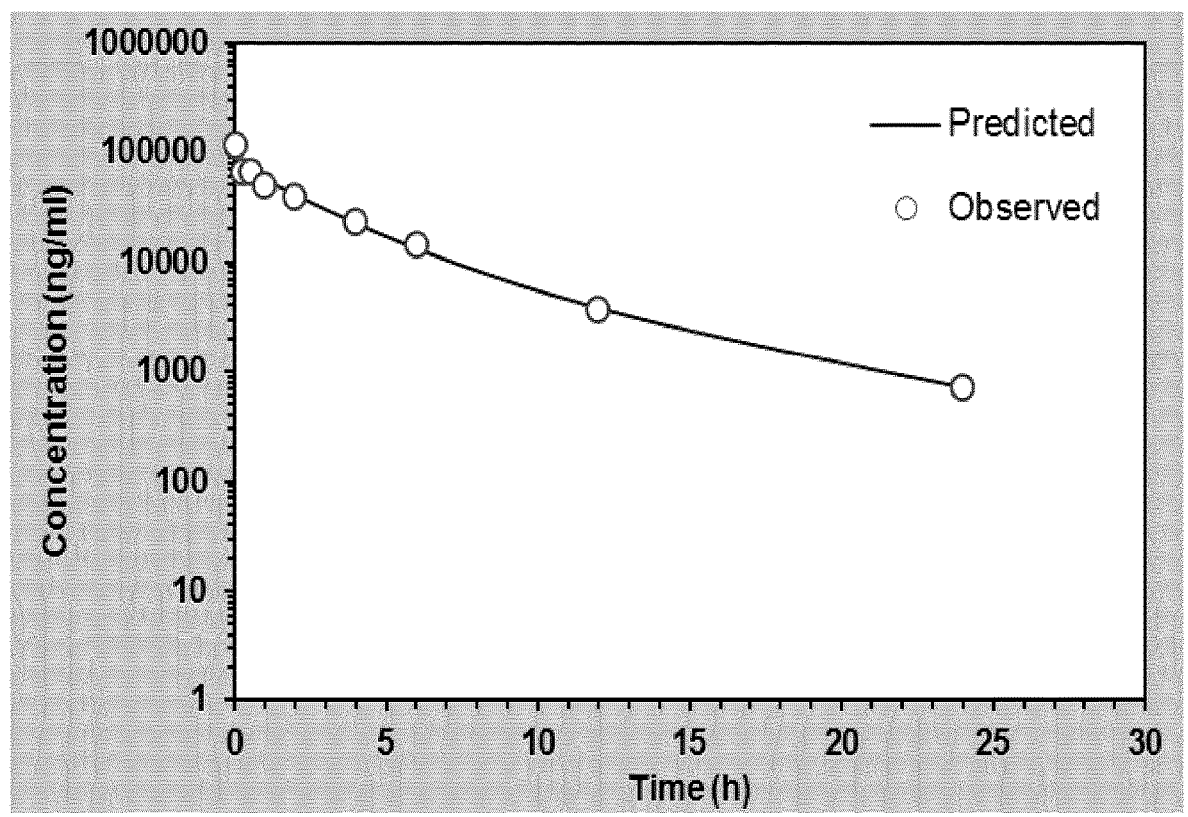
FIG. 20 depicts two compartmental model fitting of the plasma concentration profile of FLU dosed as PPI 1501 at the IV dose of 10 mg/kg.

While NCA was employed earlier to allow comparison of rodent data generated using PPI-1501 to literature simple solution data, more recent reports indicate that FLU in both the clinic and in rodents is better fitted using a 2 compartmental model (2-8). FIGS. 18-20 therefore present the JRF data fitted using a 2 compartmental model.

FIG. 19 depicts two compartmental model fitting of the plasma concentration profile of FLU dosed as PPI 1501 at the IV dose of 2.5 mg/kg.

FIG. 20 depicts two compartmental model fitting of the plasma concentration profile of FLU dosed as PPI 1501 at the IV dose of 10 mg/kg.

Figure 21:
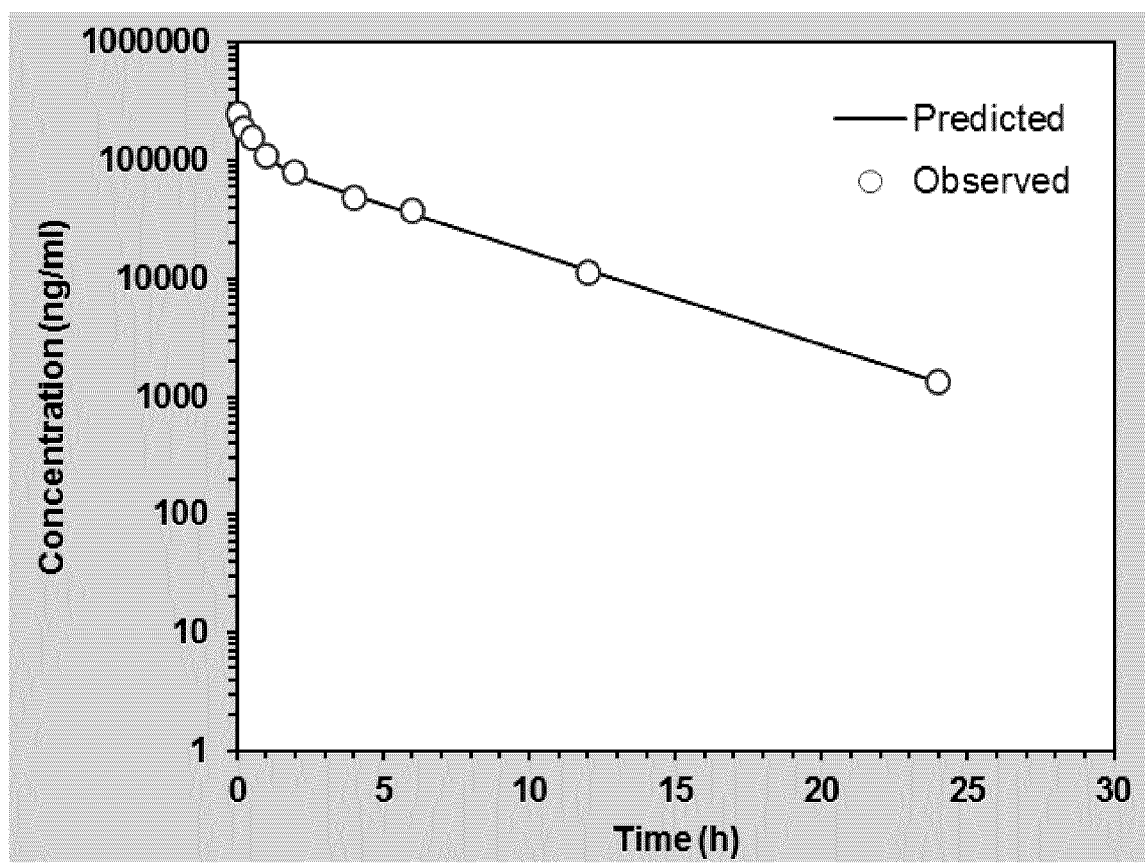
FIG. 21 depicts two compartmental model fitting of the plasma concentration profile of FLU dosed as PPI 1501 at the IV dose of 30 mg/kg.

FIG. 21 depicts two compartmental model fitting of the plasma concentration profile of FLU dosed as PPI 1501 at the IV dose of 30 mg/kg.

Table 40 shows the PK parameters that are generated.

TABLE 40

Two compartmental PK data analysis based on data in Table 21

| Parameter | Unit | 2.5 mg/kg | 10 mg/kg | 30 mg/kg |
|---|---|---|---|---|
| A | ng/ml | 18256.1 | 64288.1 | 149620.5 |
| Alpha | 1/h | 1.26 | 0.37 | 1.90 |
| B | ng/ml | 11044.7 | 13348.7 | 105955.4 |
| Beta | 1/h | 0.15 | 0.12 | 0.18 |
| $k_{10}$ | 1/h | 0.34 | 0.28 | 0.39 |
| $k_{12}$ | 1/h | 0.51 | 0.05 | 0.80 |
| $k_{21}$ | 1/h | 0.57 | 0.17 | 0.90 |
| $t_{1/2}$ Alpha | h | 0.55 | 1.86 | 0.36 |
| $t_{1/2}$ Beta | h | 4.50 | 5.67 | 3.80 |
| C0 | ng/ml | 29300.8 | 77636.9 | 255575.9 |
| V | (ml/kg) | 85.3 | 128.8 | 117.4 |
| CL | (ml/kg/h) | 29.0 | 35.5 | 45.5 |
| V2 | (ml/kg) | 75.3 | 42.1 | 105.1 |
| CL2 | (ml/kg/h) | 43.1 | 7.0 | 94.1 |
| AUC 0-t | ng/ml*h | 84305.2 | 276029.5 | 652178.0 |
| AUC 0-inf | ng/ml*h | 86075.0 | 281876.3 | 659466.1 |
| MRT | h | 5.5 | 4.8 | 4.9 |
| Vss | (ml/kg) | 160.6 | 170.9 | 222.5 |

Figure 22:
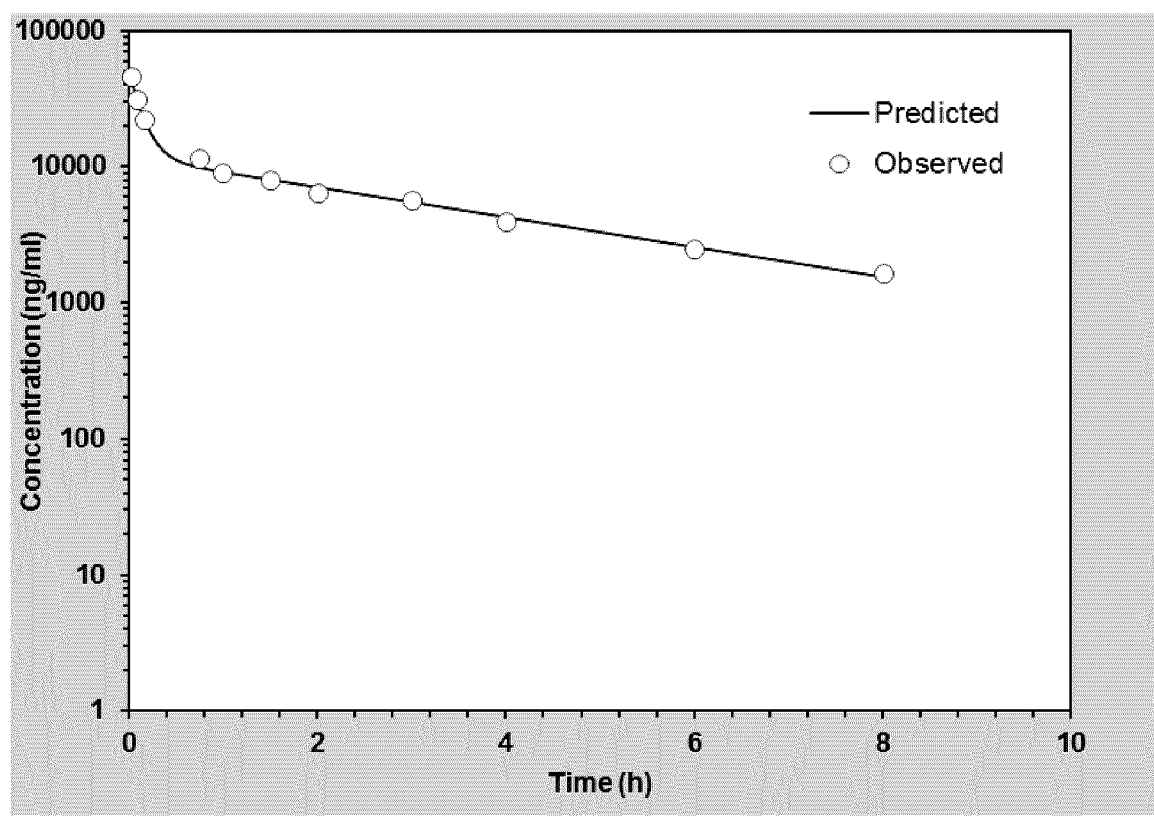
FIG. 22 depicts two compartmental model fitting of the plasma concentration of FLU dosed as a simple solution at the IV dose of 2.5 mg/kg.

For comparative purposes, the rat PK data for a FLU solution generated by Park and Kim (1) were also fitted to the 2 compartmental model (FIG. 22 and Table 41).

FIG. 22 depicts two compartmental model fitting of the plasma concentration of FLU dosed as a simple solution at the IV dose of 2.5 mg/kg. Note the more pronounced and rapid initial redistribution phase of the FLU solution compared to FLU from PPI-1501.

Comparison of the IV profile between FLU in PPI 1501 vs FLU in solution revealed a lower initial concentration and a slower alpha distribution phase, for the micellar product, mostly likely due to retarded release of FLU from the PPI 1501 micelles compared to the simple solution. In contrast, the elimination constant for FLU formulated as PPI-1501 in the beta phase was slower than that when FLU was administered as a solution. These values in turn led to the higher V (by 70%) but lower V2 (by 39%) for FLU from PPI 1501 and the 40% and 92% lower CL and CL2 for the micellar formulation.

TABLE 41

Estimated 2 compartmental PK parameters of FLU in solution (2.5 mg/kg) and differences of parameter values between FLU in PPI 1501 (2.5 mg/kg)

| Parameter | Unit | PPI 1501 | Reported Solution | Ratio |
|---|---|---|---|---|
| A | ng/ml | 18256.14 | 38065.32 | 0.48 |
| Alpha | 1/h | 1.26 | 7.53 | 0.17 |
| B | ng/ml | 11044.66 | 11751.39 | 0.94 |
| Beta | 1/h | 0.15 | 0.25 | 0.61 |
| k10 | 1/h | 0.34 | 0.97 | 0.35 |
| k12 | 1/h | 0.51 | 4.84 | 0.10 |
| k21 | 1/h | 0.57 | 1.97 | 0.29 |
| t½Alpha | h | 0.55 | 0.09 | 5.96 |
| t½Beta | h | 4.50 | 2.73 | 1.64 |
| C0 | ng/ml | 29300.80 | 49816.71 | 0.59 |
| V | (ml/kg) | 85.32 | 50.18 | 1.70 |
| CL | (ml/kg/h) | 29.04 | 48.62 | 0.60 |
| V2 | (ml/kg) | 75.29 | 123.42 | 0.61 |
| CL2 | (ml/kg/h) | 43.10 | 243.11 | 0.18 |
| AUC 0-t | ng/ml*h | 84305.19 | 45317.51 | 1.86 |
| AUC 0-inf | ng/ml*h | 86074.99 | 51421.86 | 1.67 |
| MRT | h | 5.53 | 3.57 | 1.55 |
| Vss | (ml/kg) | 160.61 | 173.60 | 0.93 |

Parameters in shaded boxes cells are the most critical for influencing the time-concentration profile of FIG. 22. Findings are similar to those when non-compartmental analysis was used.

Extrapolations to Human PK and PD Performance

Assuming the plasma PK profile of FLU mediated by IV PPI 1501 in the rat is translatable to human, i.e. that the same PK parameter difference ratios for FLU in PPI 1501 observed in the rat apply in humans, then the human IV PK parameters for FLU in PPI 1501 can be estimated. This may be achieved by simple multiplication of the difference ratios provided in Table 41 (last column) to again obtain the comparative human PK parameter values FLU in PPI 1501 versus those obtained from injection of the simple solution; such data may also be compared to data obtained by injecting humans with the prodrug FA (Table 42).

The human IV PK parameters of FLU in solution were estimated based on the oral PK parameters of FLU and its estimated oral bioavailability (project 1 report, Duan, 2015, Table 42, ref 3-8). From Table 10, it is clear that the estimated MRT following the IV dose of FLU in PPI 1501 is >2-fold of FLU in solution and IV dosed FA (Table 42), attributable to the increased V and decreased CL.

TABLE 42

Estimated 2 compartmental human iv PK parameters of FLU in PPI 1501 in human assuming the same difference ratio of critical 2 compartmental values observed in rats applies to human

| | | Estimated in solution* | Estimated in PP11501 | FA** |
|---|---|---|---|---|
| Ka | 1/h | | | 58 |
| V | L | 4.984 | 8.474 | 5.11 |
| CL | L/h | 0.967 | 0.578 | 1.14 |
| V2 | L | 2.199 | 1.341 | 3.28 |

TABLE 42-continued

Estimated 2 compartmental human iv PK parameters of FLU in PPI 1501 in human assuming the same difference ratio of critical 2 compartmental values observed in rats applies to human

|  |  | Estimated in solution* | Estimated in PP11501 | FA** |
|---|---|---|---|---|
| CL2 | L/h | 0.343 | 0.061 | 4.40 |
| MRT (est. based on 2 compartment model) | h | 7.43 | 16.99 | 7.36 |

*estimated based on literature reported oral PK of FLU and estimated oral bioavailability (report for project 1)
**values from project 1 report.

Figure 23:
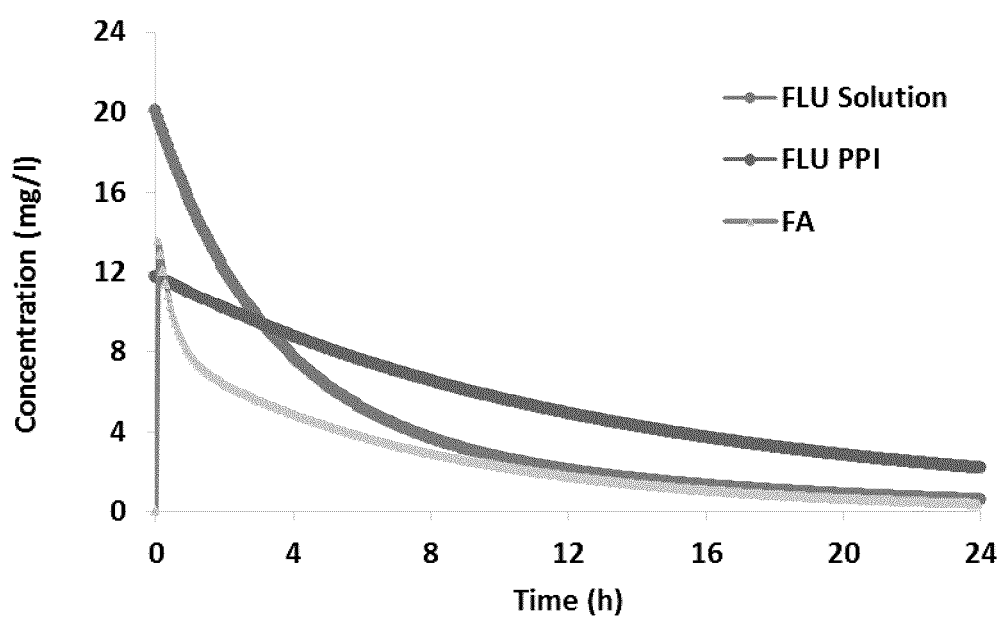
FIG. 23 depicts comparative simulation of human FLU concentration following a single IV dose of 100 mg FLU in solution vs PPI 1501 formulation and FA. The horizontal line corresponding to 4 mg/L concentration represents the threshold pain re-occurrence level.
Figure 24:
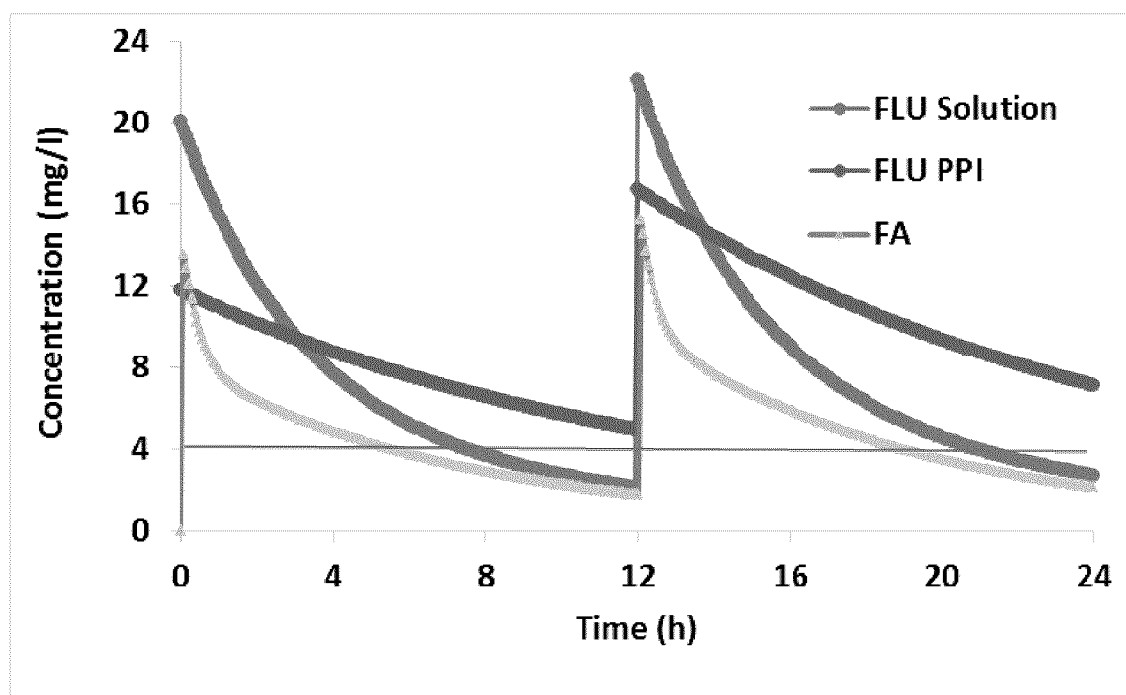
FIG. 24 comparative simulation of human FLU concentration following bid IV dose of 100 mg FLU in solution vs PPI 1501 formulation and FA. The horizontal line corresponding to 4 mg/L concentration represents the threshold pain re-occurrence level.
Figure 25:
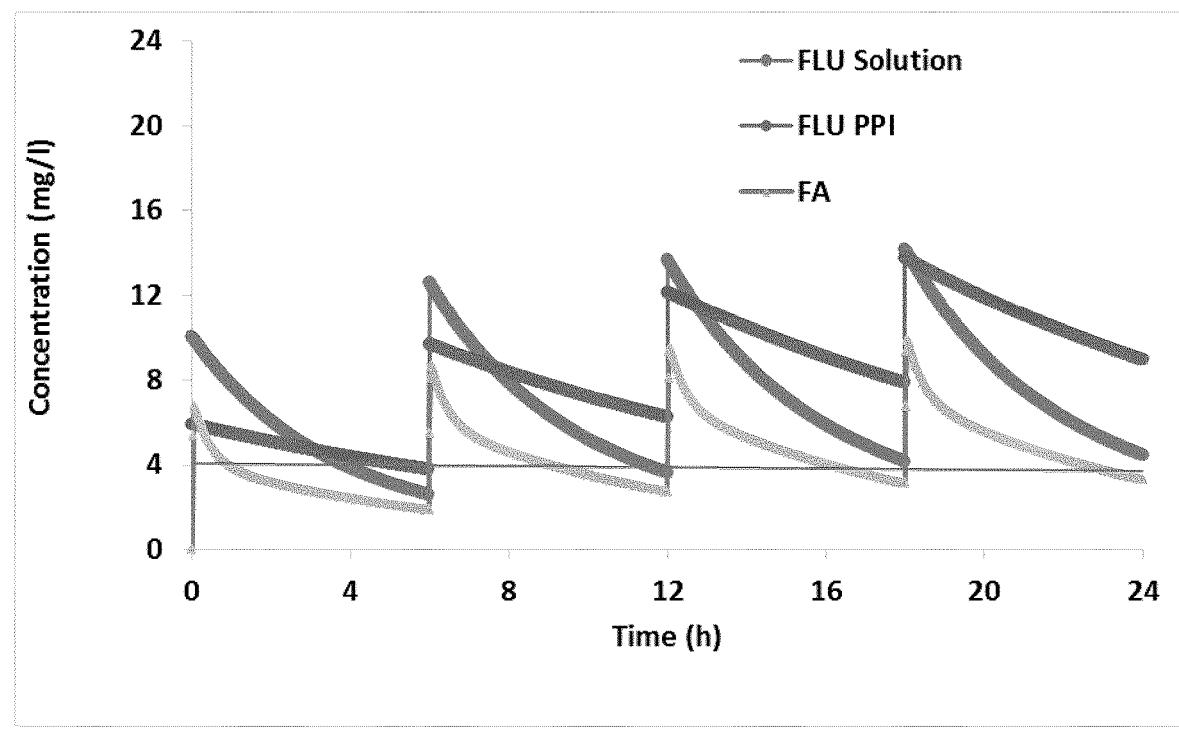
FIG. 25 Comparative simulation of human FLU concentration following q6 h IV dose of 50 mg FLU in solution vs PPI 1501 formulation and FA. The blue horizontal line corresponding to 4 mg/L concentration represents the threshold pain re-occurrence level.

These compartmental parameter values were further used to simulate the IV time-concentration profiles of FLU in solution vs those in PPI 1501 and IV dosed prodrug FA (FIGS. 23-25).

the putative minimum therapeutic FLU concentration of 4 mg/L. However, the PPI 1501 formulation delivered the highest plasma concentrations after 4 hrs and maintained the plasma concentrations>4 mg/L for over 14.9 hrs. In comparison, following the same IV dose of FA, the duration of plasma concentrations>4 mg/L was only 5.5 hrs, almost 3-fold shorter (FIG. 23); The FA injection also resulted in the highest plasma Cmax/C24 ratio, a parameter closely related to the safety profile of FLU (Table 43). FLU from PPI-1501 exhibited the lowest such ratio.

Similar results were observed following bid iv dose of 100 mg, or 4 times a day at 50 mg FLU in solution vs that in PPI 1501 formulation and IV dosed FA (FIGS. 24 and 25). In particular, the plasma FLU concentrations remained >4 mg/L for 23.2 hrs and >24 hrs following the IV dose of FLU in PPI 1501 formulation only, compared to 12.5 hrs in both dosages following IV doses of FA (Table 43).

TABLE 43

Comparative PK parameters of FLU in solution and in PPI 1501 vs that of FA following different iv dosages

| Dosage | Formulation | $C_{max}$ (mg/l) | C24 (mg/l) | $C_{max}/C_{24}$ (Fold) | Accumulative Duration (time > 4 mg/L, h) | Improvement Accum. Duration vs. FA (fold) | Improvement $C_{max}/C_{24}$ Ratio (fold) |
|---|---|---|---|---|---|---|---|
| 100 mg qd | FLU Solution | 20.1 | 0.59 | 34.1 | 7.4 | 1.3 | 1.1 |
|  | FLU PPI | 11.8 | 2.17 | 5.4 | 14.9 | 2.7 | 6.9 |
|  | FA | 13.6 | 0.36 | 37.8 | 5.5 | 1.0 | 1.0 |
| 100 mg bid | FLU Solution | 22.1 | 2.67 | 8.3 | 17 | 1.4 | 0.9 |
|  | FLU PPI | 16.7 | 7.07 | 2.4 | 24 | 1.9 | 3.1 |
|  | FA | 15.3 | 2.07 | 7.4 | 12.5 | 1.0 | 1.0 |
| 50 mg q6h | FLU Solution | 14.2 | 4.5 | 3.2 | 21.5 | 1.7 | 1.0 |
|  | FLU PPI | 13.7 | 8.9 | 1.5 | 23.2 | 1.9 | 1.9 |
|  | FA | 9.9 | 3.3 | 3.0 | 12.5 | 1.0 | 1.0 |

FIG. 23 depicts comparative simulation of human FLU concentration following a single iv dose of 100 mg FLU in solution (the upper line at time 0) vs PPI 1501 formulation (the upper line at 24 h) and FA (the lower line). Here, a 4 mg/L concentration represents the threshold pain re-occurrence level.

FIG. 24 depicts comparative simulation of human FLU concentration following bid iv dose of 100 mg FLU in solution (the upper line at time 0) vs PPI 1501 formulation (the upper line at 24 h) and FA (the lower line). The horizontal line corresponds to 4 mg/L concentration represents the threshold pain re-occurrence level.

FIG. 25 depicts Comparative simulation of human FLU concentration following q6 h iv dose of 50 mg FLU in solution (the upper line at time 0) vs PPI 1501 formulation (the upper line at 24 h) and FA (the lower line). The horizontal line corresponding to 4 mg/L concentration represents the threshold pain re-occurrence level.

As shown in FIG. 23, the plasma concentration of FLU was greatest following IV administration of 100 mg of the drug as a simple solution; the lowest peak plasma concentration was displayed when 100 mg of FLU in PPI 1501 was administered; in all cases however Cmax were greater than In conclusion, the present study demonstrated that FLU in PPI 1501 in rats showed a higher AUC post delivery than that achieved by FLU in solution or FA, mostly due to the reduced drug clearance. Assuming the same differences of 2 compartmental parameters apply similarly to human, then the 100 mg FLU qd dosing, or bid, or q6 h of 50 mg, may have an advantage of achieving plasma concentrations>4 mg/L (a threshold effective concentration) for 14.9 and >23.2 hrs, ~3 or 2 fold better than IV dosed FA. In addition, the reduced Cmax/C24 ratio may be representing another benefit for the safety profile.

Example 5: Protection from Haemolysis

Introduction

The haemo-protective effect of API formulations comprising the PVP-PLA block copolymers was studied.

Methods

The PVP-PLA block copolymers tested were from a further synthesized batch, in which n=27 (average value), m=35 (average value), Mn(PLA)=2075, Mn(PVP)=3980, and Mn(PLA-PVP)=6055 (as determined by NMR). The % PLA was 44%, and the % PVP was 56 (the latter two values determined by TGA). Accordingly, the polymer would be understood to be within the broadest parameters of Groups 1 to 3, as defined here.

To test the ability of the formulations to mitigate the haemolytic potential of the API, in vitro haemolysis experiments were conducted as follows. Human red blood cells (RBC) were isolated by centrifugation from whole blood collected in vaccutainer containing EDTA. RBC were washed three times in normal saline and finally diluted in PBS 9:1 at pH 7.4. Freeze-dried formulations were reconstituted in water and then diluted to the desired concentrations with PBS. RBC suspension was mixed with formulations to generate a final concentration of API from 0.05 mg/mL to 5 mg/mL (it being understood that a 5 mg/mL concentration of API in the blood of a human is far greater than that that could be used therapeutically), incubated at 37° C. for 60 min and centrifuged to remove intact RBC. 0.1 mL of supernatant was diluted with 0.75 mL of PBS and transferred to cuvette. Absorbance A of such solution was determined at 540 nm using Agilent Cary UV-Vis-NIR 5000 spectrometer. Control samples for 0 and 100% haemolysis were prepared by incubating RBC with PBS and 1% Triton X-100, respectively, Percent haemolysis is expressed as $100 \times (A-A_0)/(A_{100}-A_0)$, where $A_0$ and $A_{100}$ is absorbance of negative and positive control, respectively.

Results

Figure 26:
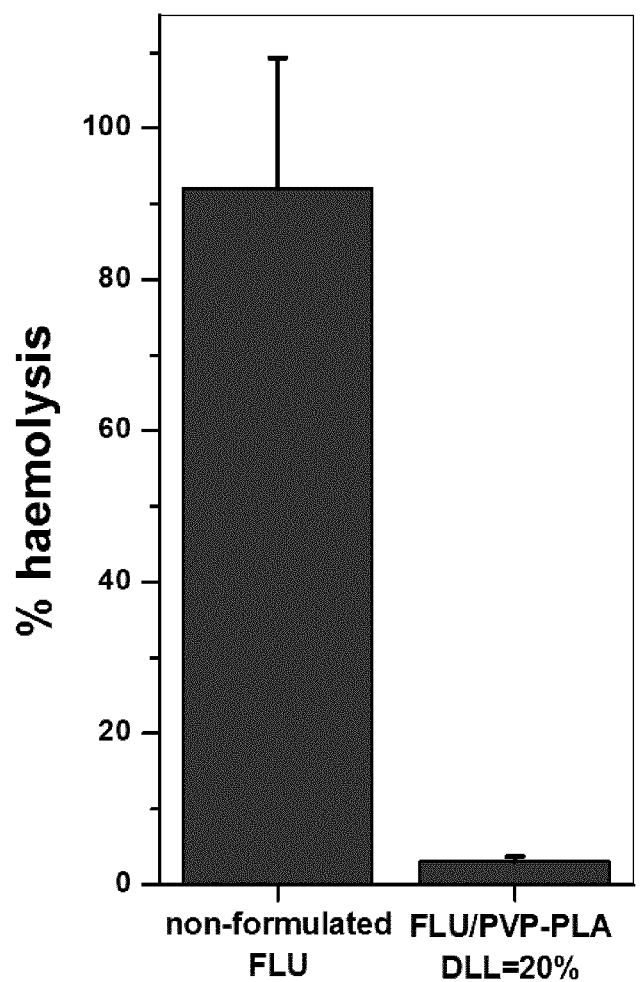
FIG. 26 shows percent haemolysis measured for non-formulated flurbiprofen and its formulation both at the same concentration of 5 mg/mL.

FIG. 26 shows percent haemolysis measured for non-formulated flurbiprofen and PVP-PLA/FLU formulation (DLL=20%) at the same concentration of 5 mg/mL. The data represent a single experiment conducted in triplicate±standard deviation. Measured absorbance values at 540 nm were as follows: 0.10±0.01 (0% haemolysis control), 0.58±0.03 (100% haemolysis control), 0.12±0.01 (FLU/PVP-PLA), 0.54±0.03 (FLU). Non-formulated flurbiprofen (FLU) shows significant haemolytic activity, resulting in the high value of 92.1±17.2% of haemolysis. In contrast, when FLU is entrapped into PVP-PLA vehicles (FLU/PVP-PLA), essentially no haemolysis is observed (% haemolysis=3.1±0.6%), showing strong protective effect of polymer micelles on the encapsulated drug.

Figure 27:
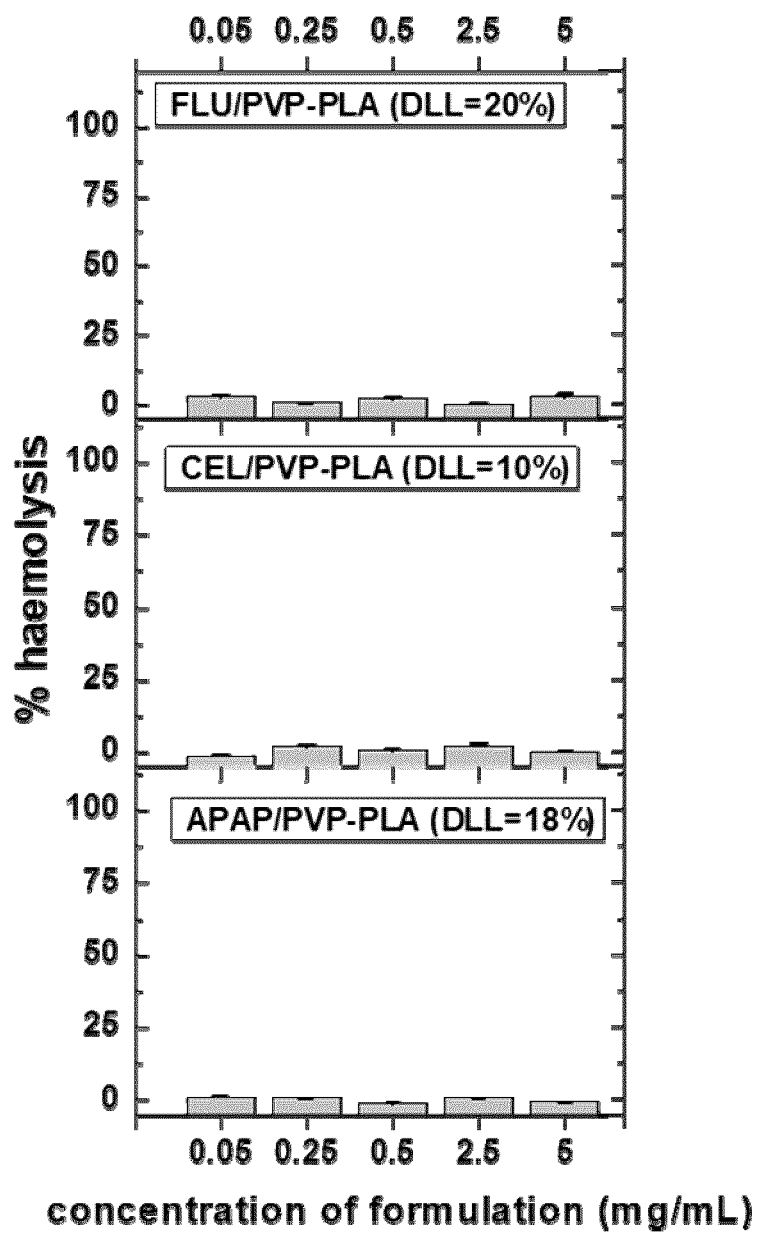
FIG. 27 shows percent haemolysis for different concentrations of drug in formulations of flurbiprofen, celecoxib and acetaminophen.

FIG. 27 shows percent haemolysis for different concentrations of drug in formulations of flurbiprofen (FLU), celecoxib (CEL), and acetaminophen (APAP). The data points represent single experiments conducted in triplicate±standard deviation. Essentially no haemolysis (% haemolysis<10%) was observed for celecoxib and acetaminophen formulations in the whole concentration range studied, i.e. for concentrations≤25 mg/mL and 50 mg/mL, for CEL and APAP, respectively.

Discussion

In all cases, the PVP-PLA micelles displayed the ability to mitigate the haemolytic activity of APIs towards to red blood cells, thereby establishing a protective effect. API such as Flu, APAP and Cel can have been shown to induce haemolysis in human red blood cells at various concentrations and to various degrees. Micelles, such as PVP-PLA micelles, by encapsulation of API have been demonstrated herein to possess a heamo-protective effect whereby they mitigate the haemolytic activity of the API. This is borne out most markedly by the experiments involving flurbiprofen. This haemo-protective ability provides an important safety feature for delivery of API, e.g., via the parenteral route where initial concentrations of API may be very high.

Example 6: General Discussion

Novel PVP-PLA block copolymers have been described herein, along with novel production methods that demonstrate a surprising efficiency of synthesis.

These copolymers have been used to increase the water solubility drug molecules many thousand fold to produce novel dry and liquid formulations suitable for administration.

Trends in copolymer properties have been observed, such that polymers could be designed for, e.g. a particular API, or to achieve a more flexible drug delivery platform.

These novel formulations have been lyophilized to optimize their stability at both room temperature and elevated temperatures as could occur from time to time. The solid products so produced reconstitute rapidly in aqueous solution to generate very high concentration, low viscosity liquids.

These liquids, when injected into animals, generate very generate high blood concentrations of their drug entrapped drug. Thus, the nature of the novel PVP-PLA species renders insoluble drugs soluble in aqueous solution, maintains them in an amorphous form in both liquid and solid forms, stabilizes them, and delivers them rapidly and in high concentration to the blood post-intravenous injection.

Such properties are ideal for, e.g., postoperative pain products, which generate analgesia rapidly and reliably. The PVP-PLA polymers advantageously prolong residence time in the blood, and thereby maintain analgesia for longer. Some polymers have been shown to maintain effective levels of and API in the blood for at least 12 hours. This can mean fewer injections for a subject, and less pain recurrence (breakthrough pain).

Most importantly such products may provide the patient with effective and safe, convenient, low discomfort analgesics with the opportunity to replace, or significantly reduce the need for, opioid analgesics with their many drawbacks. The copolymers may be used, e.g., for oral or parenteral administration.

The block copolymers described were synthesized using a novel process that produced high purity products in yields unexpected for this type of system. The characteristics of the copolymers so synthesized enable a range of insoluble drugs to be entrapped in high concentration and rendered amorphous to enable rapid release in vivo once administered.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. Kazunari Masutani, Yoshiharu Kimura, PLA Synthesis. From the Monomer to the Polymer, chapter 1, The Royal Society of Chemistry, 2015, pages 1-36.
2. Ann-Christine Albertsson, Indra K. Verma, Recent Development in Ring Opening Polymerization of Lactones for Biomedical Applications, Biomacromolecules, 2003, 4, pages 1466-1486.
3. Irene Bartolozzi, Roberto Solaro, Etienne Schacht, Emo Chiellini, Hydroxyl end-capped macromers of N-vinyl-2-pyrrolidinone as precursors of amphiphilic block copolymers, European Polymer Journal, 2007, 43, pages 4628-4638.
4. Lionel Delaude, Morgan Hans, Somenath Chowdhury, Microwave-Assisted Synthesis of the 1,3-Dimesitylimidazolinium Chloride, Org. Synth., 2010, 87, pages 77-87.
5. Lei Xiong, Hong Wei JiangAffiliated withSouth China University of Technology, Di Zhen Wang, Synthesis, characterization and degradation of poly(dl-lactide)-block-polyvinylpyrrolidone-block-poly(dl-lactide) copolymers, Journal of Polymer Research, 2009, 16, pages 191-197.
6. K M Park, C K Kim. (1999) Preparation and evaluation of flurbiprofen-loaded microemulsion for parenteral delivery. Intl J Pharmaceutics, 181: 173-179.
7. R D Knihinicki, R O Day, G G Graham, K M Williams. (1990) Stereoselective disposition of ibuprofen and flurbiprofen in rats. Chirality, 2: 134-140.
8. Szpunar, G. J., Albert, K. S., Bole, G. G., Dreyfus, J. N., Lockwood, G. F. and Wagner, J. G. (1987), Pharmacokinetics of flurbiprofen in man. I. Area/dose relationships. Biopharm. Drug Dispos., 8: 273-283.
9. Cefali, E. A., Poynor, W. J., Sica, D. and Cox, S. (1991), Pharmacokinetic Comparison of Flurbiprofen in End-Stage Renal Disease Subjects and Subjects with Normal Renal Function. Journal of Clinical Pharma, 31: 808-814.
10. Taburet, A. M., Singlas, E., Glass, R. C., Thomas, F. and Leutenegger, E. (1995), Pharmacokinetic comparison of oral and local action transcutaneous flurbiprofen in healthy volunteers. Journal of Clinical Pharmacy and Therapeutics, 20: 101-107.
11. Qayyum, A., Najmi, M. H. and Farooqi, Z-R. (2011) Determination of Pharmacokinetics of Flurbiprofen in Pakistani Population Using Modified HPLC Method. J. Chromatogr. Sci. 49: 108-113.
12. Kaiser D G, Brooks C D, Lomen P L. (1986) Pharmacokinetics of flurbiprofen. Am. J. Med. 80(3A):10-5.
13. Kumpulainen E, Välitalo P, Kokki M, Lehtonen M, Hooker A, Ranta V P, Kokki H. (2010) Plasma and cerebrospinal fluid pharmacokinetics of flurbiprofen in children. Br J Clin Pharmacol. 70:557-66 5

What is claimed is:

1. A dry pharmaceutical composition comprising PVP-PLA block copolymers as defined in Formula I:

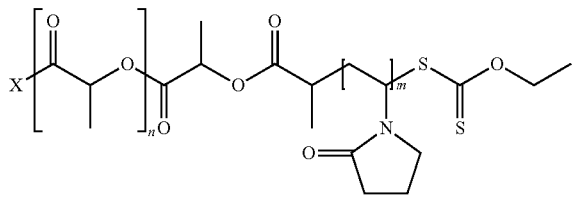

wherein:
x is an initiator alcohol having a boiling point greater than 145° C.,
n is, on average, from 20 and 40, and
m is, on average, from 10 and 40,
wherein the block copolymers have a number average molecular weight ($M_n$) of at least 3000 Da,
in molecular association with at least one active pharmaceutical ingredient (API).

2. The dry pharmaceutical composition of claim 1, which is reconstitutable in water or an aqueous solution to form a liquid comprising nanoparticles formed of the PVP-PLA block co-polymers and comprising the at least one API.

3. The dry pharmaceutical composition of claim 1, which is freeze dried or spray dried.

4. The dry pharmaceutical composition of claim 1, which is amorphous.

5. The dry pharmaceutical composition of claim 1, which is stable for at least six months at 40° C.

6. The dry pharmaceutical composition of claim 1, having a drug loading level (DLL) of at least 5% wt/wt of the at least one API.

7. The dry pharmaceutical composition of claim 1, wherein the boiling point of the initiator alcohol is greater 200° C.

8. The dry pharmaceutical composition of claim 1, wherein the initiator alcohol is selected from the group consisting of:
1-hexanol;
1-heptanol;
diethylene glycol monoethyl ether;
diethylene glycol mono methyl ether;
triethylene glycol mono methyl ether;
tetraethylene glycol mono methyl ether;
oligo-ethylene glycol mono methyl ethers of formula II

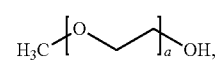

wherein a≥5;
oligo-ethylene glycol mono ethyl ethers of formula III

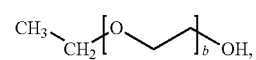

wherein b≥1; and
mixtures thereof.

9. The dry pharmaceutical composition of claim 1, wherein x is diethylene glycol mono ethyl ether (DEGMEE).

10. The dry pharmaceutical composition of claim 1, wherein:
n is, on average, from 21.5 to 28,
m is, on average, from 18 to 37,
the PVP-PLA block copolymers have a number average molecular weight of 4600 Da to 6600 Da,
the PVP-PLA block copolymers comprise a PLA block which has a number average molecular weight of 1600 Da to 2900 Da,
the PVP-PVP block copolymers comprise a PVP block which has a number average molecular weight of 1900 Da to 4200 Da, a ratio of the number average molecular weight of the PLA block to the number average molecular weight of the PVP block (PLA:PVP) of 0.3 to 1.4, a weight average molecular weight ($M_w$) of the PLA in the block copolymers is 35% to 60%, based on the total weight of the polymer, and a weight average molecular weight ($M_w$) of PVP in the block copolymers is 40% to 65%, based on the total weight of the polymer, wherein the number average molecular weight is as measured by proton nuclear magnetic resonance (NMR) and the weight average molecular weight is as measured by thermogravimetric analysis (TGA).

11. The dry pharmaceutical composition of claim 10, wherein:

n is, on average, from 21.5 to 28, m is, on average, from 25 to 37, the PVP-PLA block copolymers have a number average molecular weight of 4800 Da to 6600 Da, the number average molecular weight of the PLA block is 1600 Da to 2900 Da, the number average molecular weight of the PVP block is 2700 Da to 4200 Da, the ratio of the number average molecular weight of the PLA block to the number average molecular weight of the PVP block (PLA:PVP) of 0.3 to 1.0, and the weight average molecular weight ($M_w$) of PVP in the block copolymers is 40% to 65%, based on the total weight of the polymer.

12. The dry pharmaceutical composition of claim 11, wherein:

n is, on average, from 24 to 28, m is, on average, from 25 to 33, the PVP-PLA block copolymers have a number average molecular weight of 5400 Da to 6600 Da, the number average molecular weight of the PLA block is 2200 Da to 2900 Da, the number average molecular weight of the PVP block is 2700 Da to 3700 Da, the ratio of the number average molecular weight of the PLA block to the number average molecular weight of the PVP block (PLA:PVP) of 0.5 to 1.0, the weight average molecular weight ($M_w$) of PLA in the block copolymers is 35% to 50%, based on the total weight of the polymer, and the weight average molecular weight ($M_w$) of PVP in the block copolymers is 50% to 65%, based on the total weight of the polymer.

13. The dry pharmaceutical composition of claim 1, wherein the PVP-PLA block copolymers have a polydispersity index (PDI) of ≤1.8, wherein the PDI is as measured by gel permeation chromatography with light scattering (GPC-LS).

14. The dry pharmaceutical composition of claim 1, wherein the at least one API is hydrophobic.

15. The dry pharmaceutical composition of claim 1, wherein the at least one API comprises an analgesic.

16. The dry pharmaceutical composition of claim 15, wherein the analgesic comprises a nonsteroidal anti-inflammatory drug (NSAID).

17. The dry pharmaceutical composition of claim 16, wherein the NSAID comprises flurbiprofen.

18. The dry pharmaceutical composition of claim 16, wherein the NSAID comprises celecoxib.

19. The dry pharmaceutical composition of claim 15, wherein the analgesic comprises acetaminophen.

20. The dry pharmaceutical composition of claim 1, wherein the at least one API comprises an anesthetic.

21. The dry pharmaceutical composition of claim 20, wherein the anesthetic comprises propofol.

22. The dry pharmaceutical composition of claim 1, which is reconstitutable in water or aqueous solution to form an essentially clear liquid comprising nanoparticles formed of the PVP-PLA block copolymers and comprising the at least one API.

23. The dry pharmaceutical composition of claim 22, wherein the essentially clear liquid comprises at least 20 g/L of the API.

24. The dry pharmaceutical composition of claim 10, which comprises at least two different APIs.

25. The dry pharmaceutical composition of claim 24, wherein the at least two different APIs are selected from the group consisting of flurbiprofen, acetaminophen, propofol, and celecoxib.

26. The dry pharmaceutical composition of claim 11, which comprises at least three different APIs.

27. The dry pharmaceutical composition of claim 26, wherein the at least three different APIs are selected from the group consisting of flurbiprofen, celecoxib, acetaminophen, and propofol.

* * * * *